US011142775B2

(12) United States Patent
Yan et al.

(10) Patent No.: US 11,142,775 B2
(45) Date of Patent: Oct. 12, 2021

(54) BOCAPARVOVIRUS SMALL NONCODING RNA AND USES THEREOF

(71) Applicants: University of Iowa Research Foundation, Iowa City, IA (US); University of Kansas, Lawrence, KS (US)

(72) Inventors: Ziying Yan, Iowa City, IA (US); John F. Engelhardt, Iowa City, IA (US); Jianming Qiu, Overland Park, KS (US); Zekun Wang, Kansas City, KS (US)

(73) Assignees: University of Iowa Research Foundation, Iowa City, IA (US); University of Kansas, Lawrence, KS (US)

( * ) Notice: Subject to any disclaimer, the term of this patent is extended or adjusted under 35 U.S.C. 154(b) by 0 days.

(21) Appl. No.: 16/477,762

(22) PCT Filed: Jan. 12, 2018

(86) PCT No.: PCT/US2018/013634
§ 371 (c)(1),
(2) Date: Jul. 12, 2019

(87) PCT Pub. No.: WO2018/132747
PCT Pub. Date: Jul. 19, 2018

(65) Prior Publication Data
US 2019/0338312 A1 Nov. 7, 2019

Related U.S. Application Data

(60) Provisional application No. 62/445,987, filed on Jan. 13, 2017.

(51) Int. Cl.

| | |
|---|---|
| *C07H 21/04* | (2006.01) |
| *C12N 15/86* | (2006.01) |
| *A61P 31/20* | (2006.01) |
| *A61K 39/23* | (2006.01) |
| *C12N 7/00* | (2006.01) |
| *A61K 39/00* | (2006.01) |

(52) U.S. Cl.
CPC .............. *C12N 15/86* (2013.01); *A61K 39/23* (2013.01); *A61P 31/20* (2018.01); *C12N 7/00* (2013.01); *A61K 2039/5256* (2013.01); *A61K 2039/53* (2013.01); *C12N 2750/14121* (2013.01); *C12N 2750/14134* (2013.01); *C12N 2750/14143* (2013.01); *C12N 2750/14322* (2013.01); *C12N 2750/14344* (2013.01); *C12N 2750/14362* (2013.01)

(58) Field of Classification Search
None
See application file for complete search history.

(56) References Cited

U.S. PATENT DOCUMENTS

| | | | |
|---|---|---|---|
| 6,491,907 | B1 | 12/2002 | Rabinowitz et al. |
| 8,110,350 | B2 | 2/2012 | Allander et al. |
| 9,828,587 | B2 | 11/2017 | Yan et al. |
| 10,793,835 | B2 | 10/2020 | Yan et al. |
| 2003/0053990 | A1 | 3/2003 | Rabinowitz et al. |
| 2008/0292654 | A1 | 11/2008 | Allander et al. |
| 2009/0297557 | A1 | 12/2009 | Delwart et al. |
| 2011/0014723 | A1 | 1/2011 | Erdman et al. |
| 2013/0012574 | A1 | 1/2013 | Monahan et al. |
| 2016/0068821 | A1 | 3/2016 | Yan et al. |
| 2018/0282702 | A1 | 10/2018 | Yan et al. |
| 2019/0203229 | A1 | 7/2019 | Engelhardt et al. |

FOREIGN PATENT DOCUMENTS

| | | | |
|---|---|---|---|
| AU | 2014251099 | B2 | 1/2019 |
| CN | 105431170 | A | 3/2016 |
| CN | 105431170 | B | 10/2019 |
| EP | 2983707 | B1 | 6/2019 |
| HK | 1217916 | B | 9/2020 |
| IN | 10078DELNP2015 | A | 4/2016 |
| JP | 2002538770 | A | 11/2002 |
| JP | 6516725 | B2 | 4/2019 |
| WO | WO-0028004 | A1 | 5/2000 |
| WO | WO-2014168953 | A1 | 10/2014 |
| WO | WO-2017139381 | A1 | 8/2017 |
| WO | WO-2017205739 | A1 | 11/2017 |
| WO | WO-WO2018132747 | | 7/2018 |

OTHER PUBLICATIONS

Guido et al., 2016 (World Journal of Gastroenterology, 22(39): 8684-8697).*
"U.S. Appl. No. 15/822,956, Notice of Allowance dated Jun. 1, 2020", 5 pgs.
"U.S. Appl. No. 15/822,956, Notice of Allowance dated Dec. 18, 2019", 8 pgs.
"U.S. Appl. No. 15/822,956, Response Filed Nov. 22, 2019 to Final Office Action dated Sep. 23, 2019", 8 pgs.
"Canadian Application Serial No. 2,909,085, Office Action dated Apr. 2, 2020", 5 pgs.
"Indian Application Serial No. 10078/DELNP/2015, First Examination Report daed Mar. 12, 2020", w/ English Translation, 8 pgs.
"Israel Application Serial No. 241954, Office Action dated Dec. 5, 2019", w/ English Translation, 6 pgs.
"New Zealand Application Serial No. 713509, First Examiner Report dated Nov. 14, 2019", 7 pgs.

(Continued)

*Primary Examiner* — Kimberly Chong
(74) *Attorney, Agent, or Firm* — Schwegman Lundberg & Woessner, P.A.

(57) ABSTRACT

Vectors having a nucleotide sequence having SEQ ID NO:1 or a nucleotide sequence having at least 85% identity to SEQ ID NO:1, or a portion thereof, that is capable of regulating bocaparvovirus replication, or vectors having the complement of the nucleotide sequence, and methods of using the vectors, are provided.

9 Claims, 28 Drawing Sheets

Specification includes a Sequence Listing.

(56) References Cited

OTHER PUBLICATIONS

U.S. Appl. No. 14/782,876, filed Oct. 7, 2015, Chimeric Adeno-Associated Virus/ Bocavirus Parvovirus Vector, Now U.S. Pat. No. 9,828,587.
U.S. Appl. No. 15/822,956, filed Nov. 27, 2017, Chimeric Adeno-Associated Virus/ Bocavirus Parvovirus Vector.
U.S. Appl. No. 16/304,064, filed Nov. 21, 2018, cis and trans Requirements for Terminal Resolution of Human Bocavirus 1.
"U.S. Appl. No. 14/782,876, Non Final Office Action dated Feb. 16, 2017", 10 pgs.
"U.S. Appl. No. 14/782,876, Notice of Allowance dated Jul. 25, 2017", 8 pgs.
"U.S. Appl. No. 14/782,876, Preliminary Amendment filed Oct. 7, 2015", 9 pgs.
"U.S. Appl. No. 14/782,876, Response filed Jan. 11, 2017 to Restriction Requirement dated Oct. 14, 2016", 8 pgs.
"U.S. Appl. No. 14/782,876, Response filed Jun. 16, 2017 to Non Final Office Action dated Feb. 16, 2017", 8 pgs.
"U.S. Appl. No. 14/782,876, Restriction Requirement dated Oct. 14, 2016", 10 pgs.
"U.S. Appl. No. 15/822,956, Non Final Office Action dated May 8, 2019", 16 pgs.
"U.S. Appl. No. 15/822,956, Preliminary Amendment filed Nov. 27, 2017", 3 pgs.
"U.S. Appl. No. 15/822,956, Response filed Apr. 8, 2019 to Restriction Requirement dated Feb. 7, 2019", 6 pgs.
"U.S. Appl. No. 15/822,956, Restriction Requirement dated Feb. 7, 2019", 9 pgs.
"U.S. Appl. No. 15/822,956, Supplemental Preliminary Amendment filed Apr. 23, 2018", 9 pgs.
"Australian Application Serial No. 2014251099, First Examination Report dated May 30, 2018", 4 pgs.
"Australian Application Serial No. 2014251099, Response filed Dec. 19, 2018 to Examiner's Report dated May 30, 2018", 39 pgs.
"Chinese Application Serial No. 201480032420.6, Office Action dated May 3, 2017", w/English Translation of Claims, 20 pgs.
"Chinese Application Serial No. 201480032420.6, Office Action dated Jul. 13, 2018", w/ English translation, 8 pgs.
"Chinese Application Serial No. 201480032420.6, Office Action dated Dec. 14, 2017", (English Translation), 8 pgs.
"Chinese Application Serial No. 201480032420.6, Response filed Feb. 27, 2018 to Office Action dated Dec. 14, 2017", w/ Amended Claims, 73 pgs.
"Chinese Application Serial No. 201480032420.6, Response filed Sep. 18, 2017 to Office Action dated May 3, 2017", w/English Claims, 25 pgs.
"Chinese Application Serial No. 201480032420.6, Response filed Nov. 26, 2018 to Office Action dated Jul. 13, 2018", w/ English Claims, 73 pgs.
"European Application Serial No. 14783418.8, Communication Pursuant to Article 94(3) EPC dated Mar. 27, 2018", 4 pgs.
"European Application Serial No. 14783418.8, Extended European Search Report dated Feb. 27, 2017", 15 pgs.
"European Application Serial No. 14783418.8, Response filed May 26, 2016", 13 pgs.
"European Application Serial No. 14783418.8, Response filed May 30, 2018 to Communication Pursuant to Article 94(3) EPC dated Mar. 27, 2018", 271 pgs.
"European Application Serial No. 14783418.8, Response filed Sep. 22, 2017", 11 pgs.
"International Application Serial No. PCT/US2014/033343, International Preliminary Report on Patentability dated Oct. 13, 2015", 12 pgs.
"International Application Serial No. PCT/US2014/033343, International Search Report dated Sep. 2, 2014", 4 pgs.
"International Application Serial No. PCT/US2014/033343, Written Opinion dated Sep. 2, 2014", 10 pgs.
"International Application Serial No. PCT/US2017/017021, International Preliminary Report on Patentability dated Aug. 23, 2018", 12 pgs.
"International Application Serial No. PCT/US2017/017021, International Search Report dated May 23, 2017", 8 pgs.
"International Application Serial No. PCT/US2017/017021, Written Opinion dated May 23, 2017", 10 pgs.
"International Application Serial No. PCT/US2017/034678, International Preliminary Report on Patentability dated Dec. 6, 2018", 9 pgs.
"International Application Serial No. PCT/US2017/034678, International Search Report dated Oct. 16, 2017", 7 pgs.
"International Application Serial No. PCT/US2017/034678, Written Opinion dated Oct. 16, 2017", 6 pgs.
"International Application Serial No. PCT/US2018/013634, International Search Report dated Jun. 18, 2018", 9 pgs.
"International Application Serial No. PCT/US2018/013634, Invitation to Pay Add'l Fees and Partial Search Report dated Apr. 17, 2018", 14 pgs.
"International Application Serial No. PCT/US2018/013634, Written Opinion dated Jun. 18, 2018", 12 pgs.
"Israel Application Serial No. 241954, Office Action dated Oct. 9, 2018", W/English Translation, 10 pgs.
"Israel Application Serial No. 241954, Response filed Feb. 7, 2019 to Office Action dated Oct. 9, 2018", w/ English Translation, 14 pgs.
"Japanese Application Serial No. 2016-507610, Notification of Reasons for Refusal dated Jan. 24, 2019", w/ English translation, 6 pgs.
"Japanese Application Serial No. 2016-507610, Office Action dated Feb. 21, 2018", with English translation of claims, 16 pgs.
"Japanese Application Serial No. 2016-507610, Response filed Mar. 6, 2019 to Notification of Reasons for Refusal dated Jan. 24, 2019", with machine Translation, 10 pgs.
"Japanese Application Serial No. 2016-507610, Response filed Aug. 21, 2018 to Office Action dated Feb. 21, 2018", with English translation of claims, 31 pgs.
Brown, Kevin E., "The expanding range of parvoviruses which infect humans", Reviews in Medical Virology, GB, (2010), vol. 20, No. 4, (2010), 231-244.
Cheung, Andrew K., et al., "Identification and molecular cloning of a novel porcine parvovirus", Archives of Virology; Official Journal of the Virology Division of the International Union of Microbiological Societies, Springer-Verlag, VI, vol. 155, No. 5, (2010), 801-806.
Deng, Xuefeng, et al., "In vitro modeling of human bocavirus 1 infection of polarized primary human airway epithelia", J Viral. vol. 87, No. 7, 4097-4102, (Jan. 23, 2013), 7 pgs.
Gao, Fend, et al., "DNA-guided genome editing using the Natronobacterium gregoryi Argonaute", In Journal of Nature Biotechnology Advance Online Publication, (May 2, 2016), 1-7.
Guido, et al., "", World Journal of Gastroenterology, (2016), 8684-8697.
Gurda, Brittney L., et al., "Human Bocavirus Capsid Structure: Insights into the Structural Repertoire of the Parvoviridae", Journal of Virology, 84(12), (Jun. 2010), 5880-5889.
Haung, Qinfeng, et al., "Establishment of a Reverse Genetics System for Studying Human Bocavirus in Human Airway Epithelia", Journal PLOS Pathogens vol. 8(8), (2012), 1-14.
Ishiawata, Akira, et al., "Phenotype correction of hemophilia A mice with adeno-associated virus vectors carrying the B domain-deleted canine factor VIII gene", Thrombosis Research, Tarrytown, NY, US, vol. 118, No. 5, (2006), (2006), 627-635.
Julia, Fakhiri, et al., "254. New Chimeric Gene Therapy Vectors Based on Four Different Mammalian Bocaviruses", Molecular Therapy, vol. 24, No. S1, (May 1, 2016), S100.
Kapoor, Amit, et at., "Bocavirus Episome in Infected Human Tissue Contains Non-Identical Termini", PLOS One, (2011), vol. 6, No. 6, e21362, (2011), 8 pgs.
Kapoor, Amit, et al., "Identification and Characterization of a New *bocavirus* Species in Gorillas", PLOS One, (2010), vol. 5, No. 7, p. e11948, (Jul. 2010), 6 pgs.

(56) References Cited

OTHER PUBLICATIONS

Li, Wuping, et al., "Generation of Novel AAV Variants by Directed Evolution for Improved CFTR Delivery to Human Ciliated Airway Epithelium", Journal of Molecular Therapy vol. 17(12), (Dec. 2009), 2067-2077.

Mihaylov, Ivailo, et al., "Complementation for an essential ancillary non-structural protein function across Parvovirus genera", Virology, vols. 468-470, (2014), 226-237.

Olufemi, Fasina O, et al., "NP1 protein of the Bocaparvovirus Minute Virus of Canines controls acess to the viral capsid genes via its role in RNA processing", Journal of Virology., vol. 90, No. 4, (Dec. 4, 2015), 1718-1728.

Qinfeng, Huang, et al., "Internal polyadenylation of pavoviral precurser mRNA limits progeny virus production", Virology, Elsevier, Amsterdam, NL, vol. 426, No. 2, (Jan. 26, 2012), 167-177.

Qiu, Jianming, et al., "Characterization of the transcription profile of adeno-associated virus type 5 reveals a number of unique features compared to previously characterized adeno-associated viruses", Journal of Virol., 76, No. 24, (2002), 12435-12447.

Qiu, Jianming, et al., "The Transcription Profile of the Bocavirus Bovine Parvovirus Is Unlike Those of Previously Characterized Parvoviruses", Journal of Virology, vol. 81, No. 21, [Online]. Retrieved from the Internet: <URL: https://jvi.asm.org/>, (2007), 12080-12085.

Ros, C, et al., "The ubiquitin-proteasome machinery is essential for nuclear translocation of incoming minute virus of mice", Virology 324, (2004), 350-360.

Shen, Weiran, et al,, "Analysis of cis and trans Requirements for DNA Replication at the Right-End Hairpin of the Human Bocavirus 1 Genome", Journal of Virology 90.17, (2016), 7761-7777.

Sukhu, L, et al., "Characterization of the Nonstructural Proteins of the Bocavirus Minute Virus of Canines", Journal of Virology., vol. 87, No. 2, (Nov. 7, 2012), 1098-1104.

Sun, et al., "Molecular Characterization of Infectious Clones of the Minute Virus of Canines Reveals Unique Features of Bocaviruses", Journal of Virology, 83(8), (Apr. 2009), 3956-3967.

Wang, Zekun, et al., "Parvovirus Expresses a Small Noncoding RNA That Plays an Essential Role in Virus Replication", Journal of Virology, vol. 91 Issue 8, (2017), 1-20.

Wei, Ran Shen, et al., "Identification and functional analysis of novel nonstructural proteins of human bocavirus 1", Journal of Virology., vol. 89, No. 19, (Oct. 1, 2015), 10097-10109.

Wei, Zou, et al., "Nonstructural Protein NP1 of Human Bocavirus 1 Plays a Critical Role in the Expression of Viral Caspid Proteins", Journal of Virology., vol. 90, No. 9, (May 1, 2016), 4658-4669.

Xuefeng, Deng, et al., "DNA Damage Signaling Is Required for Replication of Human Bocavirus 1 DNA in Dividing HEK293 Cells", Journal of Virology, vol. 91 No. 1, (Jan. 1, 2017), 20 pgs.

Xuefeng, Deng, et al., "Replication of an Autonomous Human Parvovirus in Non-dividing Human Airway Epithelium Is Facilitated through the DNA Damage and Repair Pathways", PLOS Pathogens vol. 12 No. 1, (Jan. 14, 2016), 25 pgs.

Y, Sun, et al., "Molecular Characterization of Infectious Clones of the Minute Virys of Canines Reveals Unique Features of Bocaviruse", Journal of Virology vol. 83 No. 8, (Feb. 11, 2009), 3956-3967.

Yan, Z, et al., "A Novel Chimeric Adenoassociated Virus 2/ Human Bocavirus 1 Parvovirus Vector Ef?ciently Transduces Human Airway Epithelia", Molecular Therapy, vol. 21 No. 12, (Dec. 2013), 2181-2194.

Yan, Z., et al., "A novel chimeric adenoassociated virus 2/human bocavirus 1 parvovirus vector efficiently transduces human airway epithelia", Mol Ther. vol. 21, No. 12, (Jul. 30, 2013), 2181-2194.

Yang, Wan-Zhu, et al,, "Genome characterization of a novel porcine bocavirus", Archives of Virology; Official Journal of the Virology Division of the International Union of Microbiological Societies, Springer-Verlag, VI, (2012), vol. 157, No. 11,, (Jul. 21, 2012), 2125-2132.

Zou, Wei, et al., "Nonstructural Protein NP1 of Human Bocavirus 1 Plays Critical Role in the Expression of Viral Capsid Protein", Journal of Virology May 2016 vol. 90 No. 9, (Feb. 18, 2016), 4658-4669.

"U.S. Appl. No. 15/822,956, Response filed Aug. 8, 2019 to Non-Final Office Action dated May 8, 2019", 9 pgs.

"International Application Serial No. PCT/US2018/013634, International Preliminary Report on Patentability dated Jul. 25, 2019", 12 pgs.

Ginn, S. L., et al., "Gene therapy clinical trials worldwide to 2012—an update.", J Gene Med, 15(2), (2013), 65-77.

Kapoor, A., et al., "Human bocaviruses are highly diverse, dispersed, recombination prone, and prevalent enteric infections", J Infect Dis. 201(11), (Jun. 2010), 1633-1643.

Ricour, C., et al., "Human Bocavirus, A Newly Discovered Parvovirus of the Respiratory Tract", International Journal of Clinical and Laboratory Medicine, vol. 63, Issue 5, Abstract only, (2008), 329-334.

"U.S. Appl. No. 15/822,956, Final Office Action dated Sep. 23, 2019", 9 pgs.

"Canadian Application Serial No. 2909085, Voluntary Amendment Filed Sep. 6, 2019", 4 pgs.

Fakhiri, Julia, et al., "Novel Chimeric Gene Therapy Vectors Based on Adeno-Associated Virus and Four Different Mammalian Bocaviruses", Molecular Therapy: Methods & Clinical Development vol. 12, (Mar. 2019), 202-222.

Yan, Ziying, et al., "Human Bocavirus Type-1 Capsid Facilitates the Transduction of Ferret Airways by Adeno-Associated Virus Genomes", Human Gene Therapy, vol. 28, No. 8, (2017), 612-625.

"Canadian Application Serial No. 2,909,085, Response filed Jul. 30, 2020 to Office Action dated Apr. 2, 2020", 29 pgs.

"Canadian Application Serial No. 2,909,085, Office Action dated Feb. 16, 2021", 4 pgs.

Denby, L., et al., "Adeno-associated virus (AAV)-7 and -8 poorly transduce vascular endothelial cells and are sensitive to proteasomal degradation.", Gene Ther., 12(20), (Oct. 2005), 1534-8.

Douar, A., et al.. "Intracellular trafficking of adeno-associated virus vectors: routing to the late endosomal compartment and proteasome degradation.", J Virol., 75(4), (Feb. 2001), 1824-33.

Hermonat, Paul, et al., "Use of adeno-associated virus as a mammalian DNA cloning vector: Transduction of neomycin resistance into mammalian tissue culture cells", Proc. Natl. Acad. Sci, USA, vol. 81, (Oct. 1984), 6466-6470.

Jennings, K., et al., "Proteasome inhibition enhances AAV-mediated transgene expression in human synoviocytes in vitro and in vivo", Mol Ther., 11(4), (Apr. 2005), 600-7.

Muzyczka, N., "Use of Adeno-Associated Virus as a General Transduction Vector for Mammalian Cells", In: Current Topics in Microbiology and Immunology, 158, Springer-Verlag, Berlin: R.W. Compans, et al., (Eds.), (1992), pp. 97-129.

Pratelli, Annamaria, et al., "Host range of Canine minute virus in cell culture", Journal of Veterinary Diagnostic Investigation 24(5), (Jul. 23, 2012), 981-985.

Salganik, Max, et al., "Adeno-associated Virus as a Mammalian DNA Vector", Microbiol. Spectr., 3:10.1128, (Aug. 2015), 32 pgs.

Wang, Jiali, et al., "Identification of a novel bocaparvovirus in a wild squirrel in Kunming, Yunnan Province, China", Archives of Virology 165, (2020), 1469-1474.

Wang, Zekun, et al., "Development of a Novel Recombinant Adeno-Associated Virus Production System Using Human Bocavirus 1 Helper Genes", Molecular Therapy: Methods & Clinical Development vol. 11, (Dec. 2018), 40-51.

Wu, Jihong, et al., "Enhanced transduction and improved photoreceptor survival of retinal degeneration by the combinatorial use of rAAV2 with a lower dose of adenovirus", Vision Research 48, (2008), 1648-1654.

Zhang, Chi, et al., "Identification and characterization of a novel rodent bocavirus from different rodent species in China", Emerging Microbes & Infections 7:48, (2018), 11 pgs.

Zinn, Eric, et al., "Adeno-associated Virus: Fit to serve", Curr Opin Virol., (Oct. 2014), 13 pgs.

(56) References Cited

OTHER PUBLICATIONS

Allander, Tobias, "Cloning of a human parvovirus by molecular screening of respiratory tract samples", PNAS, 102(36), (2005), 12891-12896.
Arnold, John, "Human Bocavirus Prevalence and Clinical Spectrum at a Childrens Hospital", Clin Infect Dis. 43, (2006), 283-288.
Iwane, Marika, "(Abstract) Population-based surveillance for hospitalizations associated with respiratory syncytial virus, influenza virus, and parainfluenza viruses among young children,", Pediatrics, 113(6). pp. 1758-1764, (2004), 2 pgs.
Ma, Xiaoming, "Detection of Human Bocavirus in Japanese Children with Lower Respiratory Tract Infections", J Clin Microbiol, 44, (2006), 1132-1134.
Shay, David, "Bronchiolitis-Associated Hospitalizations Among US Children, 1980-1996", JAMA, vol. 282, No. 15, (1999), 1440-1446.
Sloots, Theo, "Evidence of human coronavirus HKU1 and human bocavirus in Australian Children", J Clin Virol, 35, (2006), 99-102.

\* cited by examiner

| Virus | Accession # | | | | | | | | |
|---|---|---|---|---|---|---|---|---|---|
| | | nt 5199 | A-box | | 5240 | 5250 | B-box | 5270 | |
| HBoV1 | JQ923422 | AAGTTCCTCCTCAATGGACAAGCGGAAGTGAAGGGTGACTGTAGTCCTGAGCTCATGGGTTCAAGACCACAGCCGAT |
| HBoV3 | EU918736 | ........TC..............T.....AA...............A...C.........A....G..G.T....T.... |
| GBoV | HM145750 | .......CTTC..............T....T.AA...............A...C.........A....G..G.T....T.... |
| HBoV2a | FJ973558 | ........TC..............T.....AA...............A...C.........A....G..G.T....T.... |
| HBoV2b | FJ973560 | ........TC..............T.....AA...............A...C.........AA...G..G.T....T.... |
| HBoV2c | FJ170278 | ........TC..............T.....AA...............A...C.........A....G..G.T....T.... |
| HBoV4 | FJ973561 | ........TC..............T.....AA...............A...C.........A....G..G.T....T.... |

| | | | | | | |
|---|---|---|---|---|---|---|
| 5280 | 5290 | | 5310 | 5320 | 5330 | 5339 |
| GGTAGTGGTGTTAACGTTTCGAACCTAGCCGACA-GTCCTTGTACACTGTGGGGGAGCTGTT |
| ..C......C...G..............TT.CA.......G.............A........ |
| A.C..................................................... |
| ..C...........G.............TT.CA.......G............--------- |
| ..C...........G.............TT.CA...................--------- |
| ..C...........G.............GT.CA.......G............A........ |
| ..C...........G.............TT.CA.............................. |

Figure 11

```
   1 gtggttgtac agacgccatc ttggaatcca atatgtctgc cggctcagtc atgcctgcgc
  61 tgcgcgcagc gcgctgcgcg cgcgcatgat ctaatcgccg gcagacatat tggattccaa
 121 gatggcgtct gtacaaccac gtcacatata aataataaaa tattcacaag gaggagtggt
 181 tatatgatgt aatccataac cactcccagg aaatgacgta tgatagccaa tcagaattga
 241 gtattaaacc tatataagct gctgcacttc ctgattcaat cagactgcat ccggtctccg
 301 gcgagtgaac atctctggaa aaagctccac gcttgtggtg agtctactat ggctttcaat
 361 cctcctgtga ttagagcttt ttctcaacct gcttttactt atgtcttcaa atttccatat
 421 ccacaatgga aagaaaaaga atggctgctt catgcacttt tagctcatgg aactgaacaa
 481 tctatgatac aattaagaaa ctgcgctcct catccggatg aagacataat ccgtgatgac
 541 ttgcttattt ctttagaaga tcgccatttt ggggctgttc tctgcaaggc tgtttacatg
 601 gcaacaacta ctctcatgtc acacaaacaa aggaatatgt ttcctcgttg tgacatcata
 661 gttcagtctg agctaggaga gaaaaactta cactgccata ttatagttgg gggagaagga
 721 ctaagcaaga ggaatgctaa atcatcctgt gctcagttct atggtttaat actagctgaa
 781 ataattcaac gctgcaaatc tcttctggct acacgtcctt ttgaacctga agaggctgac
 841 atatttcaca ctttaaaaaa ggctgagcga gaggcatggg gtggagttac tggcggcaac
 901 atgcaaatcc ttcaatatag agatcgcaga ggagaccttc atgcacaaac agtggatcct
 961 cttcgcttct tcaaaaacta ccttttacct aaaaatagat gtatttcatc ttacagcaaa
1021 cctgatgttt gtacttctcc tgacaactgg ttcatttag ctgaaaaaac ttactctcac
1081 actcttatta cgggctgcc gcttccagaa cattacagaa aaaactacca cgcaacccta
1141 gataacgaag tcattccagg gcctcaaaca atggcctatg gaggacgtgg tccgtgggaa
1201 catcttcctg aggtaggaga tcagcgccta gctgcgtctt ctgttagcac tacttataaa
1261 cctaacaaaa aagaaaaact tatgctaaac ttgctagaca aatgtaaaga gctaaatcta
1321 ttagtttatg aagacttagt agctaattgt cctgaactac tccttatgct tgaaggtcaa
1381 ccaggagggg cacgccttat agaacaagtc ttgggcatgc accatattaa tgtttgttct
1441 aactttacag ctctcacata tctttttcat ctacatcctg ttacttcgct tgactcagac
1501 aataaagctt tacagctttt gttgattcaa ggctataatc ctctagccgt tggtcacgcc
1561 ctatgctgtg tcctgaacaa acaattcggg aaacaaaaca ctgtttgctt ttacgggcct
1621 gcctcaacag gtaaaacaaa tatggccaag gcaatcgtcc aagggattag actttatggg
1681 tgtgttaatc atttgaacaa aggatttgta tttaatgact gcagacaacg cctagttgtt
1741 tggtgggagg agtgcttaat gcaccaggat tgggtggaac ctgcaaagtg tatcttgggc
1801 gggacagaat gcagaattga cgtcaagcat agagacagtg tacttttaac tcaaacacct
1861 gtaattatat ccactaacca cgatatctac gcggttgttg gtggcaattc tgtttctcat
1921 gttcacgcgg ctccattaaa agaaagagtg attcagctaa atttatgaa acaacttcct
1981 caaacatttg gagaaatcac tgctactgag attgcagctc ttctacagtg gtgtttcaat
2041 gagtacgact gtactctgac aggatttaaa caaaatgga atttagataa aattccaaac
2101 tcatttcctc ttggggtcct ttgtcctact cattcacagg actttacact tcacgaaaac
2161 ggatactgca ctgattgcgg tggttacctt cctcatagtg ctgacaattc tatgtacact
2221 gatcgcgcaa gcgaaactag cacaggagac atcacaccaa gtaagtaaat acgcatgcgc
2281 aagtaattct tttactttca cttcgctatt tttaccaatt tttactttta ggtgacttgg
2341 gggattcgga cggagaagac accaagcctg agacatcgca agtggactat tgtccaccca
2401 agaaacgtcg tctaactgct ccagcaagtc ctccaaactc acctgcgagc tctgtaagta
2461 ctattacttt ctttaacact tggcacgcac agccacgtga cgaagatgag ctcagggaat
2521 atgaaagaca agcatcgctc ctacaaaaga aagggagtc cagaaagagg ggagaggaag
```

Figure 14

2581 agacactggc agacaactca tcacaggagc aggagccgca gcccgatccg acacagtggg
2641 gagagaggct cgggctcata tcatcaggaa cacccaatca gccacctatc gtcttgcact
2701 gcttcgaaga cctcagacca agtgatgaag acgagggaga gtacatcggg gaaaaaagac
2761 aatagaacaa atccatacac tgtattcagt caacacagag cttccaatcc tgaagctcca
2821 gggtggtgtg ggttctactg gcactctact cgcattgcta gagatggtac taattcaatc
2881 tttaatgaaa tgaaacaaca gtttcaacag ctacaaattg ataataaaat aggatgggat
2941 aacactagag aactattgtt taatcaaaag aaaacactag atcaaaaata cagaaatatg
3001 ttctggcact ttagaaataa ctctgattgt gaaagatgta attactggga tgatgtgtac
3061 cgtagacact tagctaatgt ttcctcacag acagaagcag acgagataac tgacgaggaa
3121 atgctttctg ctgctgaaag catggaagca gatgcctcca attaagagac agcctagagg
3181 gtgggtgctg cctggataca gatatcttgg gccatttaat ccacttgata acggtgaacc
3241 tgtaaataac gctgatcgcg ctgctcaatt acatgatcac gcctactctg aactaataaa
3301 gagtggtaaa aatccatacc tgtatttcaa taaagctgat gaaaaattca ttgatgatct
3361 aaaagacgat tggtcaattg gtggaattat tggatccagt ttttttaaaa taaagcgcgc
3421 cgtggctcct gctctgggaa ataaagagag agcccaaaaa agacacttttt actttgctaa
3481 ctcaaataaa ggtgcaaaaa aaacaaaaaa aagtgaacct aaaccaggaa cctcaaaaat
3541 gtctgacact gacattcaag accaacaacc tgatactgta gacgcaccac agaacacctc
3601 aggggagga acaggaagta ttggaggagg aaaaggatct ggtgtgggga tttccactgg
3661 agggtgggtc ggaggttctc acttttcaga caaatatgtg gttactaaaa acacaagaca
3721 atttataacc acaattcaga atggtcacct ctacaaaaca gaggccattg aaacaacaaa
3781 ccaaagtgga aaatcacagc gctgcgtcac aactccatgg acatacttta actttaatca
3841 atacagctgt cacttctcac cacaggattg gcagcgcctt acaaatgaat ataagcgctt
3901 cagacctaaa gcaatgcaag taaagattta caacttgcaa ataaaacaaa tactttcaaa
3961 tggtgctgac acaacataca acaatgacct cacagctggc gttcacatct tttgtgatgg
4021 agagcatgct tacccaaatg catctcatcc atgggatgag gacgtcatgc ctgatcttcc
4081 atacaagacc tggaaacttt tcaatatgg atatattcct attgaaaatg aactcgcaga
4141 tcttgatgga aatgcagctg gaggcaatgc tacagaaaaa gcacttctgt atcagatgcc
4201 ttttttttcta cttgaaaaca gtgaccacca agtacttaga actggtgaga gcactgaatt
4261 tactttttaac tttgactgtg aatgggttaa caatgaaaga gcatacattc ctcctggact
4321 aatgtttaat ccaaaagttc caacaagaag agttcagtac ataagacaaa acggaagcac
4381 agcagccagc acaggcagaa ttcagccata ctcaaaacca acaagctgga tgacaggacc
4441 tggcctgctc agtgcacaga gagtaggacc acagtcatca gacactgctc cattcatggt
4501 ttgcactaac ccagaaggaa cacacataaa cacaggtgct gcaggatttg gatctggctt
4561 tgatcctcca agcggatgtc tggcaccaac taacctagaa tacaaacttc agtggtacca
4621 gacaccagaa ggaacaggaa ataatggaaa cataattgca aacccatcac tctcaatgct
4681 tagagaccaa ctcctataca aaggaaacca gaccacatac aatctagtgg gggacatatg
4741 gatgtttcca aatcaagtct gggacagatt tcctatcacc agagaaaatc caatctggtg
4801 caaaaaacca agagctgaca aacacacaat catggatcca tttgatggat caattgcaat
4861 ggatcatcct ccaggcacta tttttataaa aatggcaaaa attccagttc caactgcctc
4921 aaatgcagac tcatacctaa acatatactg tactggacaa gtcagctgtg agattgtatg
4981 ggaagtaaaa agatacgcaa caagaactg gcgtccagaa agaagacata ctgcactcgg
5041 gatgtcactg ggaggagaaa gcaactacac gcctacatac cacgtggatc caacaggagc
5101 atacatccag cccacgtcat atgatcaatg tatgccagta aaaacaaaca tcaataaagt

Figure 14 (cont.)

5161 gttgtaatct tataagcctc tttttgctt ctgcttacaa gttcctcctc aatggacaag
5221 cggaaagtga agggtgactg tagtcctgag ctcatgggtt caagaccaca gcccgatggt
5281 agtggtgtta ccgtctcgaa cctagccgac agcccttgta cattgtgggg ggagctgttt
5341 tgtttgctta tgcaatcgcg aaactctata tcttttaatg tgttgttgtt gtacatgcgc
5401 catcttagtt ttatatcagc tggcgcctta gttatataac atgcatgtta tataactaag
5461 gcgccagctg atataaaact aagatggcgc atgtacaaca acaacacatt aaaagatata
5521 gagtttcgcg attgcataag caa

SEQ ID NO:25

Figure 14 (cont.)

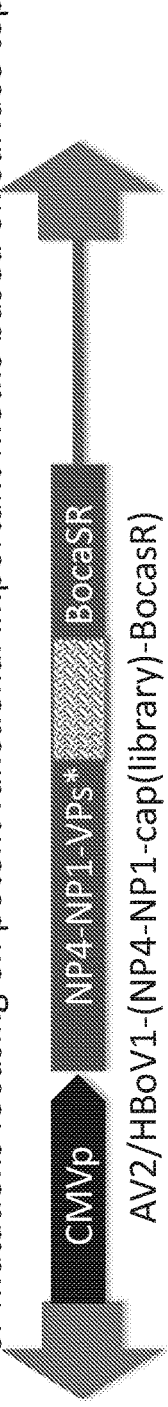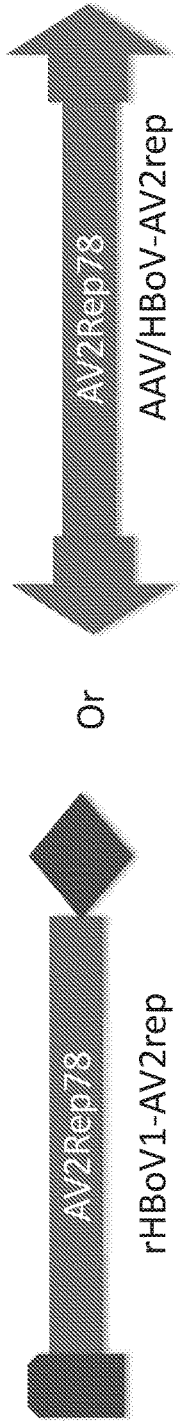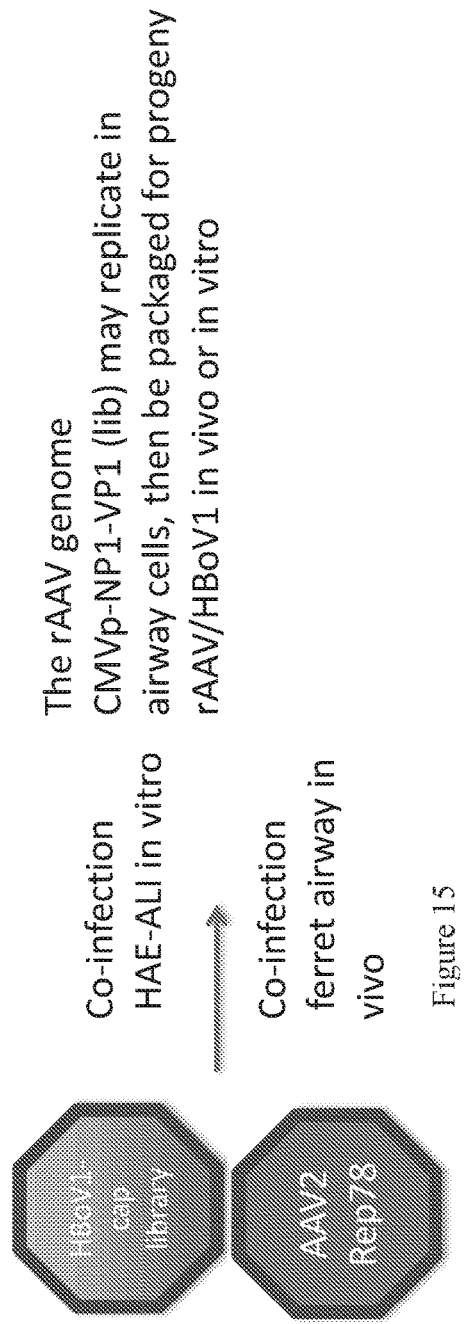
Figure 15

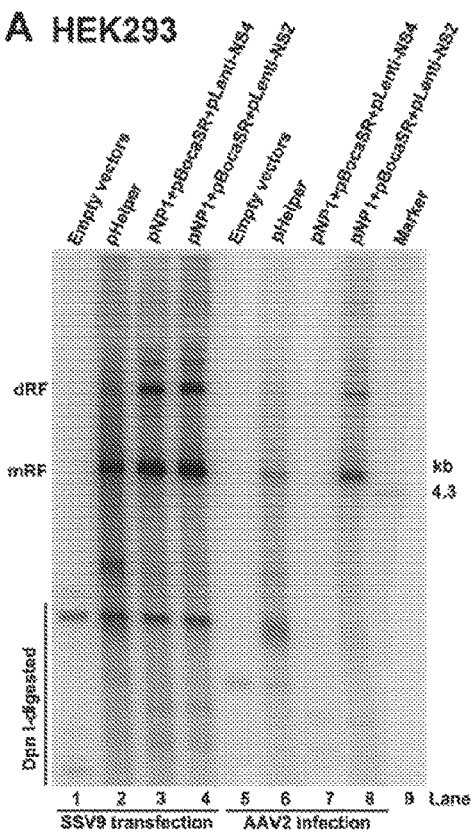
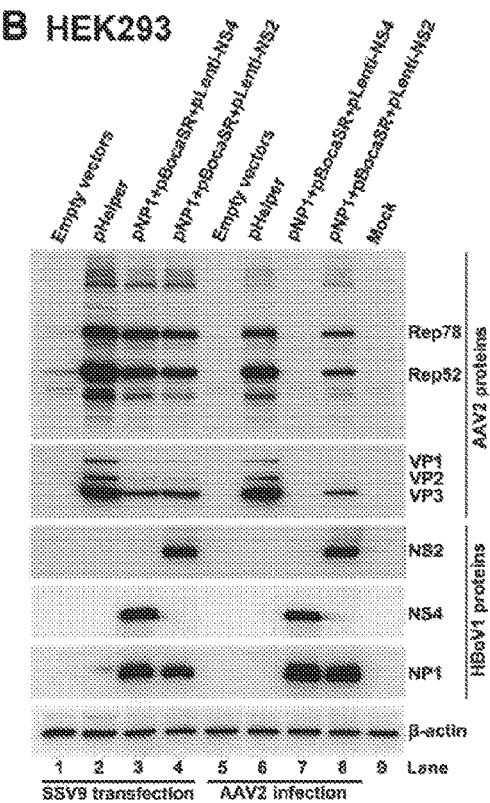
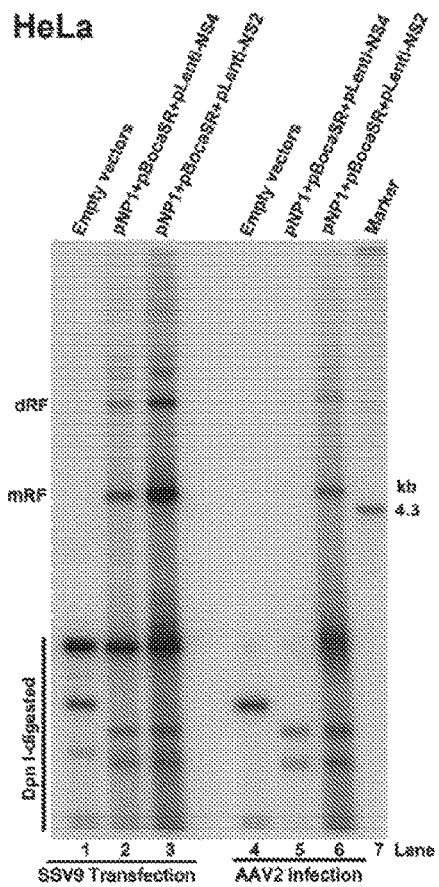
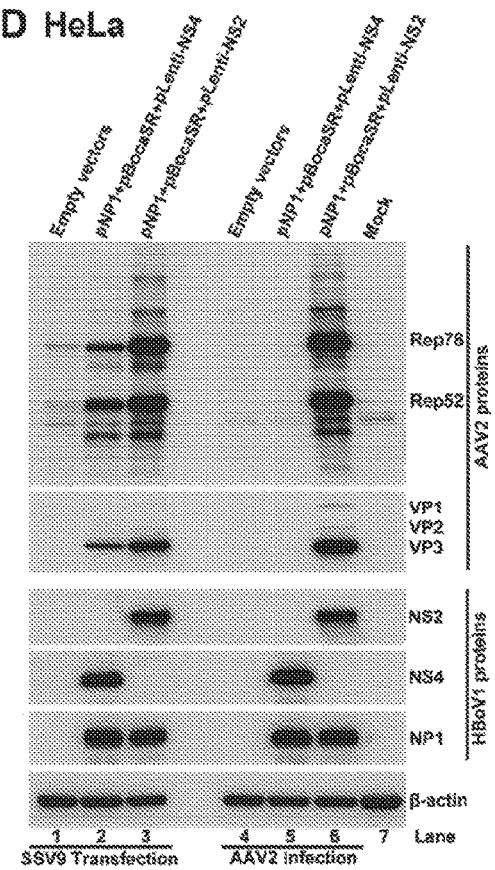
Figure 22

SEQUENCE LISTING

```
<160> NUMBER OF SEQ ID NOS: 30

<210> SEQ ID NO 1
<211> LENGTH: 141
<212> TYPE: DNA
<213> ORGANISM: Bocaparvo virus

<400> SEQUENCE: 1
```
aagttcctcc tcaatggaca agcggaaagt gaagggtgac tgtagtcctg agctcatggg    60
ttcaagacca cagcccgatg gtagtggtgt taccgtctcg aacctagccg acagcccttg   120
tacattgtgg ggggagctgt t                                             141

<210> SEQ ID NO 2
<211> LENGTH: 58
<212> TYPE: DNA
<213> ORGANISM: Artificial Sequence
<220> FEATURE:
<223> OTHER INFORMATION: A synthetic nucleotide sequence

<400> SEQUENCE: 2
ccgggctgaa cttcttcatg tatgtctcga gacatacatg aagaagttca gcttttttg    58

<210> SEQ ID NO 3
<211> LENGTH: 57
<212> TYPE: DNA
<213> ORGANISM: Artificial Sequence
<220> FEATURE:
<223> OTHER INFORMATION: A synthetic nucleotide sequence

<400> SEQUENCE: 3
ccggcctaag gttaagtcgc cctcgctcga gcgagggcga cttaacctta ggttttt      57

<210> SEQ ID NO 4
<211> LENGTH: 20
<212> TYPE: DNA
<213> ORGANISM: Artificial Sequence
<220> FEATURE:
<223> OTHER INFORMATION: A synthetic nucleotide sequence

<400> SEQUENCE: 4
taatacgact cactataggg                                                20

<210> SEQ ID NO 5
<211> LENGTH: 19
<212> TYPE: DNA
<213> ORGANISM: Artificial Sequence
<220> FEATURE:
<223> OTHER INFORMATION: A synthetic nucleotide sequence

<400> SEQUENCE: 5
tacagtcacc cttcactttt                                                19

<210> SEQ ID NO 6
<211> LENGTH: 19
<212> TYPE: DNA
<213> ORGANISM: Artificial Sequence
<220> FEATURE:
<223> OTHER INFORMATION: A synthetic nucleotide sequence

<400> SEQUENCE: 6
taacaccact accatcggg                                                 19

<210> SEQ ID NO 7
<211> LENGTH: 19
<212> TYPE: DNA
<213> ORGANISM: Artificial Sequence
<220> FEATURE:
<223> OTHER INFORMATION: A synthetic nucleotide sequence

<400> SEQUENCE: 7
tgtcggctag gttcgagac                                                 19

<210> SEQ ID NO 8
<211> LENGTH: 19
<212> TYPE: DNA
<213> ORGANISM: Artificial Sequence
<220> FEATURE:
<223> OTHER INFORMATION: A synthetic nucleotide sequence

<400> SEQUENCE: 8 tcccccaca atgtacaag                                                      19

<210> SEQ ID NO 9
<211> LENGTH: 25
<212> TYPE: DNA
<213> ORGANISM: Artificial Sequence
<220> FEATURE:
<223> OTHER INFORMATION: A synthetic nucleotide sequence

<400> SEQUENCE: 9
caagggctgt cggctaggtt cgaga                                              25

<210> SEQ ID NO 10
<211> LENGTH: 38
<212> TYPE: DNA
<213> ORGANISM: Artificial Sequence
<220> FEATURE:
<223> OTHER INFORMATION: A synthetic nucleotide sequence

<400> SEQUENCE: 10
ggccacgcgt cgactagtac tttttttttt ttttttv                                 38

<210> SEQ ID NO 11
<211> LENGTH: 25
<212> TYPE: DNA
<213> ORGANISM: Artificial Sequence
<220> FEATURE:
<223> OTHER INFORMATION: A synthetic nucleotide sequence

<400> SEQUENCE: 11
cgagacggta acaccactac catcg                                              25

<210> SEQ ID NO 12
<211> LENGTH: 20
<212> TYPE: DNA
<213> ORGANISM: Artificial Sequence
<220> FEATURE:
<223> OTHER INFORMATION: A synthetic nucleotide sequence

<400> SEQUENCE: 12
ggccacgcgt cgactagtac                                                    20

<210> SEQ ID NO 13
<211> LENGTH: 25
<212> TYPE: DNA
<213> ORGANISM: Artificial Sequence
<220> FEATURE:
<223> OTHER INFORMATION: A synthetic nucleotide sequence

<400> SEQUENCE: 13
catcgggctg tggtcttgaa cccat                                              25

<210> SEQ ID NO 14
<211> LENGTH: 17
<212> TYPE: DNA
<213> ORGANISM: Artificial Sequence
<220> FEATURE:
<223> OTHER INFORMATION: A synthetic nucleotide sequence

<400> SEQUENCE: 14
ctgtaggcac catcaat                                                    17

<210> SEQ ID NO 15
<211> LENGTH: 17
<212> TYPE: DNA
<213> ORGANISM: Artificial Sequence
<220> FEATURE:
<223> OTHER INFORMATION: A synthetic nucleotide sequence

<400> SEQUENCE: 15
attgatggtg cctacag                                                    17

<210> SEQ ID NO 16
<211> LENGTH: 25
<212> TYPE: DNA
<213> ORGANISM: Artificial Sequence
<220> FEATURE:
<223> OTHER INFORMATION: A synthetic nucleotide sequence

<400> SEQUENCE: 16
gtgaagggtg actgtagtcc tgagc                                           25

<210> SEQ ID NO 17
<211> LENGTH: 162
<212> TYPE: DNA
<213> ORGANISM: Adeno virus

<400> SEQUENCE: 17
gggcactctt ccgtggtctg gtggataaat tcgcaagggt atcatggcgg acgaccgggg     60
ttcgagcccc gtatccggcc gtccgccgtg atccatgcgg ttaccgcccg cgtgtcgaac    120
ccaggtgtgc gacgtcagac aacggggag agtgctcctt tt                        162

<210> SEQ ID NO 18
<211> LENGTH: 131
<212> TYPE: DNA
<213> ORGANISM: Bocaparvo virus

<400> SEQUENCE: 18
aagttcctct ccaatggaca agaggaaaga aaagggtgac tgtaatcccg agctcatgag     60
ttcgaggcta cagtccgatg gcagtggtgt tgccgtctcg aacctagccg ttacacccctt   120 gtgcattgtg g                                                         131

<210> SEQ ID NO 19
<211> LENGTH: 117
<212> TYPE: DNA
<213> ORGANISM: Bocaparvo virus

<400> SEQUENCE: 19
aagttcctct ccaatggaca agtggaaaga aaagggtgac tgtaatcccg agctcataag     60
ttcgaggcta cagtccgatg gcagtggtgt tgccgtctcg aacctagccg ttacacc       117

<210> SEQ ID NO 20
<211> LENGTH: 141
<212> TYPE: DNA
<213> ORGANISM: Bocaparvo virus

<400> SEQUENCE: 20
aagttcctct ccaatggaca agaggaaaga aaagggtgac tgtaatcccg agctcatgag     60

```
ttcgaggcta cagtccgatg gcagtggtgt tgccgtctcg aacctagccg gtacaccctt    120
gtgcattgtg ggggagctgt t                                              141
```

<210> SEQ ID NO 21
<211> LENGTH: 117
<212> TYPE: DNA
<213> ORGANISM: Bocaparvo virus

<400> SEQUENCE: 21

```
aagttcctct ccaatggaca gtggaaaga aagggtgac tgtaatcccg agctcatgag     60
ttcgaggcta cagtccgatg gcagtggtgt tgccgtctcg aacctagccg ttacacc      117
```

<210> SEQ ID NO 22
<211> LENGTH: 83
<212> TYPE: DNA
<213> ORGANISM: Bocaparvo virus

<400> SEQUENCE: 22

```
aagttcccctt ccaatggaca gtggataga aaggggtgac tgtaatcccg agctcatgag    60
ttcgaggcta cagtccgata gca                                            83
```

<210> SEQ ID NO 23
<211> LENGTH: 141
<212> TYPE: DNA
<213> ORGANISM: Bocaparvo virus

<400> SEQUENCE: 23

```
aagttcctct ccaatggaca gtggaaaga aagggtgac tgtaatcccg agctcatgag     60
ttcgaggcta cagtccgatg gcagtggcgt tgccgtctcg aacctagccg atacaccctt   120
gtgcattgtg ggggagctgt t                                              141
```

<210> SEQ ID NO 24
<211> LENGTH: 143
<212> TYPE: DNA
<213> ORGANISM: Bocaparvo virus

<400> SEQUENCE: 24

```
aagttcctcc tcaatggaca agcggaaagt gaagggtgac tgtagtcctg agctcatggg    60
ttcaagacca cagcccgatg gtagtggtgt taccgtctcg aacctagccg acagcccttg   120
tacattgtgg ggggagctgt ttt                                            143
```

<210> SEQ ID NO 25
<211> LENGTH: 5543
<212> TYPE: DNA
<213> ORGANISM: Bocaparvo virus

<400> SEQUENCE: 25

```
gtggttgtac agacgccatc ttggaatcca atatgtctgc cggctcagtc atgcctgcgc    60
tgcgcgcagc gcgctgcgcg cgcgcatgat ctaatcgccg gcagacatat tggattccaa   120
gatggcgtct gtacaaccac gtcacatata aaataataaa tattcacaag gaggagtggt   180
tatatgatgt aatccataac cactcccagg aaatgacgta tgatagccaa tcagaattga   240
gtattaaacc tatataagct gctgcacttc ctgattcaat cagactgcat ccggtctccg   300
gcgagtgaac atctctggaa aaagctccac gcttgtggtg agtctactat ggctttcaat   360
cctcctgtga ttagagcttt ttctcaacct gcttttactt atgtcttcaa atttccatat   420
ccacaatgga agaaaaaga atggctgctt catgcacttt tagctcatgg aactgaacaa   480
```

```
tctatgatac aattaagaaa ctgcgctcct catccggatg aagacataat ccgtgatgac    540
ttgcttattt ctttagaaga tcgccatttt ggggctgttc tctgcaaggc tgtttacatg    600
gcaacaacta ctctcatgtc acacaaacaa aggaatatgt ttcctcgttg tgacatcata    660
gttcagtctg agctaggaga gaaaaactta cactgccata ttatagttgg gggagaagga    720
ctaagcaaga ggaatgctaa atcatcctgt gctcagttct atggtttaat actagctgaa    780
ataattcaac gctgcaaatc tcttctggct acacgtcctt tgaacctga agaggctgac    840
atatttcaca cttaaaaaa ggctgagcga gaggcatggg gtggagttac tggcggcaac    900
atgcaaatcc ttcaatatag agatcgcaga ggagaccttc atgcacaaac agtggatcct    960
cttcgcttct tcaaaaacta cctttacct aaaatagat gtatttcatc ttacagcaaa     1020
cctgatgttt gtacttctcc tgacaactgg ttcattttag ctgaaaaaac ttactctcac    1080
actcttatta acgggctgcc gcttccagaa cattacagaa aaactacca cgcaacccta     1140
gataacgaag tcattccagg gcctcaaaca atggcctatg aggacgtgg tccgtgggaa     1200
catcttcctg aggtaggaga tcagcgccta gctgcgtctt ctgttagcac tacttataaa    1260
cctaacaaaa agaaaaaact tatgctaaac ttgctagaca aatgtaaaga gctaaatcta    1320
ttagtttatg aagacttagt agctaattgt cctgaactac tccttatgct tgaaggtcaa    1380
ccaggagggg cacgccttat agaacaagtc ttgggcatgc accatattaa tgttgttct     1440
aactttacag ctctcacata tcttttcat ctacatcctg ttacttcgct tgactcagac    1500
aataaagctt tacagctttt gttgattcaa ggctataatc tctagccgt tggtcacgcc     1560
ctatgctgtg tcctgaacaa acaattcggg aaacaaaaca ctgtttgctt ttacgggcct    1620
gcctcaacag gtaaaacaaa tatggccaag gcaatcgtcc aagggattag acttatggg     1680
tgtgttaatc atttgaacaa aggatttgta tttaatgact gcagacaacg cctagttgtt    1740
tggtgggagg agtgcttaat gcaccaggat tgggtggaac ctgcaaagtg tatcttgggc    1800
gggacagaat gcagaattga cgtcaagcat agagacagtg tacttttaac tcaaacacct    1860
gtaattatat ccactaacca cgatatctac gcggttgttg gtggcaattc tgtttctcat    1920
gttcacgcgg ctccattaaa agaaagagtg attcagctaa atttatgaa caacttcct     1980
caaacatttg gagaaatcac tgctactgag attgcagctc ttctacagtg gtgtttcaat    2040
gagtacgact gtactctgac aggatttaaa caaaaatgga atttagataa aattccaaac    2100
tcatttcctc ttggggtcct ttgtcctact cattcacagg actttacact tcacgaaaac    2160
ggatactgca ctgattgcgg tggttacctt cctcatagtg ctgacaattc tatgtacact    2220
gatcgcgcaa gcgaaactag cacaggagac atcacaccaa gtaagtaaat acgcatgcgc    2280
aagtaattct tttactttca cttcgctatt tttaccaatt tttactttta ggtgacttgg    2340
gggattcgga cggagaagac accaagcctg agacatcgca agtggactat tgtccaccca    2400
agaaacgtcg tctaactgct ccagcaagtc ctccaaactc acctgcgagc tctgtaagta    2460
ctattacttt ctttaacact tggcacgcac agccacgtga cgaagatgag ctcagggaat    2520
atgaaagaca agcatcgctc ctacaaaaga aagggagtc cagaaagagg ggagaggaag     2580
agacactggc agacaactca tcacaggagc aggagccgca gcccgatccg acacagtggg    2640
gagagaggct cgggctcata tcatcaggaa cacccaatca gccacctatc gtcttgcact    2700
gcttcgaaga cctcagacca agtgatgaag acgagggaga gtacatcggg gaaaaaagac    2760
aatagaacaa atccatacac tgtattcagt caacacagag cttccaatcc tgaagctcca    2820
```

```
gggtggtgtg ggttctactg gcactctact cgcattgcta gagatggtac taattcaatc    2880
tttaatgaaa tgaaacaaca gtttcaacag ctacaaattg ataataaaat aggatgggat    2940
aacactagag aactattgtt taatcaaaag aaaacactag atcaaaaata cagaaatatg    3000
ttctggcact ttagaaataa ctctgattgt gaaagatgta attactggga tgatgtgtac    3060
cgtagacact tagctaatgt ttcctcacag acagaagcag acgagataac tgacgaggaa    3120
atgctttctg ctgctgaaag catggaagca gatgcctcca attaagagac agcctagagg    3180
gtgggtgctg cctggataca gatatcttgg gccatttaat ccacttgata acggtgaacc    3240
tgtaaataac gctgatcgcg ctgctcaatt acatgatcac gcctactctg aactaataaa    3300
gagtggtaaa aatccatacc tgtatttcaa taaagctgat gaaaaattca ttgatgatct    3360
aaaagacgat tggtcaattg gtggaattat tggatccagt tttttttaaaa taaagcgcgc    3420 cgtggctcct gctctgggaa ataaagagag agcccaaaaa agacactttt actttgctaa    3480
ctcaaataaa ggtgcaaaaa aaacaaaaaa aagtgaacct aaaccaggaa cctcaaaaat    3540
gtctgacact gacattcaag accaacaacc tgatactgta gacgcaccac agaacacctc    3600
agggggagga acaggaagta ttggaggagg aaaaggatct ggtgtgggga tttccactgg    3660
agggtgggtc ggaggttctc acttttcaga caaatatgtg gttactaaaa acacaagaca    3720
atttataacc acaattcaga atggtcacct ctacaaaaca gaggccattg aaacaacaaa    3780
ccaaagtgga aaatcacagc gctgcgtcac aactccatgg acatacttta actttaatca    3840
atacagctgt cacttctcac cacaggattg gcagcgcctt acaaatgaat ataagcgctt    3900
cagacctaaa gcaatgcaag taagagattta caacttgcaa ataaaacaaa tactttcaaa    3960
tggtgctgac acaacataca acaatgacct cacagctggc gttcacatct tttgtgatgg    4020
agagcatgct tacccaaatg catctcatcc atgggatgag gacgtcatgc ctgatcttcc    4080
atacaagacc tggaaacttt ttcaatatgg atatattcct attgaaaatg aactcgcaga    4140
tcttgatgga aatgcagctg gaggcaatgc tacagaaaaa gcacttctgt atcagatgcc    4200 ttttttttcta cttgaaaaca gtgaccacca agtacttaga actggtgaga gcactgaatt    4260 tactttaac tttgactgtg aatgggttaa caatgaaaga gcatacattc ctcctggact    4320
aatgtttaat ccaaaagttc aacaagaag agttcagtac ataagacaaa acggaagcac    4380
agcagccagc acaggcagaa ttcagccata ctcaaaacca acaagctgga tgacaggacc    4440
tggcctgctc agtgcacaga gagtaggacc acagtcatca gacactgctc cattcatggt    4500
ttgcactaac ccagaaggaa cacacataaa cacaggtgct gcaggatttg atctggctt    4560 tgatcctcca agcggatgtc tggcaccaac taacctagaa tacaaacttc agtggtacca    4620
gacaccagaa ggaacaggaa ataatggaaa cataattgca aacccatcac tctcaatgct    4680
tagagaccaa ctcctataca aggaaaccaa gaccacatac aatctagtgg gggacatatg    4740
gatgtttcca aatcaagtct gggacagatt tcctatcacc agagaaaatc caatctggtg    4800
caaaaaacca agagctgaca aacacacaat catggatcca tttgatggat caattgcaat    4860
ggatcatcct ccaggcacta ttttttataaa aatggcaaaa attccagttc aactgcctc    4920 aaatgcagac tcatacctaa acatatactg tactggacaa gtcagctgtg agattgtatg    4980
ggaagtaaaa agatacgcaa caaagaactg gcgtccagaa agaagacata ctgcactcgg    5040
gatgtcactg ggaggagaaa gcaactacac gcctacatac cacgtggatc caacaggagc    5100
atacatccag cccacgtcat atgatcaatg tatgccagta aaaacaaaca tcaataaagt    5160
gttgtaatct tataagcctc ttttttgctt ctgcttacaa gttcctcctc aatggacaag    5220
```

```
cggaaagtga agggtgactg tagtcctgag ctcatgggtt caagaccaca gcccgatggt    5280
agtggtgtta ccgtctcgaa cctagccgac agcccttgta cattgtgggg ggagctgttt    5340
tgtttgctta tgcaatcgcg aaactctata tcttttaatg tgttgttgtt gtacatgcgc    5400
catcttagtt ttatatcagc tggcgcctta gttatataac atgcatgtta tataactaag    5460
gcgccagctg atataaaact aagatggcgc atgtacaaca acaacacatt aaaagatata    5520
gagtttcgcg attgcataag caa                                             5543

<210> SEQ ID NO 26
<211> LENGTH: 138
<212> TYPE: RNA
<213> ORGANISM: Bocaparvo virus

<400> SEQUENCE: 26
aaguuccucc ucaauggaca agcggaaagu gaagggugac uguaguccug agcucauggg    60
uucaagacca cagcccgaug guaguggugu uccgucucga acuagccgac agcccuugua    120 cauuguggg ggagcugu                                                    138

<210> SEQ ID NO 27
<211> LENGTH: 19
<212> TYPE: DNA
<213> ORGANISM: Artificial Sequence
<220> FEATURE:
<223> OTHER INFORMATION: A synthetic nucleotide sequence

<400> SEQUENCE: 27
tctgcagctc ccactcgat                                                  19

<210> SEQ ID NO 28
<211> LENGTH: 25
<212> TYPE: DNA
<213> ORGANISM: Artificial Sequence
<220> FEATURE:
<223> OTHER INFORMATION: A synthetic nucleotide sequence

<400> SEQUENCE: 28
tttgcttcct tcatcacaca gtact                                           25

<210> SEQ ID NO 29
<211> LENGTH: 11
<212> TYPE: DNA
<213> ORGANISM: Artificial Sequence
<220> FEATURE:
<223> OTHER INFORMATION: A synthetic nucleotide sequence

<400> SEQUENCE: 29
accgtgtccc g                                                          11

<210> SEQ ID NO 30
<211> LENGTH: 12
<212> TYPE: DNA
<213> ORGANISM: Artificial Sequence
<220> FEATURE:
<223> OTHER INFORMATION: A synthetic nucleotide sequence
<221> NAME/KEY: misc_feature
<222> LOCATION: (1)...(12)
<223> OTHER INFORMATION: n = T, C or G

<400> SEQUENCE: 30
nnnnnnnnnn nn                                                         12
```

US 11,142,775 B2

BOCAPARVOVIRUS SMALL NONCODING RNA AND USES THEREOF

CROSS-REFERENCE TO RELATED APPLICATIONS

This application is a U.S. National Stage Filing under 35 U.S.C. 371 from International Application No. PCT/US2018/013634, filed on Jan. 12, 2018, and published as WO 2018/132747 on Jul. 19, 2018, which application claims the benefit of the filing date of U.S. application Ser. No. 62/445,987, filed on Jan. 13, 2017, the disclosures of which are incorporated by reference herein.

STATEMENT OF GOVERNMENT RIGHTS

This invention was made with government support under AI070723, AI105543, AI112803, and GM103326 awarded by The National Institutes of Health. The government has certain rights in the invention.

BACKGROUND

Human bocavirus 1 (HBoV1), which was discovered in 2005 (Allander et al., 2005), belongs to the species *Primate bocaparvovirus* 1 in the genus *Bocaparvovirus* of the Parvoviridae family (Cotmore et al., 2014) (2). Increasing evidence suggests that HBoV1 is an etiological pathogen rather than a bystander in acute respiratory tract infections, especially in children under 5 years of age. Acute respiratory infections have been clearly linked to HBoV1 infection as assessed by mono-detection, high viral loads of $>10^4$ viral genomic copies per ml of respiratory specimens (Allander et al., 2007; Wang et al., 2010; Christensen et al., 2010; Deng et al., 2012; Briew et al., 2008; Zhou et al, 2014; Jiang et al., 2016; Ghletto et al., 2015; Ricart et al., 2013; Edner et al., 2011; Jula et al., 2013; Sadeghi et al., 2013; Nascrimento-Carvalho et al., 2012; Zhau et al., 2013), the presence of HBoV1-specific IgM, or a ≥4-fold increase in levels of HBoV1-specific IgG antibodies (Nascrimento-Carvalho et al., 2012; Soderlind-Venermo et al., Kantola et al., 2008; Don et al., 2010).

HBoV1 is a non-enveloped icosahedral virus with a linear single-stranded DNA (ssDNA) genome of 5.5 kilobases (kb) (Huang et al., 2012). Two terminal palindromic sequences, termed the left-end hairpin (LEH) and right-end hairpin (REH), respectively, correspond to the 3' and 5' ends of the negative-sense viral genome. The HBoV1 genome encodes two groups of genes: a set that expresses non-structural proteins, and another that expresses structural (capsid) proteins (VP). One unique feature of the bocaparvoviruses is the expression of an additional nonstructural protein, NP1, whose open reading frame (ORF) is located in the middle of the viral genome and overlaps with the C-terminus of the NS1 ORF but is in a different reading frame (Qiu et al., 2007; Sun et al., 2009). NS1, NS2, NS3, and NS4 are of about 100, about 66, about 69, and about 34 kDa, respectively, and share a common C-terminus (amino acids (aa) 639-781) (Shen et al., 2015). NS1, which has a putative DNA origin binding/endonuclease domain (OBD), a helicase activity domain, and a transactivation domain (TAD) within its N-terminal, middle, and C-terminal regions, respectively, is essential to replication of the viral DNA (Shen et al., 2015). NS2 contains the entire OBD and TAD domains of the NS1, whereas NS3 contains the helicase and TAD domains of NS1, and NS4 contains only the TAD domain. NS2-4 are not required for replication of the duplex viral genome (pIHBoV1) in HEK293 cells; however, NS2 plays an important role during infection of differentiated human airway epithelial cells (Shen et al., 2015). The functions of NS3 and NS4 are currently unknown. NP1, which is comprised of 219 aa, has a MW of 25 kDa. It plays important roles not only in replication of the viral DNA (Huang et al., 2012; Sun et al., 2009), but also in processing of the viral mRNA transcripts (Fasina et al., 2015; Zou et al., 2016). NP1 is required for the splicing of viral mRNAs, as well as for read-through from the proximal polyadenylation site (Zou et al., 2016). Therefore, NP1 is essential for both the generation of VP-encoding mRNAs and the production of viral capsid proteins.

The only in vitro system in which HBoV1 has been found to be capable of infection is differentiated (non-dividing) epithelial cells of the human airway epithelium (HAE) cultured at an air-liquid interface (HAE-ALI) (Huang et al., 2012; Dijkman et al., 2009; Deng et al., 2013; Deng et al., 2014; Deng et al., 2016). Neither dividing primary airway epithelial cells nor monolayer cultures of cell lines derived from the airway epithelium support significant HBoV1 infection or the replication of pIHBoV1 following transfection (Deng et al., 2016). However, HEK293 cells support the replication following transfection of pIHBoV1 plasmid containing the full-length duplex genome, as well as the generation of infectious progeny virions (Huang et al., 2012; Shen et al., 2015). During infection of non-dividing HAE cells, HBoV1 conscripts the cellular DNA damage and repair machinery to amplify the viral genome (Deng et al., 2016), making HBoV1 unique among autonomous parvoviruses in that its replication is cell cycle-independent (Berns et al., 2015).

Previously it was reported that replication of the duplex HBoV1 genome in HEK293 cells requires the presence of a replication origin (Ori) within the REH and the 3' end non-coding region (NCR), as well as the HBoV1 NS1 and NP1 proteins (Shen et al., 2016).

SUMMARY

Human Bocavirus 1 (HBoV1) belongs to species *Primate bocaparvovirus* of the genus *Bocaparvovirus* of the Parvoviridae family. HBoV1 causes acute respiratory tract infections in children and has a selective tropism for the apical surface of well-differentiated human airway epithelia (HAE). As described below, an additional HBoV1 gene was identified, bocavirus-transcribed small non-coding non-polyadenylated RNA (BocaSR), within the 3' non-coding region (nt 5199-5338) of the viral genome of positive sense. BocaSR is transcribed by RNA polymerase III (Pol III) from an intragenic promoter at similar levels to that of the VP-coding mRNA and was found to be essential for replication of the viral DNA in both transfected HEK293 and infected HAE cells, and for productive infection of HAE-ALI cultures by HBoV1. Mechanistically, BocaSR was found to regulate the expression of HBoV1-encoded non-structural proteins NS1, NS2, NS3, and NP1, but not N54. BocaSR is somewhat related to the adenovirus-associated type I (VAI) RNA in terms of both nucleotide sequence and secondary structure, but differs from it in that its regulation of viral protein expression is independent of RNA-activated protein kinase (PKR) regulation. Notably, BocaSR accumulates in the viral DNA replication centers within the nucleus and plays a direct role in replication of the viral DNA. BocaSR is thus a viral noncoding RNA that coordinates the expression of viral proteins and regulates replication of viral DNA within the nucleus. Accordingly, BocaSR may be used for anti-viral therapies for HBoV and may also have utility in the production of recombinant HBoV vectors.

A vector is provided vector that comprises a nucleotide sequence having SEQ ID NO:1 or a nucleotide sequence having at least 85%, 86%, 87%, 88%, 89%, 90%, 92%, 94%, 95%, 96%, 97%, 98%, 99% or more nucleotide sequence identity to SEQ ID NO:1 (corresponding to nucleotides 5199 to 5339 of SEQ ID NO:25), or a portion thereof that is capable of regulating bocaparvovirus replication, or the complement thereof, wherein the vector does not encode one or more BoV NS, VP or NP. For example, the vector may include a LEH, a 3' UTR and a REH, wherein the 3' UTR includes a nucleotide sequence having at least 85% identity to SEQ ID NO:1, or a portion thereof that is capable of regulating bocaparvovirus replication, wherein the REH includes a 46 nucleotide sequence comprising OriR having a TRS and a NS1 nicking or binding site, wherein the genome encodes bocavirus NP1 or NP2, NS3 or NS4, VP1, VP2 and/or VP3, or any combination thereof, so that bocavirus NS3 protein or NS4 protein, VP1 protein, VP2 protein or VP3 protein, NP1 protein, and a RNA having at least 85% identity to SEQ ID NO:1, or a portion thereof that is capable of regulating bocaparvovirus replication, but not NS1, are expressed from the vector. The vector may comprise a promoter operably linked to the nucleotide sequence. The vector may be a viral vector. The vector may be part of a liposome.

Also provided is a vector comprising a nucleic acid segment that is a complement to a nucleotide sequence having SEQ ID NO:1 or a nucleotide sequence having at least 85%, 86%, 87%, 88%, 89%, 90%, 92%, 94%, 95%, 96%, 97%, 98%, 99% or more nucleotide sequence identity to SEQ ID NO:1, or a portion thereof that inhibits expression of SEQ ID NO:1. The vector may include a promoter operably linked to the nucleic acid segment.

Further provided is a method to prevent, inhibit or treat bocaparvovirus infection in a mammal. The method includes administering to a mammal a composition comprising a vector comprising a nucleic acid segment that is a complement to a nucleotide sequence having SEQ ID NO:1 or a nucleotide sequence having at least 85%, 86%, 87%, 88%, 89%, 90%, 92%, 94%, 95%, 96%, 97%, 98%, 99% or more nucleotide sequence identity to SEQ ID NO:1, or a portion thereof that inhibits expression of SEQ ID NO:1. The composition may comprise a liposome comprising the vector, e.g., a neutral or cationic liposome, such as DOSPA/DOPE, DOGS/DOPE or DMRIE/DOPE liposomes. The composition may comprise a microparticle or nanoparticle comprising the vector. Exemplary diameters for particles include but are not limited to particles from about 25 nm to about 2,000 nm (i.e., 2 microns), from about 50 nm to about 1,900 nm, from about 75 nm to about 1,800 nm, from about 200 nm to about 800 nm, from about 500 nm about 700 nm, or less than about 600 nm, less than about 500 nm, less than about 400 nm, less than about 300 nm, less than about 250 nm, less than about 200 nm, less than about 150 nm, less than about 100 nm, less than about 75 nm, less than about 50 nm, or from about 1 µm to about 1,900 um, from about 20 um to about 1,800 um, from about 40 um to about 100 µm, from about 50 µm about 200 um, or less than about 60 µm, less than about 50 µm, less than about 40 µm. The composition may comprise a viral vector comprising the nucleic acid segment, e.g., an adenovirus, a parvovirus, such as adeno-associated virus (AAV), poxvirus, papillomavirus, lentivirus, herpesvirus, foamivirus or retrovirus vector.

An adenovirus helper-free method to produce recombinant adeno-associated virus (rAAV) is provided. The method includes contacting mammalian cells with a rAAV vector and a BoV vector that expresses BoV NP1, BoV NS3/4, e.g. NS4, or NS2 and a nucleotide sequence having SEQ ID NO:1 or a nucleotide sequence having at least 85% identity to SEQ ID NO:1, or a portion thereof that is capable of regulating bocaparvovirus replication, in an amount effective to yield rAAV; and isolating adenovirus-free rAAV from the cells. The cells or the rAAV express AAV Rep and/or Cap. For example, the rAAV may express AAV Rep and the cell may express AAV Cap. The cells may be human cells. The capsid protein may be from, for example, AAV-2, AAV-5, or AAV-9.

Further provided is a method to produce chimeric AAV/BoV. The method includes contacting mammalian cells with a rAAV vector and a BoV vector that expresses BoV NP1, BoV NS3/4, e.g., NS4, or NS2, BoV VP1, VP2 and/or VP3, and a nucleotide sequence having SEQ ID NO:1 or a nucleotide sequence having at least 85% identity to SEQ ID NO:1, or a portion thereof that is capable of regulating bocaparvovirus replication, in an amount effective to yield chimeric rAAV/BoV and isolating chimeric AAV/BoV. The AAV genome may comprise an expression cassette encoding a heterologous gene product including a therapeutic gene product or a viral, bacterial, tumor, parasite, or fungal antigen, or a heterologous nucleic acid sequence for homologous recombination with selected sequences in the genome of a mammal, e.g., the gene product may be cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, DNA endonuclease, zinc finger nuclease, a fusion protein including a DNA binding domain linked to a nuclease, or a cytokine, e.g., IFN-alpha, IFN-gamma, TNF, IL-1, IL-17, or IL-6.

BRIEF DESCRIPTION OF FIGURES

FIG. 11. Alignments of BocaSR coding sequences in primate bocaparvovirus 1 (SEQ ID NO:1) and 2. BocaSR-encoding sequences of the 3' NCR region of 7 isolates of primate bocaparvovirus, aligned using the CLUSTALW algorithm. Nucleotide identity is indicated by dots. The 3' end of the BocaSR sequences of HBoV2a (SEQ ID NO:18), b (SEQ ID NO:19), c (SEQ ID NO:20), HBoV4 (SEQ ID NO:21), GBoV1 (SEQ ID NO:22) and HboV3 (SEQ ID NO:23) are currently not available, and are indicated as grey lines. The Genbank accession number of each isolate is indicated. As noted, the full-length genome sequence is known only in the case of HBoV1. The A-box and B-box are marked, as is the tetranucleotide pair, GGGU:ACCU.

FIG. 14. Exemplary BoV sequence (SEQ ID NO:25).

FIG. 15. Schematic of directed capsid evolution using the vectors described herein. Vectors for BoV capsid evolution are depicted, however, AAV capsid genes may also be used.

FIGS. 18A-D. Identification of HBoV1 minimal helper genes for AAV2 DNA replication in HEK293 cells. HEK293 cells were transfected with an AAV2 infectious clone (SSV9) and Ad pHelper or pIHBoV1-based mutants (A&C), or with SSV9 and pCMV-HBoV1-based mutants (B&D), as indicated. (A&B) Southern blot analysis. At 48 h post-transfection, 90% of the collected cells were lysed for Hirt DNA extraction. Hirt DNA samples were digested with Dpn I and analyzed by Southern blotting with a $^{32}$P-labelled AAV2 probe, dRF and mRF DNAs, the 4.3 kb AAV2 marker, and Dpn I-digested (input) DNA are indicated. (C&D) Western blot analysis. At 48 h post-transfection, 10% of the collected cells were lysed and immunoblotted with anti-AAV2 Rep, anti-AAV2 VP, anti-HBoV1 NS1C, anti-HBoV1 VP3, anti-HBoV1 NP1, and anti-β-actin antibodies. Proteins detected are indicated next to the images.

FIGS. 19A-D AAV2 DNA replication, protein expression, and virus production in HEK293 cells co-transfected with different combinations of HBoV1 helper genes. HEK293 cells were transfected with an AAV2 infectious clone (SSV9) and various combinations of HBoV1 helper genes, as indicated. (A) Southern blot analysis. At 48 h post-transfection, 90% of the transfected cells were harvested for Hirt DNA extraction. Hirt DNA samples was examined for viral DNA replication by Southern blotting with a $^{32}$P-labelled AAV2 probe. dRF and mRF DNAs, Dpn I-digested DNA, and the 4.3 kb AAV2 marker are indicated. (B) Western blot analysis. At 48 h post-transfection, 10% of the transfected cells were collected, lysed, and immunoblotted with anti-AAV2 Rep, anti-AAV2 VP, anti-HBoV1 NS1C, anti-HBoV1 NP1, and anti-β-actin antibodies. Proteins detected are indicated. (C) AAV2 virus production. The transfected cells were collected, lysed, and quantified for DRP by real-time PCR. The virus production levels are shown as DRP/cell. Error bars shown standard deviations, which were obtained from three independent experiments. Statistical analysis was performed using Student "t" test. \*\*\*P<0.0001. (D) Infectivity of the progeny viruses. HEK293 were infected with Ad pHelper-produced AAV2 (AAV2$^{AdHelper}$) or with HBoV1 Helper-produced AAV2 (AAV2$^{BocaHelper}$) at an MOI of 300 DRP/cell, followed by transfection with Ad pHelper. At 48 h post-transfection, the cells were collected for analyzing virus production, as determined by real-time PCR. Error bars show standard deviations, which were obtained from three independent experiments. Statistical analysis was performed using Student "t" test. N.S., no significance.

Figure 20:
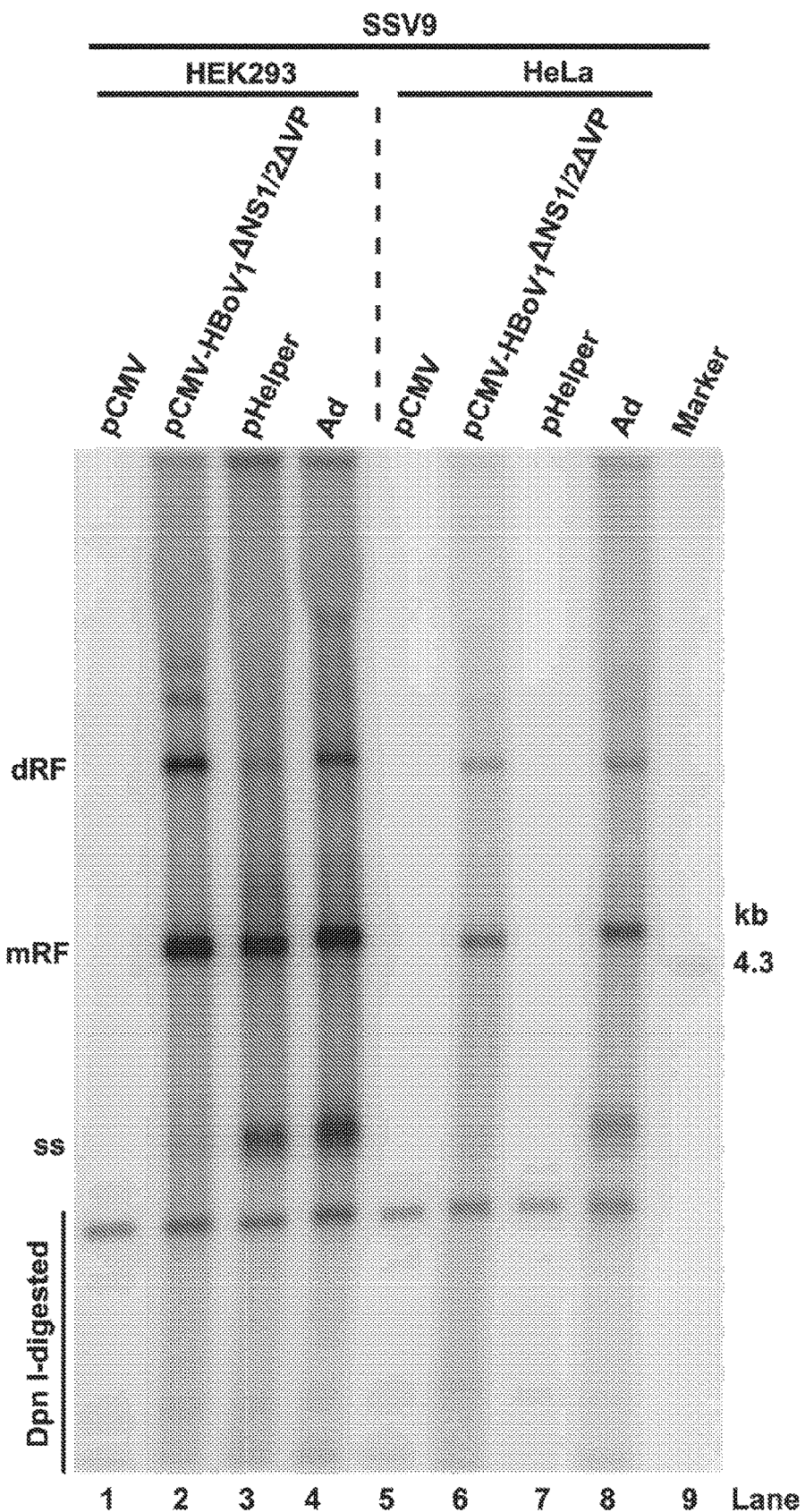
Figure 21:
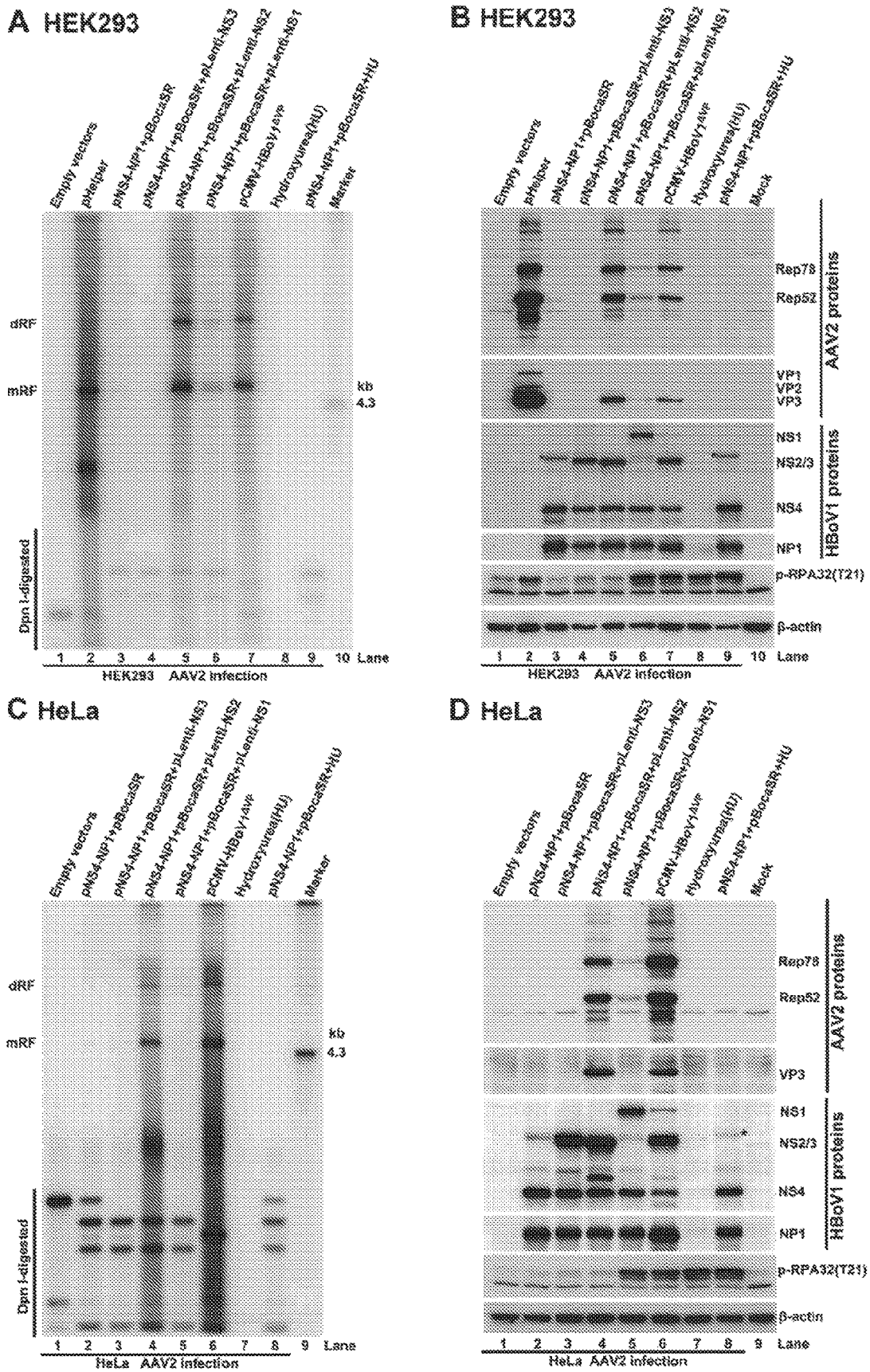

FIG. 20. Comparison of AAV2 duplex genome replications between supported by Ad pHelper and HBoV1 helper genes and between in HEK293 and HeLa cells. HEK293 and HeLa cells were co-transfected with SSV9 and Ad pHelper or HBoV1 helper plasmid, or were infected with Ad5. At 48 h post-transfection, the cells were collected, lysed for Hirt DNA extraction. Hirt DNA samples were subjected to Southern blotting with a $^{32}$P-labeled AAV2 probe. dRF, mRF, ssDNA, the 4.3 kb AAV2 marker, and Dpn I-digested DNA are indicated.

FIGS. 21A-D. HBoV1 NS2 gene together with HBoV1 NP1, NS4, and BocaSR genes and AAV2 infection. HEK293 cells (A&B) or HeLa cells (C&D) were pre-infected with AAV2. At 12 h post-infection, the infected cells were transfected with Ad pHelper or different combinations of HBoV1 helper genes, or were treated with hydroxyurea (at 2 mM) to rescue AAV2 DNA replication. At 72 h post-infection, 90% of the cells were used for Hirt DNA extraction, and 10% of the cells were lysed for protein analysis. (A&C) The Hirt DNA samples were subjected to Southern blotting using a $^{32}$P-labelled AAV2 probe. AAV2 replicative DNA forms dRF and mRF, Dpn I-digested DNA, and the 4.3 kb AAV2 DNA marker of the same load are indicated. (B&D) The protein samples were subjected to Western blotting. AAV2 proteins (Rep78, Rep52, VP1, VP2, and VP3) were probed with anti-Rep and anti-VP antibodies. The HBoV1 proteins (NS1, NS2, NS3, NS4, and NP1) were probed with anti-HBoV1 NS1C and anti-NP1 antibodies. Phosphorylation of RPA32 was probed with anti-PRA (pT21). β-actin was probed as a loading control. Asterisks indicate uncleaved NS4-P2A-NP1 fusion protein.

FIGS. 22A-D. NS2 substitutes the function of NS4 for AAV2 DNA replication following transfection of AAV2 duplex genome, as well as following AAV2 infection. HEK293 cells (A&B) or HeLa cells (C&D) were co-transfected with SSV9 and Ad pHelper or different combinations of HBoV1 helper genes, or were infected with AAV2 first and then were transfected with pHelper or HBoV1 helper genes. At 48 h post-transfection with SSV9 or 72 h post-infection with AAV2, 90% of the collected cells were lysed for Hirt DNA and 10% of the collected cells were lysed for protein analysis. (A&C) Hirt DNA samples were subjected to Southern blotting with a $^{32}$P-labeled AAV2 probe. dRF, mRF, Dpn I-digested DNA, and a DNA size marker are indicated. (B&D) The cell lysates for protein analysis were subjected to Western blotting. AAV2 proteins (Rep78, Rep52, VP1, VP2, and VP3) were probed with anti-Rep and anti-VP antibodies. HBoV1 proteins were probed with anti-NS1C, and anti-NP1 antibodies. β-actin was probed as a loading control.

Figure 23:
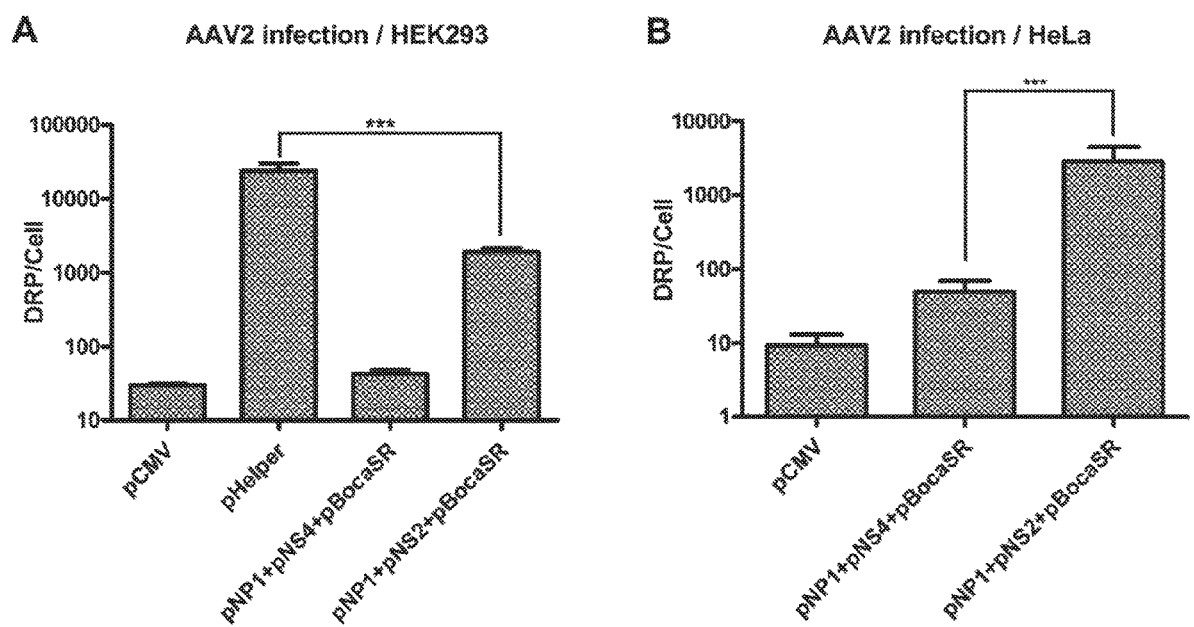

FIGS. 23A-B. AAV2 infection is productive in HEK293 and HeLa cells transfected with HBoV1 helper genes. HEK293 (A) or HeLa cells (B) were infected with AAV2 (MOI=1,000 DRP/cell) followed by transfection with Ad pHelper, HBoV1 helper gene sets, or control DNA (pCMV), as indicated. At 48 h post-transfection, the cells were collected for analyzing virus production. AAV2 production in HEK293 cells (A) or HeLa cells (B) was measured by real-time PCR as DRP/cell. Error bars show standard deviations, which were obtained from three independent experiments. Statistical analysis was performed using Student "t" test. \*\*\*P<0.0001.

FIGS. 24A-C. Comparison of the helper functions from HBoV1 and adenovirus (Ad) for the production of wild type AAV virus (WT AAV2) and recombinant AAV vector (rAAV2/2) in 293 cells. (A) Helper plasmids. Ad pHelper encodes VAI, E5 and E2A gene from Ad5; pBocaHelper I, encodes human bocavirus 1 (HBoV1) long small non-coding RNA BocaSR and an expression cassette for HBoV1 NP1 and NS2 genes. (B) pBocaHelper I fully supports WT AAV production in 293 cells. Co-transfection of AAV proviral plasmid pSSV9 and pBocaHelper yielded WT AAV2 in 293 cells as 60% efficiently as the co-transfection of pSSV9 and pHelper. AAV2 Rep and Cap proteins were efficiently expressed from pSSV9 in the presence of pBocaHelper. (C) pBocaHelper supports rAAV production in 293 cells, but at an efficiency of 1-2 log lower than pHelper. rAAV vectors were produced from triple plasmids transfection using pAV2RepCap. CMVmCherry-F5tg83fLuc and pAV2RepCap were used to generate virus using pHelper or pBocaHelper I as shown the right panel. Western blot revealed that the low vector production was largely due to the insufficient expression of capsid proteins from pAV2RepCap when the pBocaHelper I was used, implying the helper functions from pBocaHelper failed to stimulate the AAV2 capsid protein expression from the P40 promoter in the context of the ITR-less AAV2 trans helper as compared to the pHelper.

FIGS. 25A-E. Increasing the expression of AAV capsid and Rep52 led to efficient rAAV production by pBocaHelper I. (A) Plasmids for rAAV production. The CMV promoter was used in pCMVAAV2Cap to expression AAV VP proteins. The AAV Rep expression was either from pAV2rep, which utilized AAV P5 and P19 promoters to express Rep78/68 and Rep52/40, or from pAV2-Rep-CMVoptRep52, in which a CMV-optRep52 cassette was included to enhance the Rep52/40 expression. (B) Western Blot analysis of the AAV2 Rep and Cap expression from the indicated rAAV production systems. (C) Production yields of rAAV by the indicated AAV trans helpers in the presence of pHelper or pBocaHelper I. Production yields with pBocaHelper I and pAV2-Rep-CMVoptRep52 are improved within 50% that of traditional vector production with pHelper (about 100× improved from FIG. 24C). (D) Negatively stained transmission electron micrographs demonstrated effective rAAV genome package from the production systems using pHelper or pBocaHelper I. (E) rAAV2/2 vector produced by pBocaHelper transduced cells as efficiently as that produced by Ad pHelper, indicating by the reporter expression of mCherry and fLuc in 293 and Hela cells.

FIGS. 26A-D. Expression of Ad E2A gene significantly increased the efficiency of the rAAV production by pBocaHelper. (A) Plasmids for rAAV production. AAV VP proteins were expressed under the strong CMV promoter by pCMVAV2cap. AAV Rep genes were expression by AAV P5 and P19 promoter from the pAAV2Rep. (B) Western blot analysis of the AAV2 Rep and Cap expression. (C) Southern Blot analysis of rAAV genome replication. (D) The addition of adenovirus E2a gene expression enhanced the rAAV production system using pBocaHelper I. The production yield of rAAV2/2 vector reached a level of two times higher than traditional methods using Ad pHelper in 293 cells. The HBoV1 helper system can be also applied for other rAAV serotype vectors, it demonstrated similar trend of efficiency to pseudopackage rAAV2 genome into AAV5 capsid for rAAV2/5.

DETAILED DESCRIPTION

HBoV1 is pathogenic to humans, causing acute respiratory tract infections in children. HBoV1 has a selective tropism for the apical surface of well-differentiated human airway epithelia (HAE). A safe and efficient viral vector for gene therapy (rAAV/HBoV) has been constructed by pseudopackaging a recombinant adeno-associated virus 2 (rAAV) genome into HBoV1 capsid. This disclosure involves a newly discovered HBoV1 small non-coding RNA (BocaSR) and its applications. BocaSR is encoded at the 3' non-coding region of the HBoV genome and transcribed from an intragenic RNA polymerase III (Pol III) promoter. BocaSR is the first long non-coding RNA found in the parvovirus family, it plays an essential role in HBoV1 replication and coordinates the expression of viral proteins. This disclosure also reveals that HBoV1 can serve as a helper virus for AAV productive infection (i.e., replication of the WT virus and packaging of rAAV), and BocaSR is a key functional component in this process. In the absence of helper function from adenovirus, the HBoV1 gene products (minimal requirement: BosaSR, NS4 and NP1) fully support AAV viral DNA replication, and also vector production of rAAV and rAAV/HBoV when the AAV Rep and AAV or HBoV Cap genes are also provided in trans. The applications of BocaSR include: target for anti-viral therapies; production for a safer recombinant HBoV1 (rHBoV1) vector, eliminating the replication competent virus (RCV) contamination; directed evolution of AAV and/or HBoV1 capsids, using HBoV1 as a helper virus to select and rescue rAAV and/or rHBoV1 genomes from the library-infected cells/tissues of animals; and adenovirus helper independent vector production system for rAAV and rAAV2/HBoV vectors.

The bocavirus-transcribed noncoding small RNA (BocaSR) is 140 nts. BocaSR diverges from both associated (VA) RNAs and Epstein-Barr virus-encoded small RNAs (EBERs) in RNA sequence, representing a third species of this kind of Pol III-transcribed viral noncoding RNA. Unlike the VA RNAs, BocaSR localizes to the viral DNA-replication centers of the nucleus and is essential for expression of viral nonstructural proteins independent of RNA-activated protein kinase R and for replication of HBoV1 genomes. The identification of BocaSR and its role in virus DNA replication reveals potential avenues for developing anti-viral therapies.

Definitions

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, viral vectors (such as adenoviruses, parvoviruses include bocavirus and adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Large varieties of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eleven serotypes of primate AAVs, AAV-1 to AAV-11. For example, serotype AAV2 is used to refer to an AAV which contains capsid proteins encoded from the cap gene of AAV 2 and a genome containing 5' and 3' ITR sequences from the same AAV2 serotype. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by one or two AAV inverted terminal repeat sequences (ITRs). The term rAAV vector encompasses both rAAV vector particles and rAAV vector plasmids.

A "helper virus" for AAV refers to a virus that allows AAV (e.g., wild-type AAV) to be replicated and packaged by a mammalian cell. A variety of such helper viruses for AAV are known in the art, including adenoviruses, herpes viruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC.

BoV is bocavirus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to a BoV, which is identified by and distinguished from other BoVs based on capsid protein reactivity with defined antisera, e.g., there are four known serotypes of human bocavirus (HBoV), HBoV1, HBoV2, HBoV3, and HBoV4. However, included in BoV are serotypes derived from other non-human mammals such as swine and gorilla BoV. Like for MV, different serotypes of HBoV and BoV can have different tropisms that infect different cell types and organs.

A "BoV vector" as used herein refers to a bocavirus vector which may comprise a polynucleotide sequence not of BoV origin (i.e., a polynucleotide heterologous to AAV), typically a sequence of interest for the genetic transformation of a cell. Vector constructs, the heterologous polynucleotide is flanked by LEH and 3'UTR-REH, or a minimal OriR. The term BoV vector encompasses both BoV vector particles and Boy vector plasmids.

An "origin of replication" ("ori") is a DNA sequence, e.g., in a bocavirus, that when present in a cell may be capable of maintaining linked sequences, and/or is a site at or near where DNA synthesis initiates. As described hereinbelow an ori for bocavirus includes TRS and NS1 nicking and binding sequences (NSBEs).

rAAV/BoV is a chimeric vector which is composed of a non-human BoV capsids and a rAAV genome. In such a chimeric virus there is no genetic information from BoV within the genome. The rAAV genome may be from any serotype of AAV. rAAV/HBoV is a chimeric vector which is composed of HBoV capsids and a rAAV genome. In such a chimeric virus there is no genetic information from HBoV within the genome. The rAAV genome may be from any serotype of AAV.

A "Chimeric virus" or "Chimeric viral particle" refers to a viral particle composed of at least one capsid protein and an encapsidated polynucleotide, which is from a different virus.

An "infectious" virus or viral particle is one that comprises a polynucleotide component, which it is capable of delivering into a cell for which the viral species is trophic. The term does not necessarily imply any replication capacity of the virus.

Tropism as used herein, is a term referring to the ability of a particular viral serotype to productively infect cells of differing phenotypes or organs to deliver their genomic information to the nucleus.

A "gene" refers to a polynucleotide containing at least one open reading frame that is capable of encoding a particular protein after being transcribed and translated.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene includes at least a portion of an open reading frame of a gene which is partly or entirely heterologous (i.e., foreign) to the transgenic organism, or may represent an open reading frame or a portion thereof of a gene homologous to an endogenous gene of the organism, which portion optionally encodes a polypeptide with substantially the same activity as the corresponding full length polypeptide, e.g., wild-type polypeptide, or at least one activity of the corresponding full length polypeptide.

By "transgenic cell" is meant a cell containing a transgene. For example, a stem cell transformed with a vector containing an expression cassette can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter. The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

The term "isolated" when used in relation to a nucleic acid, peptide, polypeptide or virus refers to a nucleic acid sequence, peptide, polypeptide or virus that is identified and separated from at least one contaminant nucleic acid, polypeptide or other biological component with which it is ordinarily associated in its natural source. Isolated nucleic add, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription. The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Promoters include AAV promoters, e.g., P5, P19, P40 and AAV ITR promoters, as well as heterologous promoters. By "enhancer" is meant a nucleic acid sequence that, when positioned proximate to a promoter, confers increased transcription activity relative to the transcription activity resulting from the promoter in the absence of the enhancer domain.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences," are specific sequences that tend to disrupt read-through transcription by RNA polymerase, presumably by causing the RNA polymerase molecule to stop and/or disengage from the DNA being transcribed. Typical examples of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarily between the nucleic adds. The degree of complementarity between nucleic acid strands has significant effects on the efficiency and strength of hybridization between nucleic acid strands. This is of particular importance in amplification reactions, as well as detection methods that depend upon binding between nucleic acids.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

"Packaging" as used herein refers to a series of subcellular events that results in the assembly and encapsidation of a viral vector. Thus, when a suitable vector is introduced into a packaging cell line under appropriate conditions, it can be assembled into a viral particle, Functions associated with packaging of viral vectors are described herein and in the art.

"Host cells," "cell lines," "cell cultures," "packaging cell line" and other such terms denote higher eukaryotic cells, e.g., mammalian cells, such human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into antisense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the ad or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. The genetic element may be introduced into a chromosome or mini-chromosome in the cell; but any alteration that changes the phenotype and/or genotype of the cell and its progeny is included in this term.

"Gene targeting" is a genetic technique that uses homologous recombination to change an endogenous gene, e.g., delete the gene, remove exons, add a gene or alter the splice donor and receptor sequence, add a gene, or change one or more bases in the DNA.

"Gene editing" is a type of genetic engineering in which DNA is inserted, deleted or replaced in the genome of an organism using a recombinant nuclease, e.g., a heterologous nuclease.

"Gene correction template" is the exogenous template that is used to introduce DNA into, delete DNA from or otherwise replace or alter DNA in the genome of an organism.

A cell is said to be "stably" altered, transduced or transformed with a genetic sequence if the sequence is available to perform its function during extended culture of the cell in vitro. In some examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species. For example, a preparation of virus is said to be "substantially free" of helper virus if the ratio of infectious virus particles to infectious helper virus particles is at least about $10^2$:1; e.g., at least about $10^4$:1, including at least about $10^6$:1 or at least about $10^8$:1. Preparations may also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the capsid proteins VP1, VP2 and VP3).

A preparation of AAV is said to be "substantially free" of helper virus if the ratio of infectious AAV particles to infectious helper virus particles is at least about $10^2$:1; e.g., at least about $10^4$:1, including at least about $10^6$:1 or at least about $10^8$:1. Preparations may also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; e.g., at least about 10,000 or at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

The term "prophylactically effective amount" is meant to refer to the amount necessary to, in the case of infectious agents, prevent an individual from developing an infection, and in the case of diseases, prevent an individual from developing a disease.

The term "therapeutically effective amount" is meant to refer to the amount necessary to, in the case of infectious agents, reduce the level of infection in an infected individual in order to reduce symptoms or eliminate the infection, and in the case of diseases, to reduce symptoms or cure the individual.

"Inducing an immune response against an immunogen" is meant to refer to induction of an immune response in a naïve individual and induction of an immune response in an individual previously exposed to an immunogen wherein the immune response against the immunogen is enhanced.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

rBoV Vectors

Besides prophylactic or therapeutic gene products, recombinant BoV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts). In addition selected pairs of rBoV vectors having portions of open reading frames flanked by appropriately placed splice acceptor sites and/or splice donor sites, or having transcription regulatory sequences such as a heterologous enhancer, a heterologous promoter, or a heterologous enhancer and a promoter, may be employed.

A BoV vector of the invention may comprise a polynucleotide that is heterologous to BoV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the BoV genomic coding region, but is generally flanked on either side by LEH, 3'UTR and REH.

A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rHBoV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or CP4; as well as vaccinia or poxvirus inducible promoters.

Removal of one or more BoV genes is in any case desirable, to reduce the likelihood of generating replication-competent virus ("RCV"). Accordingly, sequences encoding structural and/or non-structural, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by BoV LEH, 3'UTR and/or REH and in one embodiment do not share any substantial homology with the BoV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCV.

The BoV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the BoV vector and complementary packaging gene(s), if any, are provided in the form of bacterial plasmids, BoV particles, or any combination thereof. In other embodiments, either the BoV vector sequence, the packaging gene(s), or both, are provided in the form of genetically altered (e.g., inheritably altered) eukaryotic cells. The development of host cells inheritably altered to express the BoV vector sequence, BoV packaging genes, or both, provides an established source of the material that is expressed at a reliable level.

A variety of different genetically altered cells can thus be used in the context of this invention. By way of illustration, a mammalian host cell may be used with at least one intact copy of a stably integrated BoV vector. A BoV packaging plasmid can be used to supply replication functions. Alternatively, a stable mammalian cell line can be used to supply replication functions. The BoV VP genes, providing the encapsidation proteins, can be provided together with a BoV NS1 and/or NP1 gene or separately. Other combinations are possible and included within the scope of this invention.

rAAV Vectors

Besides prophylactic or therapeutic gene products, recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts). In addition selected pairs of rAAV vectors having portions of open reading frames flanked by appropriately placed splice acceptor sites and/or splice donor sites, or having transcription regulatory sequences such as a heterologous enhancer, a heterologous promoter, or a heterologous enhancer and a promoter, may be employed. See, e.g., U.S. Pat. No. 6,436,392, the disclosure of which is incorporated by reference herein. For example, a first AAV vector may include a first DNA segment comprising a 5'-inverted terminal repeat of AAV; a second DNA segment comprising a promoter operably linked to a DNA fragment comprising an exon of a gene and a splice donor site, wherein the second DNA segment does not encode a full-length polypeptide; and a third DNA segment comprising a 3'-inverted terminal repeat of AAV; and a second AAV vector comprising linked: a first DNA segment comprising a 5'-inverted terminal repeat of AAV; a second DNA segment comprising a splice acceptor site and a DNA fragment with at least one other exon which together with the DNA segment of the first AAV vector encodes a full-length polypeptide; and a third DNA segment comprising a 3'-inverted terminal repeat of AAV. In one example, a first AAV vector includes the following: a first nucleic acid segment comprising a 5'-inverted terminal repeat of AAV; a second nucleic acid segment comprising a portion of a gene which includes a transcriptional regulatory region; a third nucleic acid segment comprising a splice donor site; and a fourth nucleic acid segment comprising a 3'-inverted terminal repeat of AAV; and a second AAV vector comprising linked: a first nucleic acid segment comprising a 5'-inverted terminal repeat of AAV; a second nucleic acid segment comprising a splice acceptor site; a third nucleic acid segment comprising a portion of a gene which together with the nucleic acid segment of the first AAV vector comprises a gene comprising an open reading frame which encodes a functional polypeptide; and a fourth nucleic acid segment comprising a 3'-inverted terminal repeat of AAV. In a further example, a first AAV vector includes the following: a first nucleic acid segment comprising a 5'-inverted terminal repeat of AAV; a second nucleic acid segment comprising a splice acceptor site; a third nucleic acid segment comprising a portion of a gene; and a fourth nucleic acid segment comprising a 3'-inverted terminal repeat of AAV; and a second composition comprising a second AAV vector comprising: a first nucleic acid segment comprising a 5'-inverted terminal repeat of AAV; a second nucleic acid segment comprising a portion of a gene which together with the nucleic acid segment above having the portion comprises a gene comprising an open reading frame which encodes a functional polypeptide, wherein the portion of the gene includes a transcriptional regulatory region; a third nucleic acid segment comprising a splice donor site; a fourth nucleic acid segment comprising a 3'-inverted terminal repeat of AAV; which vectors in a host cell yield a RNA transcript which comprises sequences from the first AAV vector linked to sequences from the second AAV vector, which sequences are positioned so that the splice donor site is 5' to the splice acceptor site, and which transcript is spliced to a mRNA which encodes the functional protein.

Adeno-associated viruses of any serotype are suitable to prepare rAAV, since the various serotypes are functionally and structurally related, even at the genetic level. All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters. Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more AAV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., WO 95/13392); Burstein et al. (WO 98/23018); and Johnson et al. (U.S. Pat. No. 5,656, 785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

Chimeric Viruses

Human airway epithelial cells are highly resistant to infection by most viral vectors included the adeno-associated virus (rAAV), the most widely used gene therapy vector in clinical trials. Human Bocavirus 1 (HBoV1), an autonomous human parvovirus which is likely an etiological agent of acute respiratory tract infections (ARTI) associated with wheezing in infants and young children, efficiently infects HAE from the apical membrane, resulting in replication of progeny viruses and cytopathology. Impressively, HBoV1 infection of HAE at extremely low multiplicities of infection (MOI) of $10^{-3}$ DNase-resistant particles (DRP) per cell results in a productive infection. Recently, the full-length 5543-nt HBoV1 complete genome (including terminal palindromic sequences at both ends) was cloned, and cell culture systems for HBoV1 production have been established. Given the high efficiency of HBoV1 infection from the apical surface of HAE, HoBV1 was hypothesized to be suitable for engineering recombinant vectors for human airway gene therapy.

HBoV1 is a relative of AAV and other Parvoviridae family members. HBoV1 belongs to the genus Bocavirus, while AAV is in the genus *Dependovirus*. HBoV1 and AAV are both small single-stranded DNA viruses, but 90% of encapsidated HBoV1 genomes are of the minus strand, while for AAV, an equal ratio of plus and minus strands are encapsidated. These two viruses differ greatly in their lytic phase life cycle; AAV requires co-infection with a helper virus, while HBoV1 autonomously replicates progeny in permissive cells. The HBoV1 genome size is 5543 nt, 18.5% (863 nt) larger than that of AAV2 (4679-nt), and its structural features include asymmetrical hairpins with unique palindromic sequences at 5' (140 nt) and 3' (200 nt) termini, which are involved in replication and encapsidation, and a single P5 promoter that transcribes all viral structural and non-structural proteins. This is in contrast to the inverted terminal repeats and multiple internal promoters found in AAV genomes. The HBoV1 genome encodes three major open reading frames (ORF). Two of them code for nonstructural proteins, NS1/NS2 and NP1, which are essential for virus replication. The third ORF encodes two structural capsid proteins VP1 and VP2. By contrast, the AAV cap ORF encodes three capsid proteins, VP1, VP2, and VP3. HBoV1 capsid surface topology possesses common features with other parvoviruses (icosahedral capsid), and is most closely similar to human parvovirus B19. Like the cloned AAV genome, a plasmid that encodes the HBoV1 proviral genome is infectious and can be used to produce infectious particles through transfection into HEK 293 cells without the need for helper virus co-infection.

Cross-genera pseudopackaging between Parvoviridae was first established when a rAAV genome was encapsidated into a human parvovirus B19 capsid. This resultant cross-genera chimera was able to deliver the rAAV genome into human bone marrow cells that are resistant to rAAV infection. Thus, it was hypothesized that pseudotyping the rAAV genome into HBoV1 capsid might create a novel chimeric vector with unique properties for gene therapy of CF and other pulmonary diseases.

The production of rHBoV1 vectors and chimeric rAAV2/HBoV1 vectors is described herein below. The first virus was a conventional recombinant vector (a rHBoV1 vector). An open reading frame disrupted or gutted HBoV genome carrying a foreign gene is packaged inside the HBoV1 capsid. rHBoV1 vector is produced in HEK293 cells by trans-complementation from the co-transfection of rHBoV1 proviral plasmid and HBoV1 helper plasmid. The rHBoV1 proviral plasmid harbors a foreign gene (of about 5.2 kb in length or more, which can accommodate a heterologous promoter, e.g., a strong promoter, operably linked to an open reading frame for the foreign gene) and all the cis-elements for replication and package, the helper plasmid encodes only the expression cassette for HBoV viral proteins. One important feature of the HBoV1 virus is that its genome autonomously replicates in permissive cells, in contrast to rAAV, which is a dependent parvovirus and needs helper virus coinfection for replication.

With the success in trans-complementation for rHBoV1 vector production, a so-called replicative rHBoV1 vector was developed by retaining the coding sequences for HBoV1 rep genes but replacing the structural gene by a transgene. This type of vector can deliver a high level of therapeutic gene expression in the airway cells for the therapy such as CF, AAT deficiency, COPD, or lung cancers. Such a replicating HBoV1 vector could have high utility as a vaccine against WT HBoV1 infections.

Another vector developed was an AAV2-HBoV1 chimeric virus, which packages a rAAV genome into a HBoV1 capsid particle. The vector was also produced in HEK293 cells with a procedure similar for rAAV vector, but the capsid genes are substituted by HBoV1 capsids. This AAV/HBoV1 vector combines both the advantages of AAV and HBoV1 transduction biology, with less safety concerns than the rHBoV1 vector since rAAV vector genomes have been extensively studied in many pre-clinical research and clinical trials, but higher airway cell tropism than rAAV. More importantly, the large HBoV1 package capacity makes it possible to encapsidate an oversized rAAV genome up to about 5.5 kb or about 6.0 kb. The 20% greater capacity than rAAV is enough to house a strong expression cassette for effective gene expression. A rAAV genome provides advantages of persistent gene expression by the stable circular transduction intermediates and double stranded genome concatemers. Indeed, AAV/HBoV1 vectors featured more persistent transgene expression than the rHBoV1 vector. Furthermore, the rescue and replication of rAAV genomes in HEK293 cells was very efficient, so that the production yield of the AAV/HBoV1 vector was also better than an rHBoV1 vector.

Utilizing the larger packaging capacity of HBoV1, a rAAV2/HBoV1-CFTR vector was prepared that harbors a 5.5 kb oversized rAAV genome with a 5.2 kb CFTR expression cassette having a strong chimeric promoter that included the human CMV immediate gene enhancer and the chicken 3-actin promoter (CBA promoter). That vector demonstrated about 30% restoration of CFTR-mediate chloride currents in CF HAE following apical infection. Therefore, the vector can efficiently deliver normal CFTR protein expression on the surface of the airway epithelial cells and correct the defective CFTR specific chloride transport in the CF HAE. In addition, the HBoV1 genome can encapsidate the self-complementary double stranded form of a rAAV genome of about 2.7 kb to about 2.8 kb in length, which vector can bypass genome conversion and allow for enhanced or more rapid transgene expression. The AAV/HBoV chimeric vectors could also be expanded to other therapies for other lung diseases such as alpha-antitrypsin deficiency, asthma, and lung cancer, as well as vaccination against wild-type HBoV infections in infants.

The capsids and/or genomes of the viruses of the invention may be chimeric, e.g., as a result of directed evolution.

Uses of Chimeric Virus or rAAV

The chimeric virus or rAAV can be used for administration to an individual for purposes of gene therapy or vaccination. Suitable diseases for therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene. Vectors of this invention may also be used to deliver gene-editing components and a single stranded DNA template to genetically correct gene defects through homologous recombination. For example, negative single strand rAAV genomes without positive strands may facilitate homologous combination, e.g., in conjunction with a DNA endonuclease that cleaves at the target site of homology in the genome that is contained within the rAAV genome. In this case, the rAAV genome may encode, for example, CRISPR/Cas9 and a guide RNA (gRNA) and the site of genomic homology targeted for gene editing. In another example, a rAAV genome may be employed along with a guide DNA (gDNA) for use with the NgAgo-gDNA gene editing system (see, Gao et al., *Nature Biotech.*, 2016, doi:10.1038/nbt.3546, the disclosure of which is incorporated by reference herein). In this system, a region of the rAAV genome contains an expression cassette for the Argonaute (NgAgo), and the gDNA (5' phosphorylated single strand guide DNA) is introduced using different delivery methods including non-viral delivery system.

Vaccination can be conducted to protect cells from infection by infectious pathogens. As the traditional vaccine methods, vectors of this invention may be used to deliver transgenes encoding viral, bacterial, tumor or fungal antigen and their subsequent expression in host cells. The antigens, which expose to the immune system to evoke an immune response, can be in the form of virus-like particle vaccines or subunit vaccines of virus-coding proteins. Alternatively, as the method of passive immunolization, vectors of this invention might be used to deliver genes encoding neutralizing antibodies and their subsequent expression in host non-hematopoietic tissues. The vaccine-like protection against pathogen infection can be conducted through direct provision of neutralizing antibody from vector-mediated transgene expression, bypassing the reliance on the natural immune system for mounting desired humoral immune responses.

The introduction of the chimeric or rAAV vectors by the methods of the present invention may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for administration. Simply dissolving a chimeric or rAAV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the chimeric or rAAV vector as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the chimeric or rAAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation include but are not limited to vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Of interest is the correction of the genetic defect of cystic fibrosis, by supplying a properly functioning cystic fibrosis transmembrane conductance regulator (CFTR) to the airway epithelium. Thus, the use of chimeric or rHBoV vectors encoding native CFTR protein, and mutants and fragments thereof, is envisioned.

Compositions may be used in vivo as well as ex vivo. In vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, one mode of administration is by aerosol, using a composition that provides either a solid or liquid aerosol when used with an appropriate aerosolubilizer device. Another mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95%, or at least about 99% of the cells of the desired tissue type. As a guide, the number of vector particles present in a single dose given by bronchoscopy will generally be at least about $1 \times 10^{12}$, e.g., about $1 \times 10^{13}$, $1 \times 10^{14}$, $1 \times 10^{15}$ or $1 \times 10^{16}$ particles, including both DNAse-resistant and DNAse-susceptible particles. In terms of DNAse-resistant particles, the dose will generally be between $1 \times 10^{12}$ and $1 \times 10^{16}$ particles, more generally between about $1 \times 10^{12}$ and $1 \times 10^{15}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant chimeric viruses or rHBoV that are substantially free of helper virus (e.g., adenovirus) and cellular proteins. It is understood that variations may be applied to these methods by those of skill in this art without departing from the spirit of this invention.

EXEMPLARY EMBODIMENTS

The use of vectors with BocaSR may be employed as a therapeutic strategy for inhibiting wild-type HBoV infection in patients and to improve the vector production system for rAAV and rAAV/BoV vectors, e.g., for CF gene therapy. For example, since BocaSR is conserved across HBoV serotypes, this anti-viral approach can be used for HBoV's that infect different organs. The identification of BocaSR enables proviral vector and helper plasmids that eliminate the contamination of replication competent virus (RCV) that have limited the application of rHBoV vectors, yielding a safer rHBoV vector.

As disclosed herein, BocaSR is essential for productive infection of well-differentiated human airway epithelium (HAE) with wild type HBoV1. Deletion of BocaSR abolishes HBoV productive infection, while restoration of BocaSR expression in trans rescues HBoV1 productive infection; BocaSR is conserved in other serotypes of HBoV and thus also is required for replication of other HBoV serotypes and has applications across serotypes; BocaSR is indispensable for replication of the HBoV1 DNA in HEK293 cells, the expression of HBoV1 non-structural proteins is not sufficient to support HBoV1 viral DNA replication in the absence of BocaSR; and BocaSR regulates the expression of NS1, NS2, NS3, and NP1, but not NS4, and play a direct role in HBoV DNA replication.

AAV is a dependent parvovirus, its lytic life cycle needs a helper virus and similarly production of rAAV requires helper virus functions. Adenovirus or herpes virus provides necessary helper function to support AAV genome replication and productive infection. To produce rAAV or rAAV/HBoV vector, helper virus function from pAd-helper (plasmid harboring an adenovirus minigene, also referred to as pHelper and pAd 4.1) is needed in addition to trans-complementation from AAV viral genes (or/and HBoV). HBoV1 is also a helper to support AAV lytic life cycle. The expression of HBoV1 gene products from a non-replicating HBoV1 plasmid (pHBoVNSCap) fully supports the replication of AAV viral genome. Furthermore, the minimal requirement of HBoV gene expression to support AAV viral DNA replication has been identified. The expression of NS4, NP1 and BocaSR are sufficient for AAV genome replication in HEK293, HeLa and CHO cells. Thus, adenovirus helper free rAAV production system is provided, e.g., the expression of NS4, NP1 and BocaSR replaces the helper function from the pAd-helper plasmid. Thus, this allows for rAAV production in non-HEK293 cell lines independent of the HEK293 integrated adenovirus E1 genes required for packaging rAAV using adenovirus helper functions in this cell line. This discovery has major applications for gene therapy in the production of rAAV, rHBoV, and rAAV/HBoV vectors for gene therapy of any disorder or target organ.

HBoV1 is a natural helper virus for AAV infection and BocaSR is a key component in supporting wild type AAV or rAAV viral DNA replication in the absence of helper functions from adenovirus. Thus, BoV, e.g., HBoV1, can be used as a helper to rescue the viral DNA replication of wild type AAV or rAAV, e.g., in HAE-ALI. Since BocaSR is conserved between various serotypes of HBoV, such applications also apply to other HBoV serotypes. Moreover, the identification of minimal requirement of HBoV1 components to support rAAV genome replication allows for an HBoV minigene. rAAV/HBoV1 vector could be produced from a single helper plasmid harboring the expression cassettes for AAV2 Rep, NP1, VPs and BocaSR. This simplifies the current 4-plasmid co-transfection rAAV/HBoV production system in HEK293 cells and also allows for the production of rAAV/HBoV virus in other cell lines. This approach can also be applied to rAAV (lacking BoV capsid) vector production.

In one embodiment, an isolated adenovirus-free rAAV or chimeric virus comprising bocavirus capsid protein and a rAAV genome, e.g., produced using the vectors described herein, is provided. In one embodiment, the bocavirus capsid is a HBoV capsid. In one embodiment, the HBoV capsid is HBoV1, HBoV2, HBoV3 or HBoV4 capsid. In one embodiment, the genome comprises an expression cassette encoding a heterologous gene product, e.g., a therapeutic protein. In one embodiment, the rAAV genome is a rAAV-2 genome. In one embodiment, the rAAV genome is a rAAV-1, rAAV-3, rAAV-4, rAAV-5, rAAV-6, rAAV-7, rAAV-8 or rAAV-9 genome. In one embodiment, the rAAV genome is derived from a non-human species of AAV. In one embodiment, the expression cassette includes a promoter that is expressed in ciliated airway epithelial cells, e.g., a FOXJ1 promoter. In one embodiment, the genome includes a trans-splicing domain. The gene product encoded by the viral genome may be a viral, bacterial, tumor or fungal antigen. In one embodiment, the transgene encodes a neutralizing antibody or an antigen binding fragment thereof. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, RSV protein, HBoV protein, influenza virus protein, SARS protein, a cytokine, e.g., IFN-alpha, IFN-gamma, TNF, IL-1, IL-17, or IL-6. Also provided is a method to express a heterologous gene product in mammalian cells which employs the isolated chimeric virus to infect cells in an amount effective to express a heterologous gene product, e.g., a therapeutic gene product, a catalytic RNA, a prophylactic gene product, a polypeptide or peptide. In one embodiment, the virus is isolated from insect cells or mammalian cells. Further provided is a method to enhance chimeric virus transduction of a mammalian cell. The method includes contacting a mammalian cell with an isolated chimeric virus comprising human bocavirus capsid protein and a rAAV genome comprising a transgene encoding a heterologous gene product and at least one agent in an amount effective to additively or synergistically enhance rAAV transduction. In one embodiment, the mammalian cell is a mammalian lung cell. In one embodiment, the agent is a porteasome inhibitor, chemotherapeutic, a lipid lowering agent, a mucolytic agent, an antibiotic or a food additive.

The isolated adenovirus-free rAAV or rAAV/BoV chimeric virus may be employed in a method to inhibit or treat a condition associated with aberrant expression of an endogenous gene product. The method includes contacting a mammal at risk of or having the condition, with an effective amount of the isolated chimeric virus comprising human bocavirus capsid proteins and a rAAV genome, wherein the rAAV genome comprises a transgene encoding at least a portion of a functional gene product, the expression of which in the mammal inhibits or treats at least one symptom of the condition. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, RSV protein, HBoV protein, influenza virus protein, SARS protein, a cytokine, e.g., IFN-alpha, IFN-gamma, TNF, 1L-1, IL-17, or IL-6. In one embodiment, the mammal is further contacted with at least one proteasome inhibitor, a chemotherapeutic, a lipid lowering agent, an antibiotic or a food additive in an amount that enhances transduction. In one embodiment, the at least one agent is LLnL (MG101), Z-LLL (MG132), bortezomib (Velcade), epoxomicin, doxorubicin, doxil, daunorubicin, idarubicin, epirubicin, aclarubicin, simvastatin, tannic acid, camptothecin, or cisplatin. An agent may be employed in a method to enhance virus transduction of a mammalian cell. A mammalian cell is contacted with a chimeric virus comprising a human bocavirus capsid protein and a rAAV genome and an agent in an amount effective to enhance transduction of the virus relative to a mammalian cell that is not contacted with the agent. In one embodiment, the agent is a proteasome inhibitor. Further provided is a method to enhance the expression of a transgene in a mammalian cell, where a mammalian cell is contacted with an amount of an agent that is a proteasome inhibitor and a chimeric virus comprising a human bocavirus capsid protein and a rAAV genome comprising the transgene. The amount of the agent enhances transduction of the rAAV, thereby enhancing expression of the transgene, relative to a mammalian cell that is not contacted with the agent.

Also provided is a method in which a mammal subjected to viral gene therapy with an isolated chimeric virus comprising human bocavirus capsid proteins and a rAAV genome, wherein the genome comprises a transgene the expression of which in the mammal is therapeutic, is administered an agent that is a proteasome inhibitor in an amount effective to enhance expression of the transgene in the cells of the mammal relative to cells in a mammal that are not contacted with the agent. In one embodiment, the rAAV encodes a therapeutic peptide or a therapeutic polypeptide. In one embodiment, the cell or mammal is contacted with the agent before the cell or mammal is contacted with the virus. In one embodiment, the cell or mammal is contacted with the virus before the cell or mammal is contacted with the agent. In one embodiment, the cell or mammal is contacted with the virus and agent concurrently. In one embodiment, the agent and the virus are administered to the lung. In one embodiment, the virus is orally administered. In one embodiment, the virus is nasally administered. In one embodiment, the virus is administered to a blood vessel.

Further provided is a method to immunize a mammal. The method includes administering to a mammal an isolated chimeric virus comprising human bocavirus capsid proteins and a rAAV genome encoding a prophylactic gene product in an amount effective to prevent or inhibit microbial infection or replication. In one embodiment, the gene product is an antigen of a virus, bacteria, fungus or parasite. In one embodiment, the gene product is a neutralizing antibody against a virus, bacteria, fungus or parasite.

In one embodiment, a BoV vector includes minimal cis elements for terminal resolution. Because of the unique REH structure of the HBoV1 genome, the minimal requirements for terminal resolution of HBoV1 both in cis and in trans were defined using the duplex HBoV1 genome in HEK293 cells. A 46-nt minimal replication origin at the REH of HBoV1 (OriR) was identified, which contains a TRS and an unconventional NSBE. In addition, properties of nonstructural proteins NS1 and NP1 during viral DNA terminal resolution at the OriR were identified. In particular, by using the duplex replicative form of the HBoV1 genome in human embryonic kidney (HEK) 293 cells, the HBoV1 minimal replication origin (OriR) was identified at the right-end hairpin. Mutagenesis analyses confirmed the putative NS1 binding and nicking sites within the OriR. Of note, unlike the large non-structural protein (Rep78/68 or NS1) of other parvoviruses, HBoV1 NS1 did not specifically bind OriR in vitro, indicating that other viral components or cellular proteins are required for the NS1 binding to the OriR. in vivo studies demonstrated that residues responsible for NS1 binding and nicking are within the origin-binding domain. Further analysis identified that the small non-structural protein NP1 is required for terminal resolution of HBoV1 DNA at OriR. The NP1 and other viral non-structural proteins (NS1-4) colocalized within the viral DNA replication centers in both OriR-transfected cells and virus-infected cells, highlighting a direct involvement of the NP1 in the terminal resolution of viral DNA. Overall, the present study revealed characteristics of HBoV1 terminal resolution at OriR.

The disclosure provides, in one embodiment, a vector having a recombinant BoV genome useful to provide a helper-virus free ("helper-free") preparation which genome comprises a LEH, a 3' UTR (e.g., encompassing SEQ ID NO:1 or a sequence having at least 85% nucleotide sequence identity thereto, e.g., nucleotides 5199 to 5339 of a wild-type BoV genome), and a REH, wherein the REH includes a 46 nucleotide sequence comprising an OriR, e.g., an OriR having a TRS and NS1 nicking and binding site, and wherein the genome includes a mutation in NS1, and optionally NS2, NS3, VP1, VP2 or VP3, and or any combination thereof, so that NS1 protein, and optionally NS2, NS3, VP1 protein, VP2 protein and/or VP3 protein, or any combination thereof, is/are not expressed from the vector. A mutation includes a deletion of one or more nucleotides, an insertion of one or more nucleotides, or a substitution of one or more nucleotides, e.g., a substitution that creates a stop codon, or creates or eliminates a splice site, or any combination thereof. In one embodiment, the genome comprises an expression cassette encoding a heterologous gene product. In one embodiment, the gene product encodes a therapeutic protein. In one embodiment, the gene product is a viral, bacterial, tumor, parasite, or fungal antigen. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, DNA endonuclease for gene editing, e.g., CRISPR associated protein 9 (Cas9), zinc finger nuclease, Transcription activator-like effector nucleases (TALEN), Argonaute, or a cytokine, e.g., IFN-alpha, IFN-gamma, TNF, IL-1, IL-17, or IL-6. In one embodiment, the BoV genome comprises a human genomic DNA segment as template for gene correction through homologous recombination between the viral genome and genomic DNA. For example, the insert includes homology arms, e.g., >100 bp, >500 bp or >1 kb, on each side of the target alterations, e.g., an insert in rBoV of about 5.8 kb of genome homology (about 2.6 kb on either site of the targeted base pairs), where the arms individually have at least 95%, 96%, 97%, 98%, 99%, or 100% sequence identity to the genome target sequences. In one embodiment, 1 to 3 bp alterations may be targeted (e.g., in a gene like CFTR). Targets in CFTR include but are not limited to the deltaF508 CFTR mutation (a deletion of 3 bp) and the G551 D CFTR mutation (a 1 bp mutation). In one embodiment, an insertion (or a sequence that includes a deletion) may be 2 kb leaving 1.6 kb homology arms. Vectors for gene correction do not necessarily include a heterologous promoter or poly A. In one embodiment, the human genomic DNA segment is the exons/intron sequence at the 189 kb cystic fibrosis transmembrane conductance regulator locus. In one embodiment, OriR includes nucleotides 5357 to 5402 or 5430 of SEQ ID NO:25. In one embodiment, the OriR includes $(TGT)_a$-$(TGT)_b$-$(TGT)_c$-$(TGT)_d$, where at least two of a, b, c or d is present. In one embodiment, the nicking site includes CTATATCT.

A recombinant BoV e.g., rHBoV1, helper free preparation, e.g., vector generation in the absence of wild-type (WT) virus contamination, is also provided. The identification of minimal OriR allows for replication of BoV, e.g., rHBoV1, genomes without generating WT virus. Moreover, having a predominantly negative strand genome may allow for higher level of specificity as certain viral proteins could be included without viral replication to boost the immune response, e.g., the helper free virus is an attenuated BoV. In addition, having a predominantly negative strand genome may allow for higher efficiency for gene editing and/or gene correction in rBoV, as the accumulation of single strand genomes could elicit DNA damage signaling and recruit cellular DNA repair and homologous recombination factors, which facilitate the gene targeting correction. Further, the mutant genomes may enhance titers of recombinant virus and functionality of the recombinant genomes, and have applications in gene editing (homologous recombination of viral genomes with the genomic DNA) since the virus only packages one strand of the genome. By removing BoV coding regions, but not at the expense of sequences for replication and/or packaging, thereby providing a mutant BoV genome, the mutant BoV genome may be modified by adding open reading frames for certain HBoV1 proteins or other microbial proteins to enhance immune response against microbial infection. Moreover, the mutant genomes may be useful in packaging systems for chimeric AAV/HBoV1 vector. Further, a mutated REH (such as inactivated the nick site) may be incorporated into a BoV helper vector, for instance, a HBoV1 helper vector. The helper might generate replicative duplex HBoV1 genomes in transfected cells, but they are defective and would not be nicked for ss genome to produce HBoV1 replication competent virus (RCV) contamination, and such replicative forms of an HBoV1 helper might be more efficient in HBoV1 VP gene expression.

A method is provided to express a heterologous gene product in mammalian cells which employs a helper-free virus preparation having a rAAV genome; and infecting the cells with the virus in an amount effective to express the heterologous gene product. In one embodiment, the gene product is a therapeutic gene product, a catalytic RNA, a microRNA, RNA pre-transplicing molecule (PTM-RNA), a neutralizing antibody or an antigen binding fragment thereof, a prophylactic gene product, a polypeptide or a peptide. In one embodiment, the mammalian cell is a mammalian nasal epithelial cell, tracheobronchial cell or a lung cell. In one embodiment, the REH corresponds to nucleotides 5357 to 5430, e.g., 5357 to 5402, of SEQ ID NO:25. In one embodiment, the 3'UTR corresponds to nucleotides 5221 to 5302, e.g., 5221 to 5291, of SEQ ID NO:25.

In one embodiment, a method is provided to inhibit or treat a condition associated with aberrant expression of an endogenous gene product is provided. The method contacting a mammal at risk of or having the condition, with an effective amount of a helper-free virus composition having a rAAV genome, wherein the genome comprises a transgene encoding at least a portion of a functional gene product, the expression of which in the mammal inhibits or treats at least one symptom of the condition. In one embodiment, the transgene encodes cystic fibrosis transmembrane conductance regulator, β-globin, γ-globin, alpha-antitrypsin, tyrosine hydroxylase, glucocerebrosidase, aryl sulfatase A, factor VIII, dystrophin or erythropoietin. In one embodiment, an agent, e.g., a proteasome inhibitor, a chemotherapeutic, a lipid lowering agent, a mucolytic agent, an antibiotic or a food additive, is further administered. In one embodiment, the agent and the virus are administered to the lung, nasal epithelium, gastrointestinal tract, or blood. In one embodiment, the virus is orally or parenterally administered.

In one embodiment, what is provided are one or more vectors that express bocavirus VP1, VP2, VP3, NP1 and NS3/4, or any combination thereof, and a nucleotide sequence having at least 85%, 86%, 87%, 88%, 89%, 90%, 92%, 94%, 95%, 96%, 97%, 98%, 99% or more nucleotide sequence identity to SEQ ID NO:1, or a portion thereof that is capable of regulating bocaparvovirus replication, but do not express bocavirus NS1 and optionally include a BoV LEH and a REH, wherein the REH includes a 46 nucleotide sequence comprising OriR having a TRS and NS1 nicking or binding sites.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant chimeric viruses or rHBoV that are substantially free of helper virus (e.g., adenovirus) and cellular proteins. It is understood that variations may be applied to these methods by those of skill in this art without departing from the spirit of this invention.

The invention will be described by the following non-limiting examples.

Example I

HBoV1 is pathogenic to humans, causing acute respiratory tract infections in children. As described below, a bocavirus-transcribed noncoding small RNA (BocaSR) of 140 nts was identified that is transcribed from a RNA polymerase III (Pol III) promoter. BocaSR diverges from both associated (VA) RNAs and Epstein-Barr virus-encoded small RNAs (EBERs) in RNA sequence, representing a third species of this kind of Poi III-transcribed viral noncoding RNA. Unlike the VA RNAs, BocaSR localizes to the viral DNA-replication centers of the nucleus and is essential for expression of viral nonstructural proteins independent of RNA-activated protein kinase R and for replication of HBoV1 genomes. The identification of BocaSR and its role in virus DNA replication reveals potential avenues for developing anti-viral therapies.

Materials and Methods

Cell Culture

HEK293 cells (CRL-1573, ATCC, Manassas, Va.) were cultured in Dulbecco's Modified Eagle Medium (DMEM, HyClone 5H30022.01; GE Healthcare BioSciences, Pittsburgh, Pa.) with 10% fetal calf serum (#F0926, Sigma, St, Louis, Mo.) at 37° C. under 5% $CO_2$ atmosphere.

Primary human airway epithelia were generated and cultured at an air-liquid interface (HAE-ALI) in Costar Transwell inserts (#3470, Corning, Corning, N.Y.), as described in Deng et al. (2016). HAE-ALI cultures with a transepithelial electrical resistance (TEER) of >1000 $\Omega \cdot cm^2$ were selected for use in this study.

Virus Infection

HAE-ALI cultures were infected with HBoV1 at a multiplicity of infection (MOI) of 10 DNase I-resistant particles (DRP) of apical released progeny virion per cell, following a previously published method (Huang et al., 2012; Deng et al., 2016), unless otherwise indicated in the figure.

Plasmid DNA Transfection

HEK293 cells were seeded in 60-mm plates on the day before transfection unless otherwise described in the figure legend. The cells were transfected with 4 µg of plasmid DNA at a confluence of about 80%, using the LipoD293 reagent (SignaGen, Gaithersburg, Md.) and following the manufacturers' instructions. For complementation of expression of RNA or protein, 2 µg of each plasmid were co-transfected.

Extraction of Lower-Molecular Weight (Hirt) DNA and Southern Blotting

At 48 hours post-transfection, Hirt DNA was extracted from transfected cells, the DNA was digested with Dpn I, and the samples were subjected to Southern blotting as described in Guan et al. (2009).

Western Blot Analysis

Transfected HEK293 cells were harvested at 48 hours post-transfection. Infected HAE cells were harvested on the days indicated in each figure. The cells were lysed and Western blotting was performed to analyze the lysates as described in Chen et al. (2010), using the specific antibodies that are indicated in each figure.

RNA Isolation Northern Blot Analysis and RNase Protection Assay

RNA isolation: RNA samples were prepared using TRIzol Reagent (Invitrogen, Carlsbad, Calif.), according to the manufacturer's instructions.

Northern blotting on agarose gels: Five µg of total RNA was separated in a 1.4% denaturating agarose gel and visualized by staining with ethidium bromine (EB). Northern blot analysis was performed essentially as described in Sun et al. (2009), using $^{32}$P-labeled DNA probes as diagrammed in FIG. 1A. The Millenium and Century™ Markers (Invitrogen, Carlsbad, Calif.) were used as size markers.

Northern blotting on polyacrylamide gel: 5 µg of total RNA samples denatured in formamide were electrophoresed in a urea (8%) polyacrylamide gel in 1×TBE buffer (Rio, 2014). The gel was transferred to a nitrocellulose membrane and the immobilized RNA was subjected to hybridization with a $^{32}$P-radiolabeled DNA probe (nt 5129-5360 of HBoV1) and detected by phosphor imaging.

RNase protection assay: RNase protection assay was carried out as described in Sun et al. (2009) and Chen et al. (2010).

Phosphor Imaging and Quantification

After hybridization, the Southern and Northern blots were exposed to a phosphor screen, which was then scanned on a phosphor imager (Typhoon FLA 9000, GE Healthcare Life Sciences). Densitometry was performed using ImageQuant TL8.1 software (GE Healthcare Life Sciences).

Construction of Plasmids (i) pGEM-3Z-based plasmids: The HBoV1 3'UTR clones p3Z-(nt5129-5360), p3Z-(nt5165-5345), p3Z-(nt5199-5345), p3Z-(nt5201-5345), and p3Z-(nt5249-5360) were constructed by cloning the HBoV1 sequences indicated in parentheses into the pGEM-3Z vector (Promega, Madison, Wis.) using the EcoR I and Hind III sites, respectively. p3Z-(nt5129-5360) was renamed p3Z-BocaSR.

A mutant form of BocaSR in which the A- and B-boxes are disrupted (BocaSR$^{mAB}$) was synthesized at Integrated DNA Technologies (IDT, Coralville, Iowa). The following seven mutations were introduced: G17A, G25A, G50A, C53T, G60A, C63T and C115T. The BocaSR$^{mAB}$-encoding DNA was cloned it into the pGEM-3Z vector using the EcoR I and Hind III sites, and the resultant clone was designated as p3Z-BocaSR$^{mAB}$. Additional BocaSR mutants were constructed by mutating one or two nucleotides in the parental plasmid, p3Z-BocaSR. These were: p3Z-SR$^{28AG/TC29}$, p3Z-SR$^{32AA/TT33}$, p3Z-SR$^{56AT/TA57}$, p3Z-SR$^{85TG/AC86}$, p3Z-SR$^{G86C}$, p3Z-SR$^{87GT/TCA88}$, p3Z-SR$^{93CC/AA94}$, p3Z-SR$^{C103A}$, p3Z-SR$^{112CA/TG113}$, and p3Z-SR$^{119TGT/GAC121}$. In all cases the transcription start site of BocaSR was designated as nt 1.

p3Z-U6-BocaSR$^{mAB}$ were constructed by inserting U6-BocaSR$^{mAB}$ sequence into pGEM-3Z using the BamH I and Hind III sites. The U6-BocaSR$^{mAB}$ sequence was PCR amplified from pLKO-BocaSR$^{mAB}$, which was constructed by cloning the BocaSR$^{mAB}$ sequence into a U6 promoter-containing pLKO.1 vector (#10878, Addgene, Cambridge, Mass.).

p3Z-BocaSR3 and p3Z-VAI RNA were constructed as follows. The HBoV3 sequence encompassing nt 5000-5205 (GenBank accession no.: EU918736) was cloned into pGEM-3Z using the EcoR I and Hind III sites. The VAI gene (nt 10607-10769) of adenovirus type 2 (Ad2; GenBank accession no.: J01917.1) was cloned into pGEM-3Z using the Sac I and Hind III sites.

(ii) pHBoV1 NSCap-based plasmids: pHBoV1 NSCap2 is a non-replicating but NS- and VP-expressing plasmid, and was constructed by deleting HBoV1 nt 97-140 and nt 5344-5395 from pHBoV1 NSCap (Chen et al., 2010); this sequence contains the Ori (Shen et al., 2016). pHBoV1 NSCap2$^{SR(mAB)}$ was constructed by substituting BocaSR$^{mAB}$ for BocaSR in pHBoV1 NSCap2. pHBoV1 NSCap2$^{SR(85TG/AC86)}$ was constructed by substituting the BocaSR$^{85TG/AC86}$ for BocaSR in pHBoV1 NSCap2.

(iii) pIHBoV1-based plasmids: pIHBoV1, an infectious clone of HBoV1, was reported in Huang et al. (2012). pIHBoV1$^{\Delta SR}$ was constructed by deleting nt 5200-5291 of the HBoV1 sequence from pIHBoV1. pIHBoV1$^{SR(85TG/AC86)}$ was constructed by mutating dinucleotide TG at nt 5283/4 of the HBoV1 sequence to AC in pIHBoV1.

(iv) rAAV2 plasmids: pAVF5tg83luc-CMVmChery(5.4 kb) was constructed by cloning the mCherry expression cassette CMV-mCherry ORF-bGHpA into pAVF5tg83luc (5.4) (Yan et al., 2013). HBoV1 DNA fragment of nt 5041-5360 that contains the BocaSR coding sequence and the corresponding fragment of the BocaSR$^{85TG/AC86}$ mutant were inserted into pAVF5tg83luc-CMVmChery using the Sfi I and Nsi I sites, to generate pAVF5tg83luc-CMVmCherry(BocaSR) and the mutant form pAVF5tg83luc-CMVmCherry(BocaSR$^{85TG/AC86}$), respectively.

(v) pLKO.1-based constructs. The shRNA-expressing constructs were generated as described in Deng et al. (2016). The following shRNA sequences were chosen for targeting of the PKR gene: shPKR, 5'-CCG GGC TGA ACT TCT TCA TGT ATG TCT CGA GAC ATA CAT GAA GAA GTT CAG CTT TTT G-3' (SEQ ID NO:2); and a scrambled shRNA control (shScram): 5'-CCG GCC TAA GGT TAA GTC GCC CTC GCT CGA GCG AGG GCG ACT TAA CCT TAG GTT TTT G-3' (SEQ ID NO:3).

(vi) pUC19-based construct: pUC19-T7 HBoV1(nt 5200-5338) was constructed by inserting the HBoV1 DNA nt 5200-5338 and a T7 promoter sequence (5'-TAA TAC GAC TCA CTA TAG GG-3'; SEQ ID NO:4) adjacent to the 5' terminus of the HBoV1 DNA into the pUC19 vector using the EcoR I and Hind III sites. This vector was used to synthesize BocaSR RNA in vitro.

All the nucleotide numbers of HBoV1 in this study refer GenBank accession number JQ923422 unless otherwise specified.

In Vitro Synthesis of the BocaSR RNA

The BocaSR RNA was in vitro transcribed using the RiboMAX™ Large Scale RNA Production Kit (Promega) according to the manufacturer's instructions. Briefly, pUC19-T7 HBoV1 (nt 5200-5338) was linearized by digestion with Hind III, and 3 μg of the linearized DNA was used for in vitro transcription in a reaction of 50 μL. The final product was digested with DNase I and purified using the RNeasy Mini Kit (Qiagen, Valencia, Calif.).

BrdU Incorporation and RNA Fluorescence In Situ Hybridization-Immunofluorescence (FISH-IF) Assays HEK293 cells were transfected with the indicated plasmids. At 48 hours post-transfection, the cells were then incubated with BrdU-containing medium for 30 minutes as described in Luo et al. (2013). Virus-infected HAE-ALI cultures were treated with 5 mM EDTA for 5 minutes and then trypsinized (about 1×10$^5$ cells). The cells were resuspended in 1 mL of ALI medium containing 30 μM BrdU (Sigma) for 30 minutes, as described in Dent et al. (2010). The cells were then cytospun onto coverslips for FISH-IF analysis.

The Stellaris® RNA FISH kit (Biosearch Technologies, Inc., Novato, Calif.) was used to perform FISH and IF analysis, according to the manufacturers protocol for simultaneous FISH and IF, with minor modifications. Briefly, cells on coverslips were fixed with 3.7% paraformaldehyde, followed by permeabilization with 70% ethanol for at least 1 hour. Cells were washed once with Wash Buffer A and incubated with a set of four biotin-labeled anti-sense oligo probes, in Hybridization Buffer at 37° C. overnight. The four probes were: 5'-/5BiosG/TAC AGT CAC CCT TCA CTT T-3' (SEQ ID NO:5); 5'-/5BiosG/TAA CAC CAC TAC CAT CGG G-3' (SEQ ID NO:6); 5'-/5BiosG/TGT CGG CTA GGT TCG AGA C-3' (SEQ ID NO:7); and 5'-/5BiosG/TCC CCC CAC AAT GTA CAA G-3' (SEQ ID NO:8). They were synthesized at IDT and were used at a final concentration of 125 nM of each. After hybridization, the cells on the slides were blocked with 3% BSA in 4×SSC, 0.2% Tween-20 buffer for 1 hour, were co-stained with mouse anti-BrdU (#200-301-H50, Rockland, Limerick, Pa.) and rabbit anti-biotin (#A150-109A, Bethyl, Montgomey, Tex.) antibodies, then stained with secondary antibodies (Jackson ImmunoResearch Inc., West Grove, Pa.) for IF analysis. The slides were sequentially washed with Wash Buffers A and B, followed by staining with DAPI (4',6-diamidino-2-phenylindole) to detect the nuclei. Confocal images were taken using an Eclipse C1-Plus confocal microscope (Nikon) controlled by EZ-C1 software.

Rapid Amplification of cDNA Ends (RACE)

5' RACE: TRIzol-isolated total RNA from HBoV1-infected HAE cells was reversed transcribed using the SP1 RV primer (5'-CAA GGG CTG TCG GCT AGG TTC GAG A-3' (SEQ ID NO:9), nt 5318-5294) and the M-MLV reverse transcriptase (Invitrogen). The cDNA was purified and incubated with dATP and terminal transferase (TdT, NEB, Ipswich, Mass.) to add multiple adenosines to its the 3' end. The 3' end of the cDNA was then amplified using an anchored Oligo (dT) forward primer (5'-GGC CAC GCG TOG ACT AGT ACT TTT TTT TTT TTT TTT TV-3'; SEQ ID NO:10) and a reverse primer SP2RV (5'-CGA GAC GGT AAC ACC ACT ACC ATC G-3' (SEQ ID NO:11), nt 5298-5274). The final PCR product was amplified using forward adaptor primer (5'-GGC CAC GCG TCG ACT AGT AC-3'; SEQ ID NO:12) and SP3RV (5'-CAT CGG CCT GTG GTC TTG AAC CCA T-3' (SEQ ID NO:13), nt 5278-5254).

3' RACE: A 5' adenylated and 3' blocked oligodeoxyribonucleotide miRNA cloning adaptor (5' rApp CTG TAG GCA CCA TCA AT-NH2 3' (SEQ ID NO:14), #S1315, NEB) was ligated to the 3' OH of the noncoding RNA using T4 RNA ligase 2 (#M0351, NEB), following the manufacturer's instructions. The cDNA was synthesized using a reverse primer (5'-ATT GAT GGT GCC TAC AG-3'; SEQ ID NO:15) complementary to the adaptor sequence and the M-MLV reverse transcriptase (Invitrogen). Then, the 5' cDNA end was PCR-amplified using forward primer SP4FW (5'-GTG AAG GGT GAC TGT AGT OCT GAG C-3' (SEQ ID NO:16), nt 5227-5251) and the reverse primer.

PCR fragments were electrophoresed on a 1.5% agarose gel. Bands of the expected sizes were excised from the gel, and purified for Sanger sequencing at MCLAB, South San Francisco, Calif. All primers were synthesized at IDT.

Production and Transduction of Lentivirus, and Establishment of Stable Cell Lines Lentiviruses were produced and the transduction unit determined in HEK293 cells as described in Chen et al. (2010). HEK293 cells were transduced at a MOI of about 5 units per cell. At 48 hours post-transduction, the cells were cultured in the presence of puromycin at 3 µg/mL for consecutive three passages before puromycin was removed.

HBoV1 and rAAV/HBoV Vector Production

Virus production: Virus was produced using a method described in Huang et al. (2012). Briefly, HEK293 cells were cultured on 145-mm plates, and were transfected with pIHBoV1 or its mutant using polyethylenimine (PEI, Polysciences, Warrington, Pa.) at a DNA: PEI ratio of 1:3. At 48 hours post-transfection, the cells were lysed for virus purification. Both purified virus preparations and virus in medium from the apical side of HAE-ALI cultures were assessed for the number of DRP using qPCR as described in Huang et al. (2012).

rAAV/HBoV vector production: rAAV/HBoV control vector, rAAV/HBoV-BocaSR, and rAAV/HBoV-BocaSR$^{857G/AC86}$ were produced by co-transfecting HEK293 cells with an rAAV2 proviral vector (pAVF5tg83luc-CMVmChery, pAVF5tg83luc-CMVmChery-BocaSR, or pAVF5tg83luc-CMVmChery-BocaSR$^{857G/AC86}$) and the Ad helper plasmid pHelper (Agilent Technologies, Santa Clara, Calif.), an AAV2 Rep-expressing plasmid (pRep2) and a HBoV1 VP-expressing plasmid (pHBoV1 NSCap). Vectors were processed, purified and quantified, following methods in Yan et al. (2013).

Antibodies

Antibodies against the HBoV1 NS1C, NP1, and VP proteins were previously published (23, 32). Anti-β-actin (#A5441, Sigma), anti-PKR (#12297, Cell Signaling, Danvers, Mass.), anti-p-PKR (#ab81303, Abcam, Cambridge, Mass.), anti-elF2α (#5324, Cell Signaling), and anti-p-elF2α (#9721, Cell Signaling) were purchased.

Probes Used for RNase Protection Assay

RNase protection assay probes pBocaSR, pBocaSR3, and pVAI RNA were in vitro transcribed in the presence of $^{32}$P-UTP using the SP6 RNA polymerase and EcoRI-digested p3Z (nt 5129-5360), p3Z-BocaSR3, and p3Z-VAI RNA, respectively. Probe pBocaSR-VAI was in vitro transcribed from a synthesized DNA of SP6 promoter sequence, BocaSR (nt 5129-5360 of HBoV1 DNA) and VAI RNA (nt 10607-10769 of Ad2 DNA) in order.

The human β-actin probe (pβ-actin) was transcribed using EcoR I-linearized pTRI-Actin-human plasmid (Invitrogen).

Results

Figure 1:
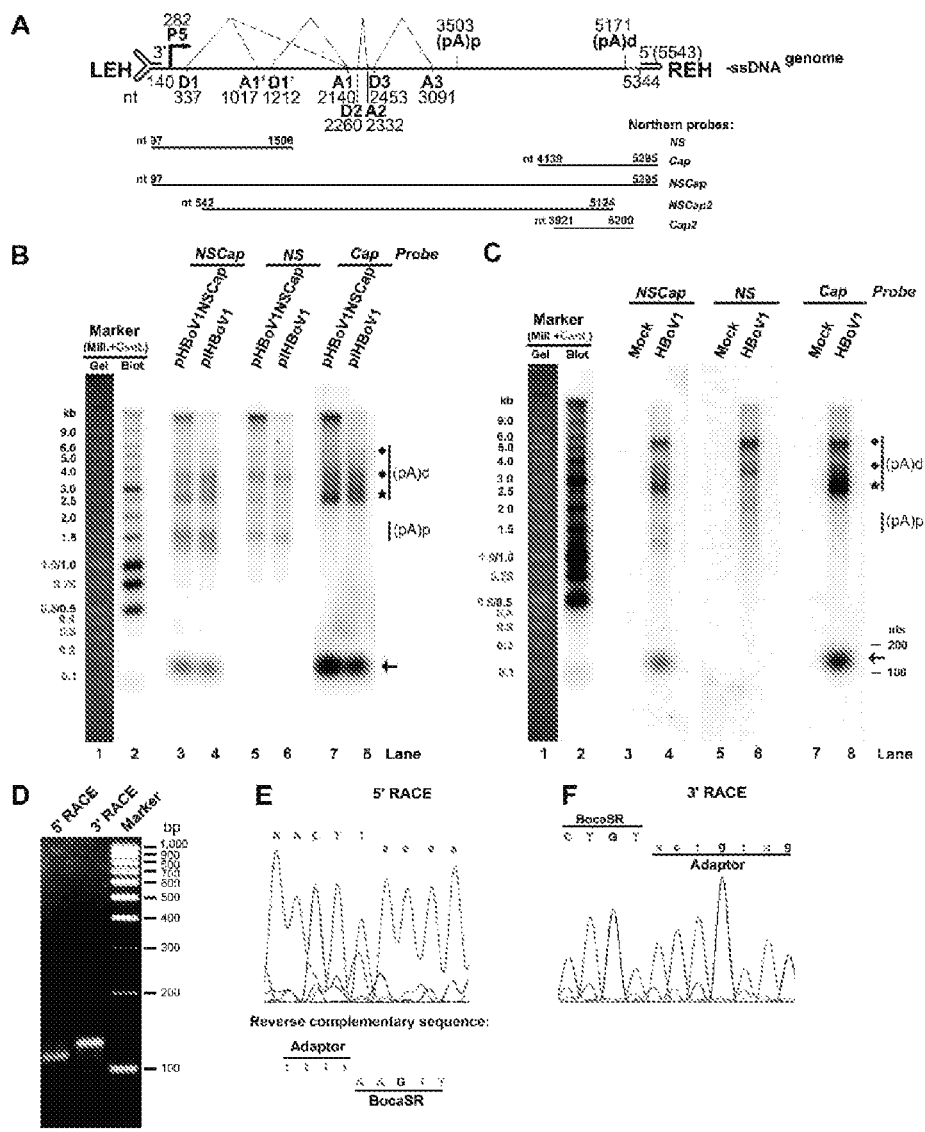
FIGS. 1A-F. HBoV1 encodes a novel non-polyadenylated small RNA. (A) Schematic diagram of the HBoV1 genome. The negative sense single-stranded (-ssDNA) genome is depicted. Indicated are the locations of the transcription units, promoter P5, splice donors (D1, D1', D2, and D3), splice acceptors (A1, A1', A2, and A3), and proximal and distal polyadenylation sites ((pA)p and (pA)d, respectively). The left- and right-end hairpin (LEH and REH) structures are also shown, as are the 3' non-coding region (NCR, red) and the probes used for Northern blot analysis (nucleotide numbers included). (B&C) Expression of viral transcripts in transfected HEK293 cells and infected HAE-ALI cultures. (B) HEK293 cells were transfected with pHBoV1 NSCap or pIHBoV1. (C) HAE-ALI cultures were infected with HBoV1 or mock-infected. At 48 hours post-transfection, or at 10 days post-infection, total RNA was extracted. 5 µg of each RNA were analyzed by Northern blotting with probes as indicated. (pA)p and (pA)d indicate HBoV1 mRNAs polyadenylated at (pA)p and (pA)d sites, respectively. (pA)d mRNAs indicated by diamond and asterisk encode NS and VP, respectively. Arrows indicates BocaSR band. The Millenium and Century™ Markers were loaded together in one lane for electrophoresis and were visualized with ethidium bromide. An additional lane was loaded with the Millenium markers and blotted with a probe that hybridizes to them, to distinguish them from the Century Markers (sizes indicated to left of blots). (D-F) Identification of BocaSR ends by RACE. (D) 5' and 3' RACE-amplified DNA fragments were electrophoresed in a 1.5% agarose gel with DNA markers (sizes indicated at right). (E&F) Sequences of the junction regions between adaptor and HBoV1, for the DNA fragments identified by (E) 5' RACE and (F) 3' RACE.

HBoV1 Expresses a Non-Polyadenylated Small RNA in the Contexts of Both DNA Transfection and Viral Infection The expression profiles of HBoV1 genes were analyzed by Northern blot analysis of mRNA isolated from HEK293 cells transfected with a plasmid that contains the non-replicating HBoV1 NS and Cap genes (pHBoV1 NSCap), using NS, Cap, and NSCap probes (Chen et al., 2010) as shown in FIG. 1A. VP-encoding mRNA transcripts in total RNA isolated from pCMVNS*Cap-transfected HEK293 cells were also analyzed, using a Cap2 probe spanning nt 3921-5200 and an NSCap2 probe spanning nt 542-5124 (Zou et al., 2016). These analyses revealed that transfection with the HBoV1 duplex genome produces NS-, NP1-, and VP-encoding mRNAs (Zou et al., 2016; Chen et al., 2010) (FIG. 1B).

Notably, the above-described analyses of total RNA isolated from the pHBoV1 NSCap-transfected HEK293 cells detected a small transcript in the range of 100-200 nts on blots by NSCap and Cap probes (FIG. 1B, lanes 3 and 7, respectively), but not on those by NS probe (FIG. 1B, lane 5). This small RNA band was also detected in total RNA isolated from HEK293 cells transfected with pIHBoV1 using the NSCap and Cap probes (FIG. 1B, lanes 4 and 8), but not the NS probe (FIG. 1B, lane 6). Analysis of the total RNA isolated from HBoV1-infected HAE cells revealed the same result (FIG. 1C, lanes 4 and 8 vs 6), and that this small RNA is expressed at a level similar to that of the VP-coding mRNA during infection. These findings suggested that an HBoV1-specifc small RNA of approximately 150 nts is encoded at the 3' end of the duplex HBoV1 genome. This small RNA bocavirus-transcribed small RNA was named BocaSR.

Given that about 150-nt BocaSR was detected by probes spanning HBoV1 sequences that extend through nt 5395 (FIGS. 1B and C), but not with those that end at or before nt 5200 (25), and that it is present only in total RNA and not in mRNA samples (32), it was speculated that this transcript was encoded by HBoV1 sequence encompassed by the nt 5124-5395 fragment and not a spliced form of the viral polyadenylated mRNA. To identify the exact ends of the BocaSR, both 5' and 3' rapid amplification of cDNA ends (RACE) were performed (FIG. 1D). Subsequent sequencing of the 5' RACE product identified nt 5199 of the HBoV1 genome as the 5' end, with the junction sequence reading 5'-tttt/AAGTT-3' (capital letter represents viral sequence) (FIG. 1E). Sequencing of the 3' RACE product identified the junction sequence between the adaptor and HBoV1 sequence as 5'CTGT/actgtag-3', confirming the 3' end of the BoaSR to be nt 5338 (FIG. 1F). We concluded that BocaSR spans nt 5199-5338.

Collectively, these results define a novel non-polyadenylated (noncoding) small RNA of 140 nts between nt 5199 and nt 5338 of the HBoV1 genome, encoded at the 3' NCR between the VP-coding region and the right-end hairpin (REH) (FIG. 1A, HBoV1 genome in red).

BocaSR is a RNA Polymerase III-Transcribed Intragenic Viral Small RNA

Figure 2:
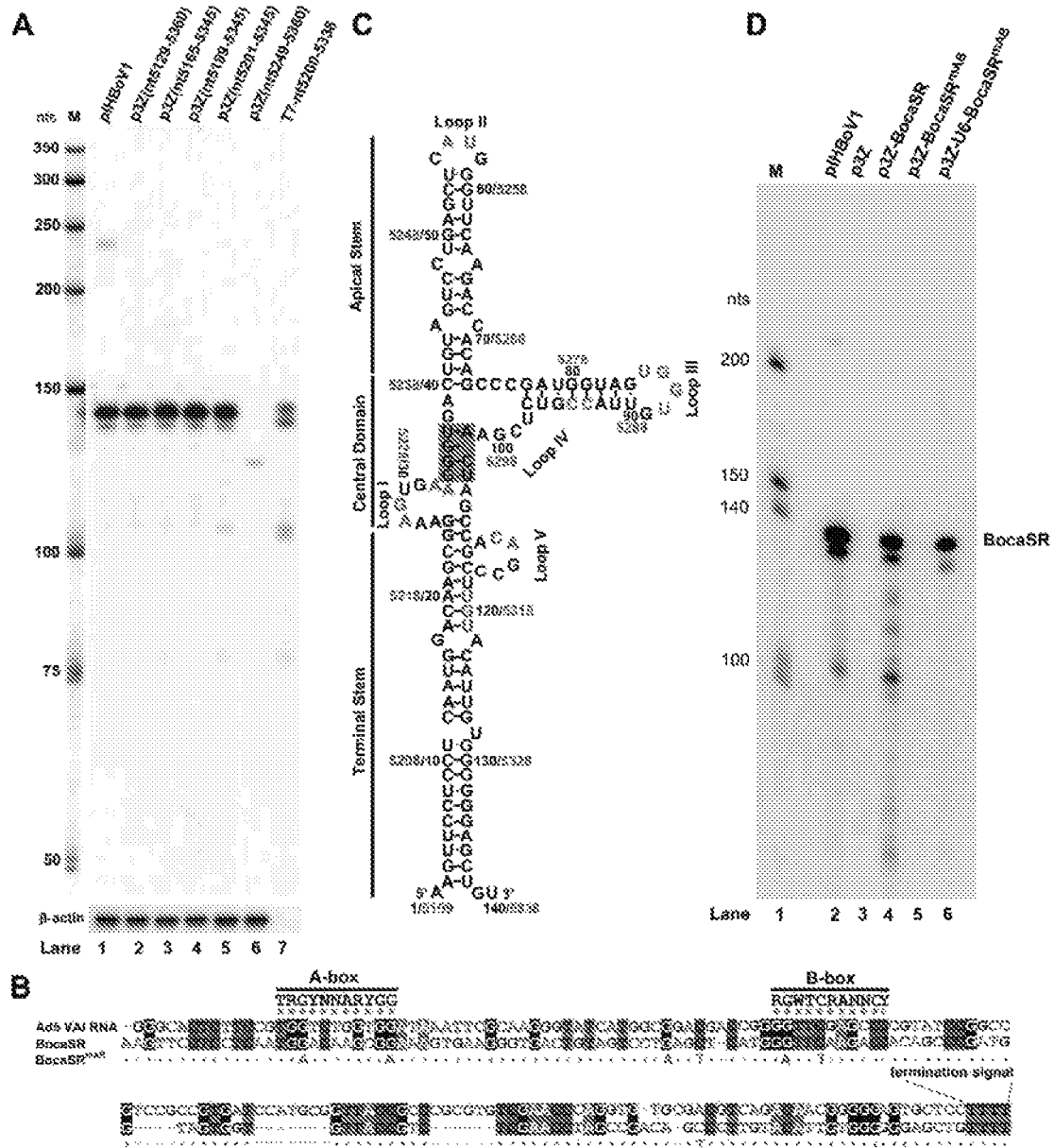
FIGS. 2A-D. HBoV1-encoded BocaSR is transcribed from an intragenic Pol III promoter. (A) Identification of the BocaSR-transcribing region by RNase protection assay. HEK293 cells were transfected with pIHBoV1 or pGEM-3Z-based plasmids carrying the indicated coding sequences. At 48 hours post-transfection, total RNA was extracted. 10 µg of total RNA and 100 ng of in vitro transcribed BocaSR (lane 7) were protected with probes pBocaSR and pβ-actin, respectively. Lane M, $^{32}$P-labeled RNA markers (Qui et al., 2002), with sizes shown to left. (B) CLUSTALW-based sequence alignment. Sequences of BocaSR (SEQ ID NO:24) and Ad5 VAI (SEQ ID NO:17) RNA aligned using the CLUSTALW algorithm. Identical nucleotides are highlighted in colors. Consensus sequences of the A- and B-boxes of Pol III are indicated. Mutations used to create the A-box and B-box mutant are shown under the BocaSR sequence. (C) Predicted secondary structure of BocaSR (SEQ ID NO:26). The BocaSR structure was predicted using the KineFold algorithm, with VAI RNA serving as reference. Nucleotides of the HBoV1 genome and the BocaSR RNA sequence are shown in blue and black, respectively. Nucleotides that were changed in BocaSR mutants are shown in red. Loop structures are indicated, and the central tetranucleotide pair is highlighted in grey. (D) Identification of the A-box and B-box of BocaSR by RNase protection assay. Total RNA was isolated from HEK293 cells transfected with plasmids as indicated, at 48 hours post-transfection. 10 µg total RNA were protected using probe pBocaSR or pBocaSR$^{mAB}$. Lane M, $^{32}$P-labeled RNA markers, with sizes indicated to left.

To identify the promoter region of BocaSR, various sequences of the HBoV1 duplex genome that span the BocaSR-transcribing region (nt 5129-5360, nt 5165-5345, nt 5199-5345, nt 5201-5345, and nt 5249-5360) were cloned into the pGEM-3Z vector and transfected each plasmid into HEK293 cells to test for their expression of BocaSR. The results of RNase protection assays (RPAs) showed that except for one fragment (nt 5249-5360), all others produced BocaSR transcripts of identical length (about 140 nts) and at the level expressed from pIHBoV1 (FIG. 2A, lanes 1 versus 2-6). This RPA result confirmed that HBoV1 nt 5199-5345, a sequence that contains the entire BocaSR-transcribing region (nt 5199-5338), is fully capable of transcribing BocaSR, strongly suggesting that BocaSR is transcribed by an intragenic type II Pol III promoter, as are the adenovirus (Ad) VA RNAs, Epstein-Barr virus-encoded small RNAs (EBERs), and cellular tRNAs (Lassar et al., 1983; Schramm et al., 2002).

It was speculated that BocaSR shares features with VA RNAs or EBERs. Alignment of BocaSR with Ad5 VAI RNA revealed that BocaSR shares 51.2% identity in nucleotide sequence (with particularly high identity in the predicted A-box and B-box), and has the same transcription termination signal (TTTT) (FIG. 2B). The secondary structure of BocaSR was predicted using the KineFold algorithm (http://kinefold.curie.fr/) with constraint parameters (Mergny et al., 2005). The results suggest that the RNA has an apical stem, a terminal stem and a complicated central domain, and that its secondary structure is highly similar to that of the VAI RNA (FIG. 2C) (Mathews, 1995; Mathews et al., 1991).

To verify the predicted A-box and B-box of BocaSR, two key nucleotides in the sequence of each (nt 5199-5338) were modified, and expressed either without or with the U6 RNA Pol III promoter (Schramm et al., 2002) (p3Z-BocaSR$^{mAB}$ and p3Z-U6-BocaSR$^{mAB}$, respectively). Three additional nucleotides, none of which is located in the predicted A-box or B-box, were mutated to retain the structure; these were selected using KineFold. Mutations in either the A-box or the B-box were sufficient to abolish the expression of BocaSR (FIG. 2D, lane 5). As expected, the U6 Pol III transcribed an A-box and B-box-mutated BocaSR of the BocaSR$^{mAB}$ mutant (FIG. 2D, lane 6).

Taken together, these results confirmed that BocaSR is transcribed from an intragenic Pol III promoter in which A-box and B-box are present downstream of the transcription start site (i.e., within the transcribed mature RNA). Based on these results, it was concluded that BocaSR is a typical type II Pol III-derived small noncoding RNA (Schramm et al., 2002).

BocaSR is Indispensable for Replication of the HBoV1 DNA

Figure 3:
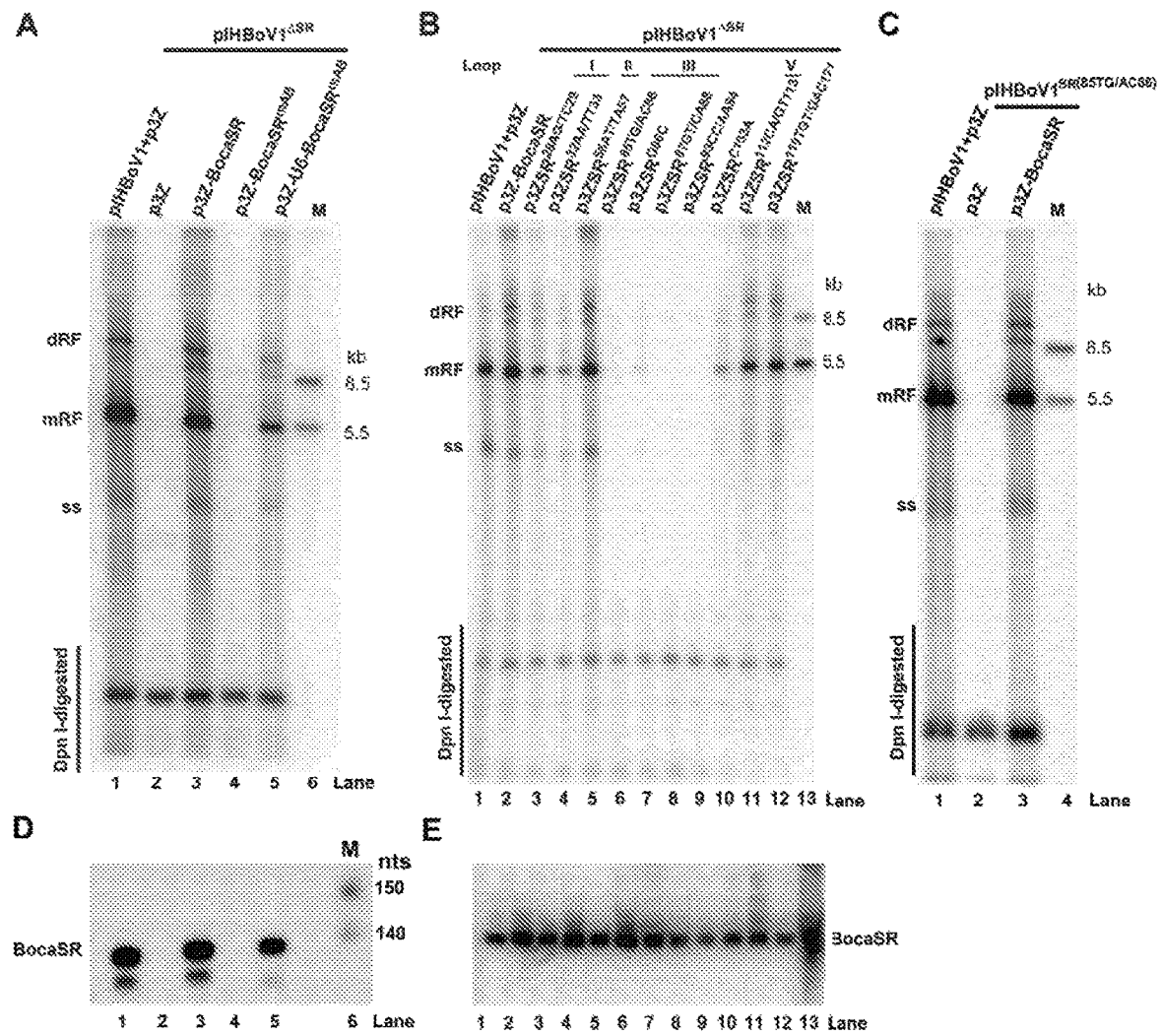
FIGS. 3A-E. Replication of the HBoV1 DNA can be restored by expressing BocaSR mutants. A-C) Southern blotting. (A&B) Viral DNA in HEK293 cells transfected with pIHBoV1 and p3Z or pIHBoV1$^{\Delta SR}$ and either (A) the indicated p3Z-BocaSR or A-box and B-box mutant (p3Z-BocaSR$^{mAB}$), or (B) the indicated BocaSR point mutant. (C) Viral DNA in HEK293 cells transfected with pIHBoV1 or co-transfected with pIHBoV1$^{SR(85TG/AC86)}$ and vector only or p3Z-BocaSR. In each panel, M indicates marker lane, with sizes shown to right and the following DNA forms indicated: monomer replicative form DNA (mRF), double replicative form DNA (dRF) and ssDNA (ss). Dpn I-digested bands are indicated. (D) RNase protection assay. Total RNA extracted from HEK293 cells transfected with plasmids as indicated in panel A was protected with probe pBocaSR or pBocaSR$^{mAB}$. (E) Northern blotting. BocaSR RNA in lanes loaded with 5 µg of total RNA extracted from transfected HEK293 cells as indicated in panel B, with pBocaSR DNA used as probe. In lane 13, 500 ng of in vitro transcribed BocaSR was used as the marker.

Previously, it was found that the presence of the HBoV1 3' NCR (nt 5221-5291) in cis is critical to viral DNA replication (Shen et al., 2016). Since the HBoV1 3' NCR is encompassed by BocaSR, we hypothesized that BocaSR is involved in replication of the HBoV1 DNA. This was addressed by analyzing the ability of BocaSR to complement replication of the replication-deficient viral DNA in HEK293 cells. It was first confirmed that deletion of BocaSR abolished replication of the HBoV1 genome. Although pIHBoV1$^{\Delta SR}$ was derived from the infectious HBoV1 duplex genome clone, the removal of BocaSR sequence abolished replication of the HBoV1 DNA in transfected HEK293 cells (FIG. 3A, lane 2). Complementation with wild-type (WT) BocaSR, but not the A-box and B-box mutated mutant (BocaSR$^{mAB}$), in trans restored replication of pIHBoV1$^{\Delta SR}$ (FIG. 3A, lanes 3 versus 4). Notably, U6 Pol III-transcribed BocaSR$^{mAB}$ also restored replication of the pIHBoV1$^{\Delta SR}$ DNA, albeit not completely (FIG. 3A, lane 5). Expression of BocaSR and BocaSR$^{mAB}$, was confirmed by RNase protection assays (FIG. 3D). The less efficiency of the U6 Pol III-driven BocaSR$^{mAB}$ in restoring pIHBoV1$^{\Delta SR}$ replication was partially due to its low level of expression. This finding suggests that the mutations in the A-box and B-box disrupted activity of the intragenic Pol III promoter without completely destroying its ability to facilitate HBoV1 DNA replication. Thus, the expression of BocaSR was confirmed to be essential to replication of the HBoV1 DNA.

To further characterize the role of BocaSR in replication of the HBoV1 DNA, point mutants less likely to affect various predicted structures within BocaSR, nor the transcription activity elements of the A- and B-box, were screened for function in HBoV1 replication. In principle, nucleotides located in the loop regions were substituted and parallel changes introduced in the complementary bases in the context of p3Z-BocaSR. Analysis using the KineFold software suggested that these loop mutants introduce no changes in structure. Three mutations located in the stem regions were also analyzed, including within tetranucleotide (GGGU/ACCU) that are similar to that of the Ad VA RNA (GGGU/ACCC) (Ma et al., 1996). All of the mutations are highlighted in red in FIG. 2C.

The efficiencies of the BocaSR mutants with respect to complementing replication of the pIHBoV1$^{\Delta SR}$ DNA were evaluated by Southern blotting. The sequence in loop III had a greater impact on replication of the viral DNA than did those in the other loops and in the stem structure. Mutations affecting loop III (85TG/AC86, G86C, and 87GT/CA88) and the loop III stem (93CC/AA94) were less effective at restoring replication of the viral DNA than those in loop I (28AG/TC29 and 32AA/TT33) and loop II (56AT/TA57) (FIG. 3B, lanes 6-9 versus 3-5). In contrast, both the mutant affecting loop V (112CA/GT113) and that affecting the terminal stem of loop V (119TGT/GAC121) retained full function, as evident from the fact that the levels of both double replicative form (dRF) and monomer replicative form (mRF) DNAs were the same on Southern blots (FIG. 3B, lanes 11 and 12 vs 2). As expected, the mutation in the tetranucleotide (C103A) restored DNA replication only partially (about 20% of levels in WT) (FIG. 3B, lane 10). Of note, the inability of those mutants to restore viral DNA replication from pIHBoV1$^{\Delta SR}$-transfected HEK293 cells was not due to loss of the expression of BocaSR, as all the tested mutants and control plasmids were capable of transcribing the 140-nt short RNA, as confirmed by Northern blotting (FIG. 3E).

The importance of a loop III mutation (85TG/AC86) was investigated. As shown in FIG. 3C, pIHBoV1$^{SR(85TG/AC86)}$ did not replicate at all in transfected HEK293 cells (FIG. 3C, lane 2). As expected, the introduction of WT BocaSR fully restored replication (FIG. 3C, lane 3), Thus, the simple 2-nt mutant affecting loop III was used for further complementation analysis in HAE-ALI cultures.

Collectively, these findings demonstrated that the expression of BocaSR is essential to replication of the HBoV1 DNA in HEK293 cells, and that loop III contains the element that is most important to its function in promoting replication of the HBoV1 DNA.

BocaSR is Essential for HBoV1 Infection of Well-Differentiated HAE Cells

Figure 4:
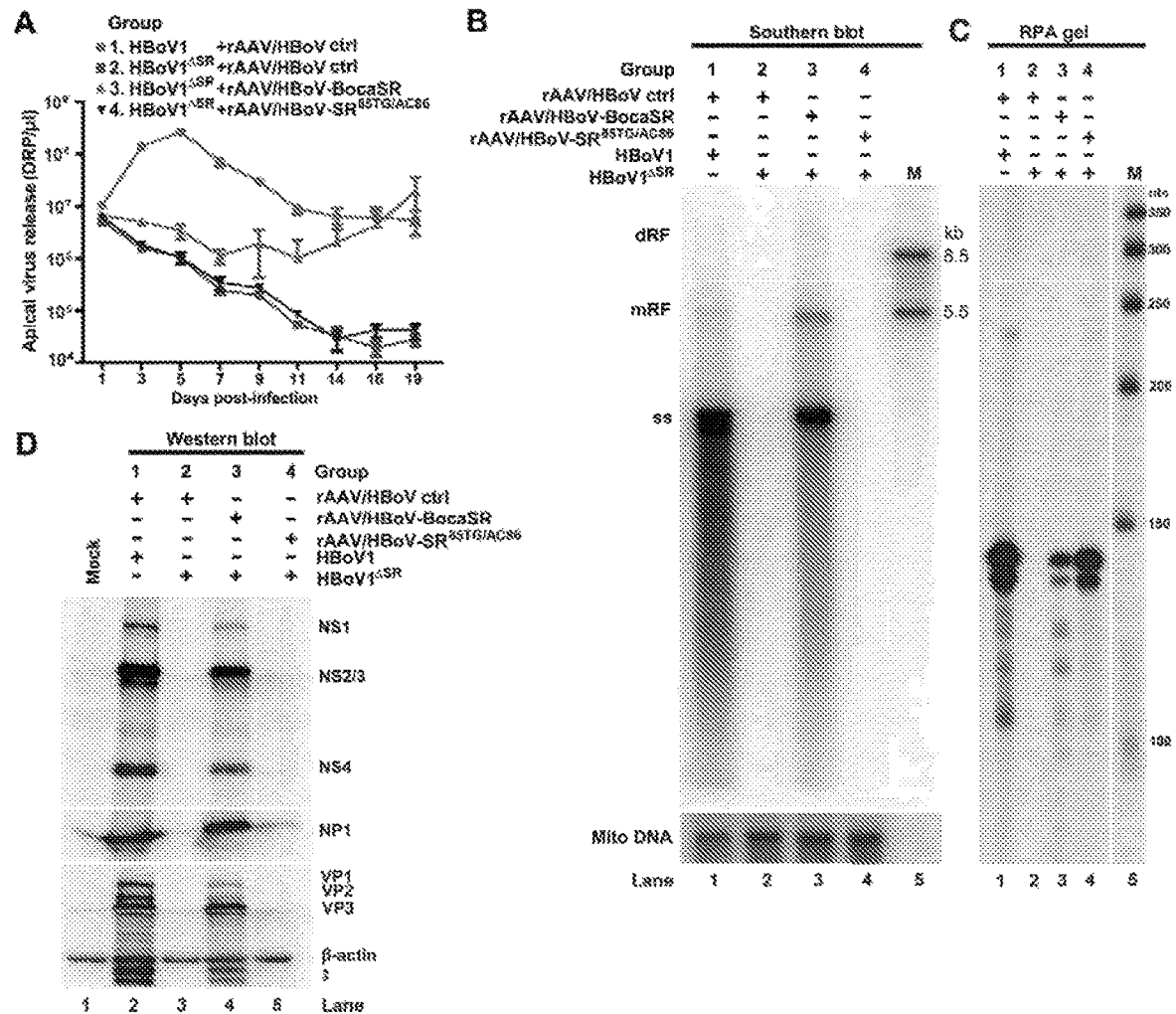
FIGS. 4A-D. Virus replication in HBoV1$^{\Delta SR}$ infected HAE-ALI cultures transduced with BocaSR-expressing rAAV2/HBoV1 vector. Polarized HAE-ALI cultures were co-infected with HBoV1 WT or HBoV1$^{\Delta SR}$ mutant purified from transfected HEK293 cells at an MOI of about 1000 DRP/cell and rAAV/HBoV vector at an MOI of about 10,000 DRP/cell (Yan et al., 2013) in groups as indicated. (A) Virus apical release kinetics. Apical washes were collected from at least three infected HAE-ALI cultures for each virus infection, and quantified for DRP by qPCR. Averages and standard deviations are shown. (B) Southern blot analysis of viral DNA. Hirt DNA was extracted from infected cells at 19 days p.i. Levels of viral DNA were assessed by Southern blotting. Mitochondrial DNA (Mito DNA; lower panel) was detected by a mitochondrial DNA probe as a control for the recovery of the Hirt DNA (Deng et al., 2016). DNA marker (M) is shown with sizes indicated to the right. (C) Analysis of BocaSR expression by RNA protection assay. Total RNA was extracted from infected cells at 19 days p.i. 10 µg of the total RNA was protected with probe pBocaSR or pBocaSR$^{85TG/AC86}$. RNA maker (M) is shown with sizes indicated to the right. (D) Western blotting detection of viral proteins in infected HAE-ALI cultures. At 19 days p.i., infected cells were lysed for Western blotting. Samples were initially blotted using anti-NS1C antibody (upper panels) and then reprobed sequentially with anti-NP1, anti-VP, and anti-β-actin (bottom panels). Bands marked with asterisk may be uncharacterized or degraded forms of VP.

To investigate the role of BocaSR in the infection of HAE cells by HBoV1, functional complementation of BocaSR in HBoV1$^{\Delta SR}$-infected HAE cells, using the rAAV/HBoV vector to deliver the WT BocaSR or BocaSR$^{85TG/AC86}$ mutant in trans, was conducted. A non-BocaSR-expressing rAAV/HBoV vector served as a negative control. Analyses of apical release of virus from the infected HAE cells revealed that infection of HBoV1$^{\Delta SR}$ was productive only in the presence of rAAV/HBoV-BocaSR. As shown in FIG. 4A, the transduction of rAAV/HBoV-BocaSR led to an increase in apical release of virus from HBoV1$^{\Delta SR}$-infected HAE cells starting on day 3. This was not the case for transduction with either the vector control or rAAV/HBoV-BocaSR$^{85TG/AC86}$, in which cases virus levels gradually decreased to background as in the case of infection with HBoV1$^{\Delta SR}$ alone (FIG. 4A). At days 16 and 19, rAAV/HBoV-BocaSR completely complemented the function to the HBoV1$^{\Delta SR}$ virus, with levels comparable to those obtained by infection with the WT virus (FIG. 4A). Replication of the viral DNA (ssDNA) on day 19 post-infection, as assessed by Southern blotting of Hirt DNA extracts from infected HAE cells, was rescued to nearly WT levels in cells co-infected with rAAV/HBoV-BocaSR but not rAAV/HBoV-BocaSR$^{85TG/AC86}$ (FIG. 4B, Southern, lanes 3 vs 4). Expression of BocaSR and the BocaSR$^{85TG/AC86}$ mutant from the respective rAAV/HBoV vectors was confirmed by RNase protection assays (FIG. 4C), although expression of BocaSR from the rAAV/HBoV-BocaSR vector was relatively poor. Expression of viral proteins (NS1-4, NP1, and VP1-3) was confirmed as well (FIG. 4D).

Taken together, these results demonstrated that BocaSR is indispensable for HBoV1 replication, and that it functions in trans to support replication of the HBoV1 DNA in well-differentiated HAE-ALI cultures.

BocaSR Regulates the Expression of NS1, NS2, NS3, and NP1, But Not NS4

Figure 5:
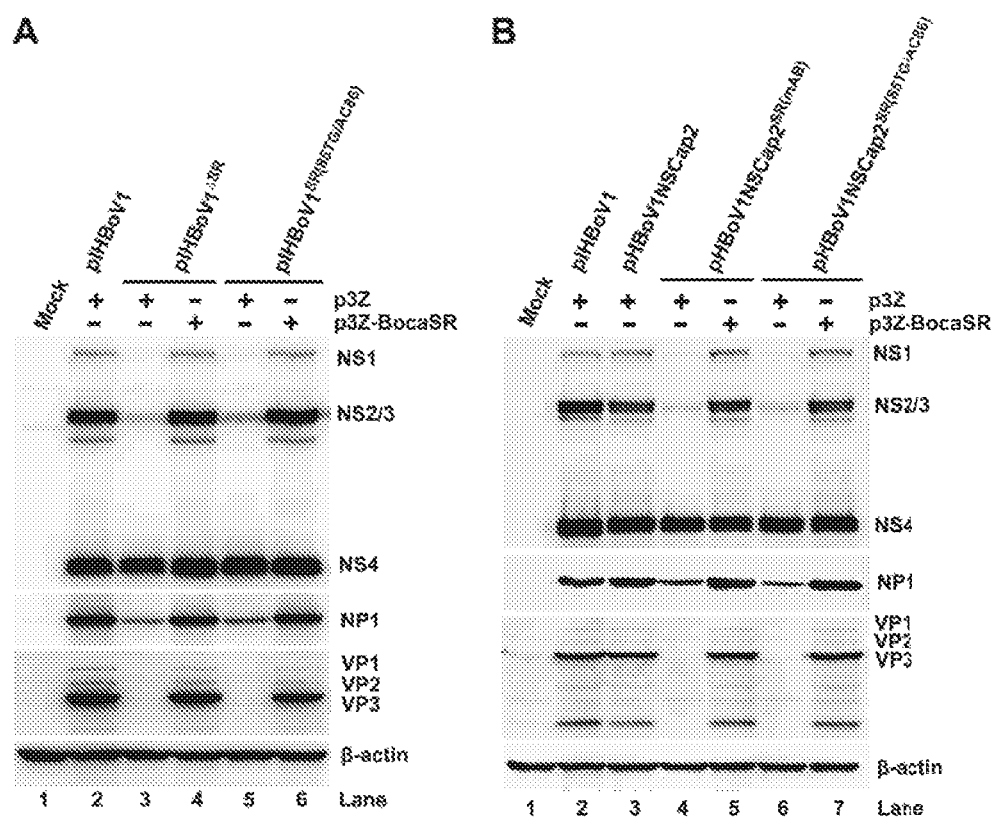
FIGS. 5A-B. HBoV1 protein expression analysis of HEK293 cells transfected with pIHBoV1-based and pHBoV1 NSCap2-based BocaSR mutants. (A) Expression from replicating pIHBoV1. HEK293 cells were transfected with pIHBoV1, pIHBoV1$^{\Delta SR}$ and pIHBoV1$^{SR(85TG/AC36)}$ with p3Z or p3Z-BocaSR co-transfection. (B) Expression from non-replicating HBoV1 plasmid. HEK293 cells were transfected with pIHBoV1, pHBoV1 NSCap2, pHBoV1 NSCap2$^{SR(mAB)}$ and pHBoV1 NSCap2$^{SR(85TG/AC86)}$, with p3Z or p3Z-BocaSR co-transfection. At 48 hours post-transfection, viral proteins were assessed by Western blotting. Blots were probed sequentially with antibodies against HBoV1 NS1C, NP1, and VP, and then against β-actin.
Figure 6:
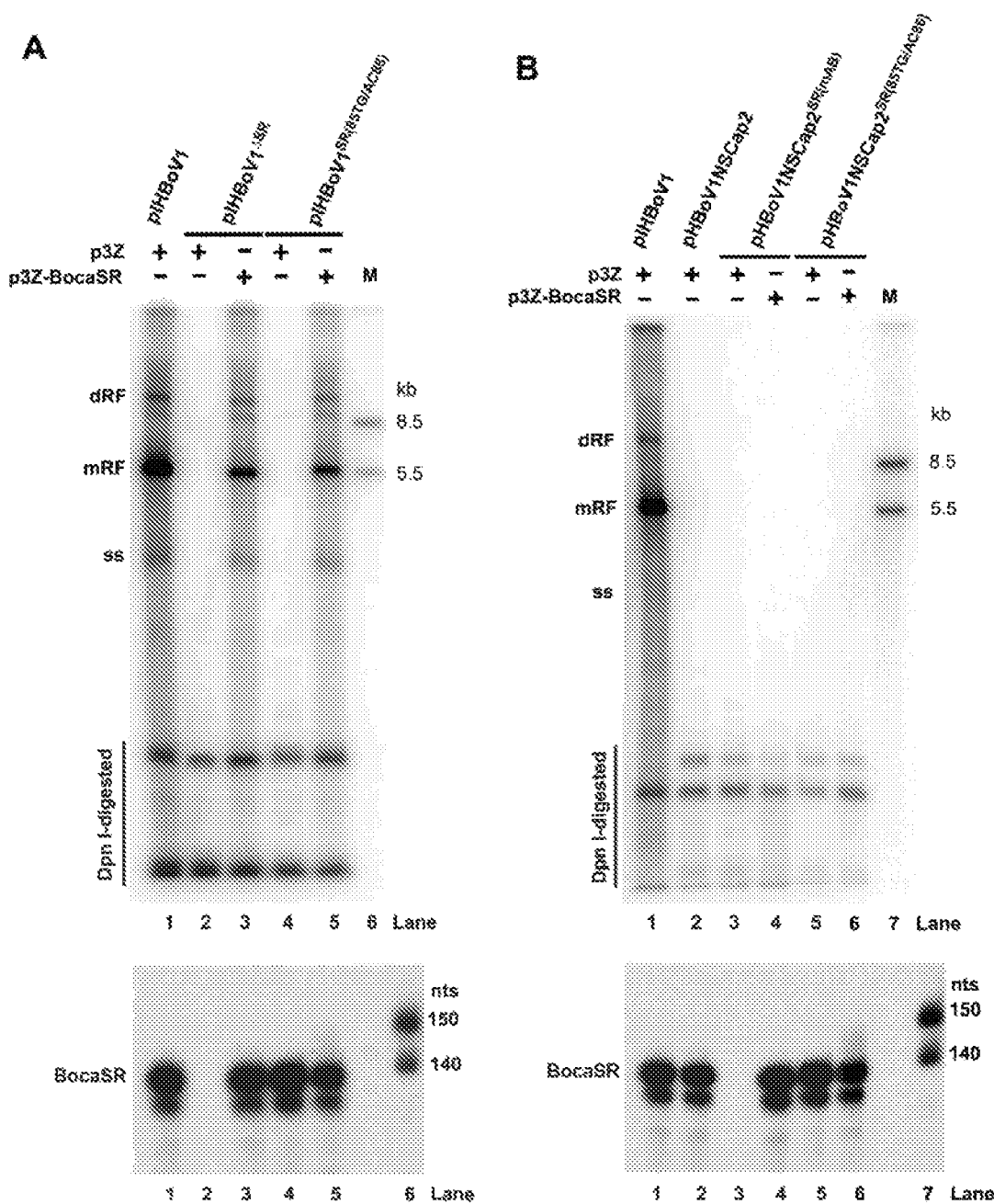
FIGS. 6A-B. DNA replication and BocaSR detection of HEK293 cells transfected with pIHBoV1-based and pHBoV1 NSCap2-based mutants. (A) Replicating pIHBoV1-based plasmids. HEK293 cells were transfected with pIHBoV1, pIHBoV1$^{\Delta SR}$ and pIHBoV1$^{SR(85TG/AC86)}$ with p3Z or p3Z-BocaSR co-transfection. (B) Non-replicating pHBoV1 NSCap2-based plasmids. HEK293 cells were transfected with pIHBoV1, pHBoV1 NSCap2, pHBoV1 NSCap2$^{SR(mAB)}$ and pHBoV1 NSCap2$^{SR(85TG/AC86)}$, with p3Z-BocaSR (+) or with p3Z (−) co-transfection. At 48 hours post-transfection, Hirt DNA samples were extracted from the transfected cells and analyzed by Southern blotting with HBoV1 NSCap probe (upper panel). At 48 hours post-transfection, total RNA samples were extracted from the transfected cells and analyzed by RNase protection assay with pBocasR, pBocasR$^{85TG/AC86}$, or pBocasR$^{mAB}$ probe (bottom panel). Both DNA and RNA markers (M) are shown to the right of the images.

To investigate the mechanism underlying BocaSR-controlled replication of HBoV1 DNA, the expression of viral proteins were assessed from BocaSR-deleted or mutated pIHBoV1 mutants. Western blotting revealed that neither pIHBoV1$^{\Delta SR}$ nor pIHBoV1$^{SR(85TG/AC86)}$ supported the expression of NS1, and that the expression of NS2/3 was reduced >10-fold, and that of NP1>3-fold (comparison to WT pIHBoV1). However, neither the deletion nor the mutation affected the expression of NS4 significantly (FIG. 5A, lanes 2 vs 3&5). When BocaSR was provided in trans by co-transfection of p3Z-BocaSR (FIG. 6A), the expression of NS1, NS2/3, and NP1 was fully restored (FIG. 5A, lanes 4&6 vs 2), To rule out the possibility that this rescue of protein expression was a consequence of replication of the viral DNA (FIG. 6A), tests were conducted in the context of non-replicating HBoV1 plasmids, pHBoV1 NSCap2$^{SR(mAB)}$ and pHBoV1 NSCap2$^{SR(85TG/AC86)}$, respectively (FIG. 6B). The expression profiles in cells transfected with pHBoV1 NSCap2$^{SR(mAB)}$ and pHBoV1 NSCap2$^{SR(85TG/AC86)}$ were similar to those in cells transfected with the pIHBoV1-based mutants (FIG. 5B, lanes 4&6 vs FIG. 5A, lanes 3&5), and expression of WT BocaSR in trans (FIG. 6B) fully restored the expression of NS1, NS2/3, and NP1 (FIG. 5B, lanes 5&7 vs 3).

These results demonstrated that BocaSR upregulates expression of the viral proteins NS1, NS2/3, and NP1, but not NS4. As NP1 is required for the expression of VP (Zou et al., 2016), BocaSR indirectly regulates VP expression as well (FIG. 5, VP). Since in HEK293 cells NS2/3 and NS4 are dispensable for replication of the HBoV1 DNA (Shen et al., 2016), these results suggest that BocaSR-upregulated expression of NS1 and NP1 is critical to viral DNA replication in HEK293 cells.

Figure 7:
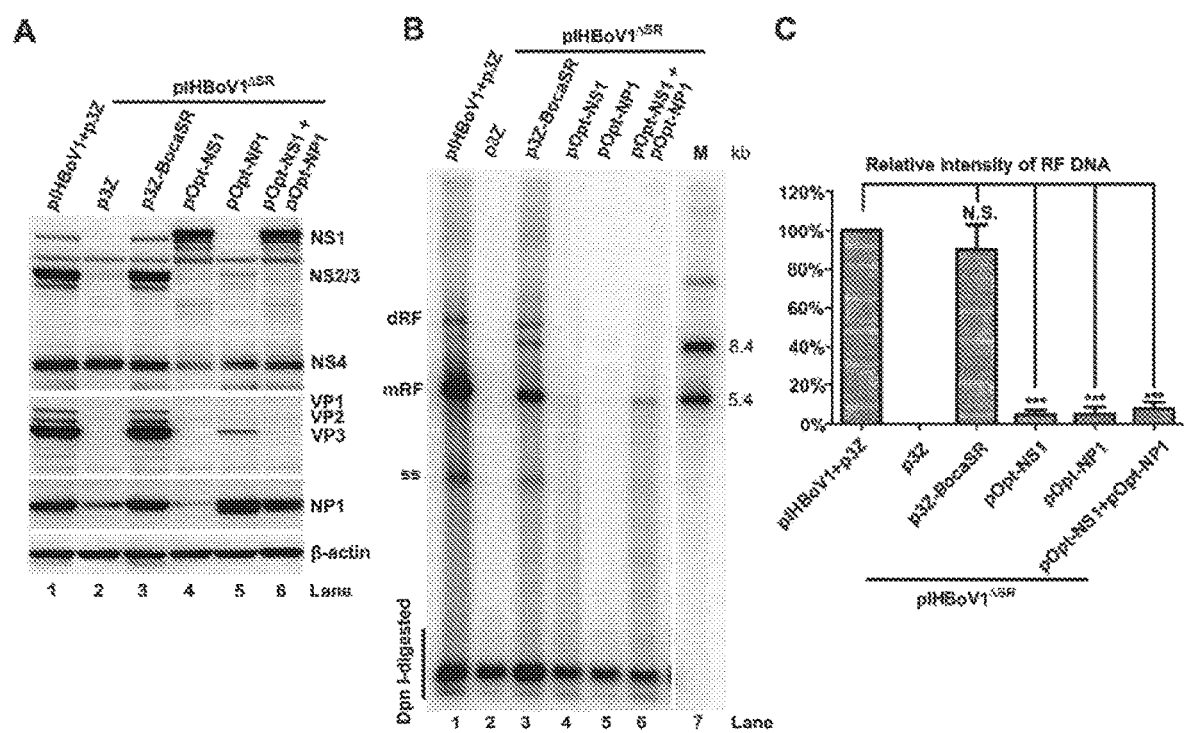
FIGS. 7A-C. Overexpressed NS1 and NP1 proteins do not rescue viral DNA replication of pIHBoV1$^{\Delta SR}$. HEK293 cells were co-transfected with pIHBoV1 and p3Z or pIHBoV1$^{\Delta SR}$ and the indicated plasmid(s). 1 µg of pOpt-NS1 (31) or pOpt-NP1 (25) (supplemented with pCI backbone vector to 2 µg), or 1 µg of each were co-transfected. (A) Expression of viral proteins in transfected cells harvested at 48 hours post-infection. Western blots were probed sequentially using antibodies against HBoV1 NS1C, NP, VP, and β-actin. (B) Levels of viral DNA in transfected cells harvested at 48 hours post-transfection. Hirt DNA sample were assessed by Southern blotting for each form of the HBoV1 DNA. (C) Quantitation of viral mRF DNA in panel B. Averages and standard deviations are shown. Statistics analysis was performed by the Student's t-test. N.S., no significance; ***P<0.01.

Expression of the Nonstructural Proteins is Not Sufficient to Fully Rescue Replication of the HBoV1 Genome in the Absence of BocaSR It was further investigated whether the reduced expression of NS1 and NP1 accounts fully for the replication deficiency of the pIHBoV1$^{\Delta SR}$ and pIHBoV1$^{SR(85TG/AC86)}$ mutants in HEK293 cells. To this end, NS1, NP1, or both were supplemented in trans and tested for complementation of the lack of BocaSR expression in HEK293 cells transfected with pIHBoV1$^{\Delta SR}$. Transfected NS1-/NP1-expressing plasmid produced NS1 and NP1 at levels similar to those in controls in HEK293 cells transfected with pIHBoV1$^{\Delta SR}$ and p3Z-BocaSR (FIG. 7A). However, this expression did not lead to a significant increase in viral DNA replication from pIHBoV1$^{\Delta SR}$ (<5% increase) relative to that produced by the expression of BocaSR in trans (FIG. 7B, lanes 3 vs 4&5). However, co-expression NS1 and NP1 had an additive effect, leading to an about 10% increase (FIG. 7B, lanes 3 vs 6, and FIG. 7C).

Figure 8:
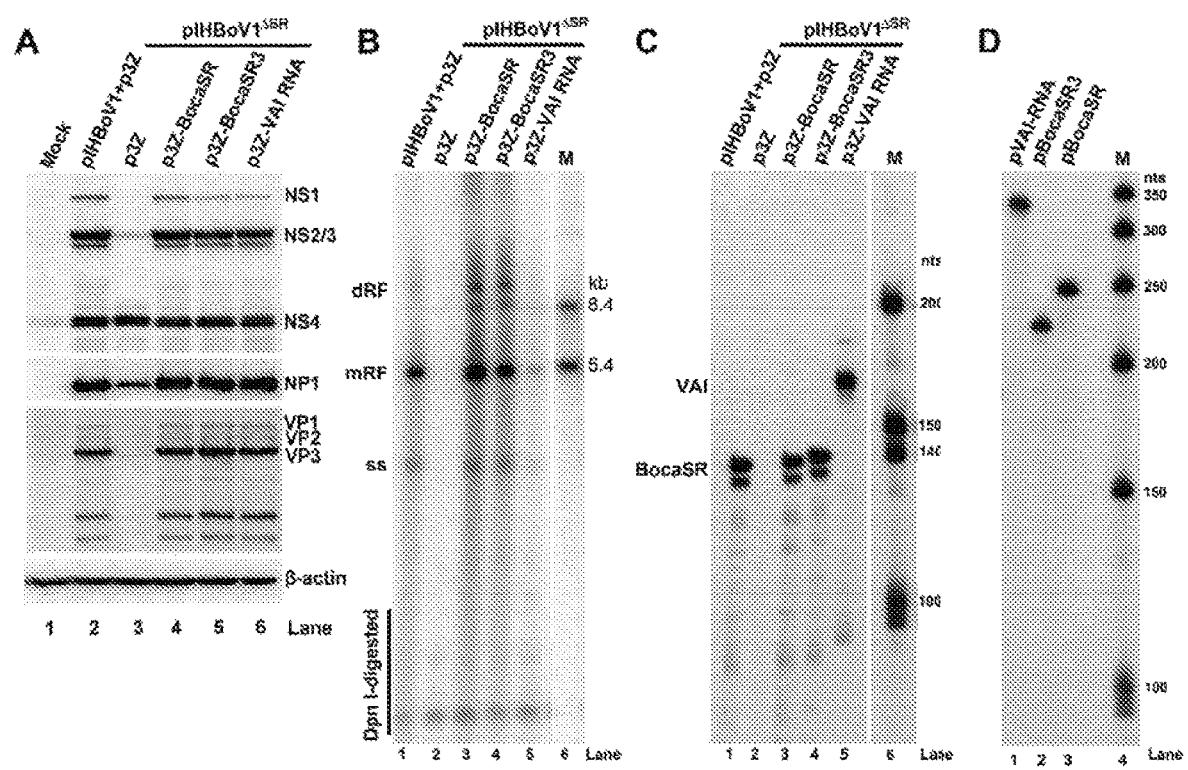
FIGS. 8A-D. Fully restored NS1 and NP1 proteins do not rescue viral DNA replication. HEK293 cells were co-transfected with pIHBoV1 and p3Z or pIHBoV1$^{\Delta SR}$ and with a complemented BocaSR or VAI RNA-expressing plasmid as indicated in each lane. (A) Western blot analysis of viral proteins. Expression of viral proteins in transfected cells harvested at 48 hours post-infection. Western blots were probed with an anti-HBoV1 NS1C antibody, and were then reprobed sequentially with anti-NP1, anti-VP, and anti-β-actin antibodies. (B) Southern blot analysis of viral DNA replication. At 48 hours post-transfection, Hirt DNA was extracted, Dpn I-digested, and assessed by Southern blotting for each form of HBoV1 DNA. (C&D) RNA protection assay of BocaSR and VAI RNA. (C) At 48 hours post-transfection, total RNA was extracted. 10 μg of the total RNA were protected by probes for BocaSR, BocaSR3, or VAI RNA. (D) Similar levels of RPA probes were used for protection in each sample.

Next, it was tested whether the supplementation of nonstructural proteins in cis could efficiently facilitate viral DNA replication. To this end, VAI RNA was expressed in trans with pIHBoV1$^{\Delta SR}$-transfected HEK293 cells in an attempt to functionally rescue expression of the nonstructural proteins, and its effects on viral DNA replication investigated. Although VAI RNA restored the expression of NS1-3 and NP1 to levels comparable to those observed when BocaSR was expressed in trans (FIG. 8A, lane 6), replication of viral DNA was only at about 10% of the levels that were observed on complementation with BocaSR (FIG. 8B, lanes 3 versus 5). Thus, in the absence of BocaSR, expression of the nonstructural protein gene is not sufficient to support effective HBoV1 DNA replication. Of note, BocaSR3 of HBoV3 fully restored not only the expression of NS1-3 and NP1 (FIG. 8A, lane 5), but also replication of the viral DNA (FIG. 8B, lane 4). The levels of expression of BocaSR, BocaSR3, and VAI RNA in above complementation experiments were confirmed to be similar by RNase protection assays (FIG. 8C), using saturated probes of equivalent activities (FIG. 8D).

Taken together, these results confirmed that BocaSR-upregulated nonstructural protein expression is necessary but not sufficient to fully support replication of the HBoV1 DNA, indicating that BocaSR plays additional roles in viral DNA replication.

BocaSR-Mediated Expression of Nonstructural Proteins is Independent of the Protein Kinase R Pathway As the VAI RNA regulates viral protein expression mainly by inhibiting the double-stranded RNA-activated protein kinase R (PKR)-eIF2α pathway (Vachon et al., 2016), BocaSR was tested for an interaction with PKR. To this end, HEK293 cells were transfected with various BocaSR-expressing plasmids and control vectors (p3Z-VAI RNA and pIHBoV1$^{\Delta SR}$, positive and negative, respectively). Then, the PKR-eIF2α pathway was activated by transfecting the cells with synthetic double-stranded RNA, polyinosinic-polycytidylic acid sodium salt (poly I:C; #P1530, Sigma) (Wang et al., 2015). The inhibition of PKR activation was assessed by Western blotting for phosphorylated PKR (p-PKR) and phosphorylated eIF2α (p-eIF2α). The expression of BocaSR following transfection with either pIHBoV1 or p3Z-BocaSR (FIG. 9A) did not result in an obvious decrease in the level of p-PKR and p-eIF2α, following its activation by poly I:C (FIG. 9B, lanes 3&6), compared with the level in the context of transfection of the p3Z-VAI RNA (FIG. 9B, lane 7). This result suggested that, in contrast to VAI RNA, BocaSR does not function as an inhibitor of PKR to reduce phosphorylation of eIF2α in upregulating the expression of nonstructural proteins.

Figure 10:
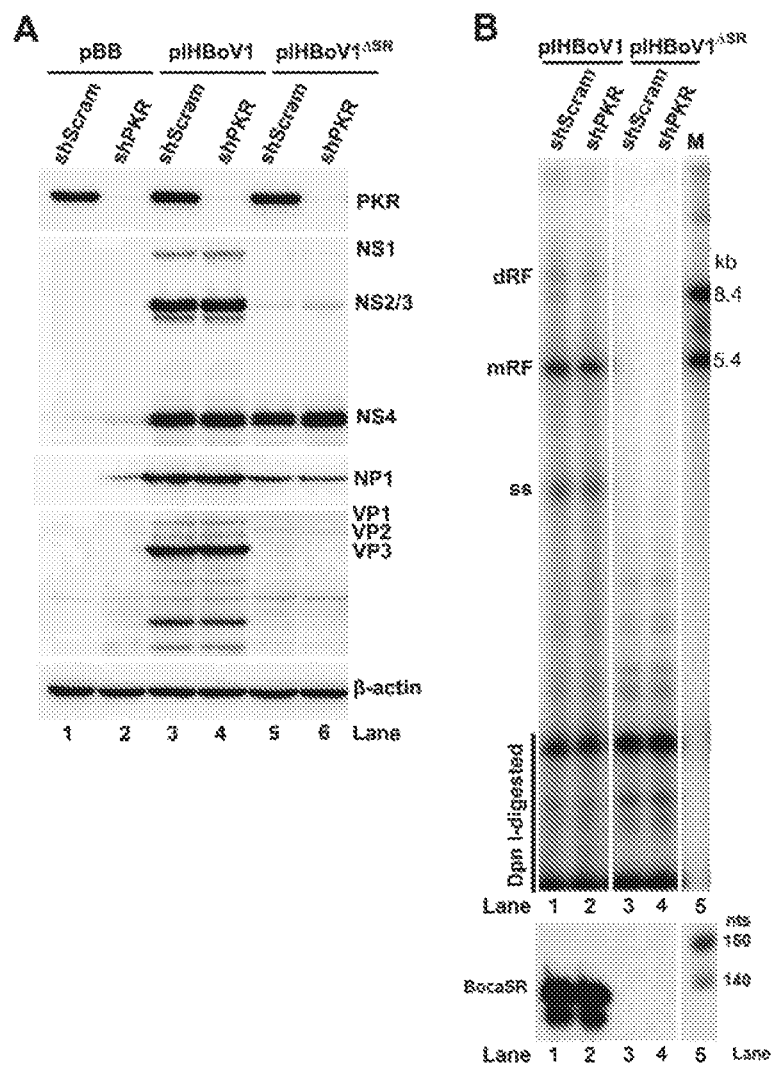
FIG. 10. Effects of PKR knockdown on expression of HBoV1 protein and replication of the HBoV1 DNA in the BocaSR-deleted pIHBoV1 mutant. HEK293 cells subjected to PKR knockdown were transfected with pBB (backbone control), pIHBoV1, or pIHBoV1$^{\Delta SR}$. (A) Levels of PKR and viral proteins in HEK293 cells at 48 hours post-transfection, as assessed by sequential Western blotting using antibodies against the NS1C, NP1, and VP proteins. (B) Levels of viral DNA in transfected HEK293 cells at 48 hours post-transfection, as assessed by Southern blotting for viral DNA. Extracted total RNA at 48 hours post-transfection was protected by the pBocaSR probe. Markers (M) of both DNA and RNA are shown to the right.
Figure 12:
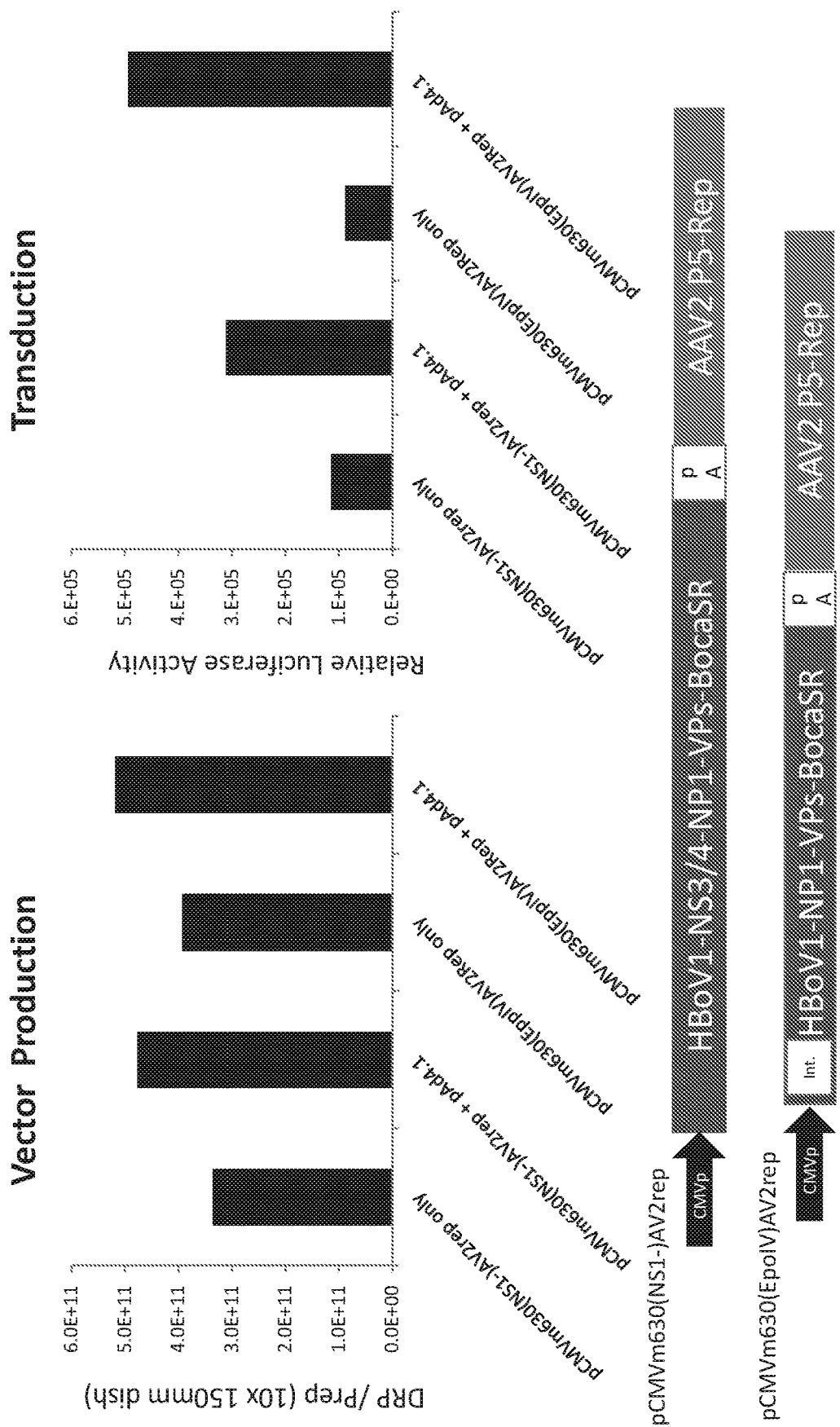
FIG. 12. Adenovirus (Adv) helper-independent system for the production of rAAV2/HBoV1. HEK 293 cells were transfected with rAAV proviral plasmid pAV2-CMVmCherry-F5tg83fLuc with the indicated helper plasmids. rAAV/HBoV1 vector can be produced in the absence of pAd4.1 (with Adv minigene, E2, E4Orf6 and VA). Production yields were from 10 plates (150 mm) transfected 293 cells, and transduction were compared by the firefly luciferase activities (3-day-post-infection) from HAE-ALI infected with equal amount each vector (MOI=10K DRP/cell).
Figure 13:
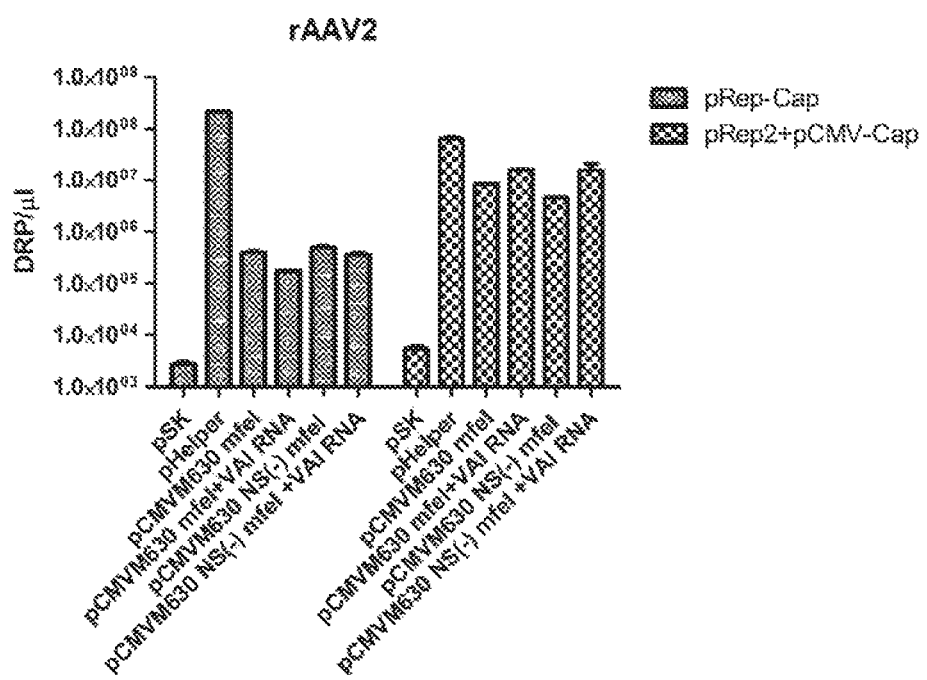
FIG. 13. BoV1 genes facilitate rAAV2 vector production without adenovirus helper genes E2, E4Orf6 and VA (pHelper) but at 10-fold lower that the vector production with pHelper in HEK293 cells. Left panel: HEK293 cells seeded in 6 well plate were co-transfected with pAAV2-CMV-mCherry-Luc (4.6 Kb), pRep2-VP, and adenovirus pHelper or indicated HBoV1 helper (pCMV-M630 MfeI or pCMV-M630(NS1-) MfeI) along with or without VA RNA using lipoD293 transfection reagent. The cells were harvested at 48 hours post-transfection by adding 600 μl/well lysis buffer (25 mM Tris-HCl pH 8.0, 150 mM NaCl, 2 mM MgCl$_2$ and 0.5% Doc) followed by adding 10 μL DNase I and incubate at 37° C. for 1 hour to digested un-packaged DNA. The cell lysates were clarified by centrifuge at 3500 g for 15 minutes. 10 μL clarified cell lysates were dilute with 200 μL PBS-MgCl$_2$ solution and treated with benzonase for two hours and DNase resistance DNA were extracted using Qiagen Blood DNA Kit. The DNA was quantified by qPCR. Right panel: The cells were transfected using the same method as described above except that the pRep2-VP plasmid was split into pRep2 and pCMV-AAV2 Cap. DNase resistance DNA was extracted and quantified using the same method as described in left panel. pCMV-M630an pCMV-M630(NS1-) are pCMVHBoV1 NSCap and pCMVHBoV1 NS(−)Cap, respectively, which were removed the Mfe I-digested fragment of 1,477 nt (to prevent HBoV1 capsid expression), resulting in pCMV-M630 MfeI or pCMV-M630 (NS1-) MfeI, respectively.

To more definitively exclude a role for PKR in BocaSR-upregulated expression of nonstructural proteins and replication of the viral DNA, a PKR-knockdown HEK293 cell line was established (FIG. 10A), PKR-null HEK293 cells were transfected with pIHBoV1 and pIHBoV1$^{\Delta SR}$, respectively. ShScram-expressing HEK293 cells were transfected in parallel as a control. Although pIHBoV1 expressed all the viral nonstructural proteins (FIG. 10A, lanes 3&4) and replicated in both PKR-null and shScram-expressing cells (FIG. 10B, lanes 1 and 2), pIHBoV1$^{\Delta SR}$ did not (FIG. 10A, lanes 5 and 6 and FIG. 10B, lanes 3 and 4). Expression of BocaSR in transfected cells was confirmed by RNase protection assays (FIG. 10B). Thus, PKR does not appear to play a role in BocaSR-facilitated replication of the HBoV1 DNA.

As VAI RNA is exclusively expressed in the cytoplasm (Mathews et al., 1991), where it interacts with PKR (Mellits et al., 1990; Garcia et al., 2006), the localization of BocaSR was investigated. Indeed, BocaSR is expressed in the nucleus in HEK293 cells transfected with p3Z-BocaSR, as demonstrated by the RNA fluorescence in situ hybridization-immunofluorescence (FISH-IF) assay (FIG. 9C, RNase A(-)/p3Z-BocaSR). The specificity of detection of BocaSR in this experiment was confirmed by RNase A-treatment of the transfected cells (FIG. 9C, RNase A+/p3Z-BocaSR). More importantly, in both pIHBoV1-transfected HEK293 cells and HBoV1-infected HAE cells, BocaSR was located exclusively in the nucleus and within the centers of viral DNA replication (the autonomous parvovirus-associated replication (APAR) bodies), which were pulse-labeled with BrdU (FIG. 9C, pIHBoV1 and HBoV1, respectively).

Considering that restoring the expression of viral nonstructural proteins rescues only a fraction (about 10%) of HBoV1 DNA replication from pIHBoV1$^{\Delta SR}$ (FIG. 8), these results suggest that BocaSR plays a direct role in replication of the viral DNA.

Discussion

In this report, a Pol III-transcribed viral noncoding RNA, BocaSR, is described. It is the first of Pol III-transcribed small RNA to be identified in parvoviruses, and shares a high level of similarity with respect to sequence and secondary structure with Ad VAI RNA, but functions differently during virus infection. BocaSR is indispensable to the replication of viral DNA; in its absence the virus is not capable of upregulating the expression of NS1-3 as well as that of NP1, yet this is not sufficient to support efficient viral DNA replication. Thus, BocaSR represents a unique viral Pol III-driven noncoding RNA that plays a direct role in viral DNA replication.

Sequence and structure of BocaSR. Previous studies revealed a remarkable feature of the 3' NCR of primate bocaparvoviruses: those of HBoV1, HBoV2 and HBoV3 fold into almost identical secondary structures (Kapoor et al., 2011; Babkin et al., 2015). This feature appears to be unique; it is not shared by the carnivore bocapaivovirus 1 MVC (minute virus of canines) (Sun et al., 2009), bocaparvoviruses from other non-primate species, or other parvoviruses. The BocaSR of HBoV1 is the most divergent among these noncoding RNAs; whereas the BocaSR sequences of HBoV2-4 and gloria bocavirus (GBoV1) share 97.8% identity in the coding region that has been sequenced, that of HBoV1 shares only 86%, while with HBoV2-4 and GBoV1 (FIG. 11). Importantly, the HBoV1 BocaSR shares sequence identity ranging from 46.1%-51.2% with the other four Pol III-driven viral small RNAs: VAI, VAII, EBER1, and EBER2. The VAI and VAII RNAs share about 60% identity, EBER1 and EBER2 share about 57% identity, and EBERs and VAs share 37-50% identity. Therefore, these Pol III-driven viral small RNAs are diverse in their transcribing sequence. These findings suggest that BocaSR represents an unknown species of Pol III-driven viral small RNAs.

In the VA RNA genes of 43 human adenoviruses, the tetranucleotide pair (GGGU:ACCC) in the central domain is highly conserved, with only one nucleotide diverging (to GGGU:ACCU) in the two groups of type F Ad (Ma et al., 1996). The tetranucleotide pair in BocaSR is of the type F Ad VA RNA (FIG. 11). Mutation of a single nucleotide pair within this sequence drastically decreased the ability of BocaSR to support replication of the HBoV1 DNA (FIG. 3), suggesting that a stem in the central domain is critical for the function (and possibly the structure) of BocaSR.

From the structural perspective, BocaSR more closely resembles the VA RNAs than the EBERs (Tycowski et al., 2015). The predicted structure of BocaSR (FIG. 2C) is comprised of three structural domains: a terminal stem, a central domain, and an apical stem. Each is highly conserved in VA RNAs (Ma et al., 1996). The central domain contains two loop structures that exhibit key functions of VA RNAs (Vachon et al., 2016). Accordingly, in BocaSR, mutations in loop I, the central stem, loop III and the loop III stem, all of which are included in the central domain, diminish the effectiveness of BocaSR in viral DNA replication, with mutations in loop III conferring the most severe defects.

BocaSR shares similarity with the VAI RNA but functions differently. During Ad infection, two distinct VA RNAs, VAI and VAII (about 160 nts long), are expressed, but the VAI RNA (about $10^8$ copies/cell) is more abundant than VAII RNA (Mathews et al., 1991). Of note, BocaSR is expressed at a level similar to that of VAI RNA in the context of VAI gene only (FIG. 9A). VAI RNA plays a regulatory role during the Ad life cycle, enhancing the translation of Ad proteins (Mathews et al., 1995; Ma et al., 19960. It is essential for efficient virus replication, with its deletion from Ad5 leading to an about 20-fold decrease in virus production (Thimmappa et al., 1982).

Figure 9:
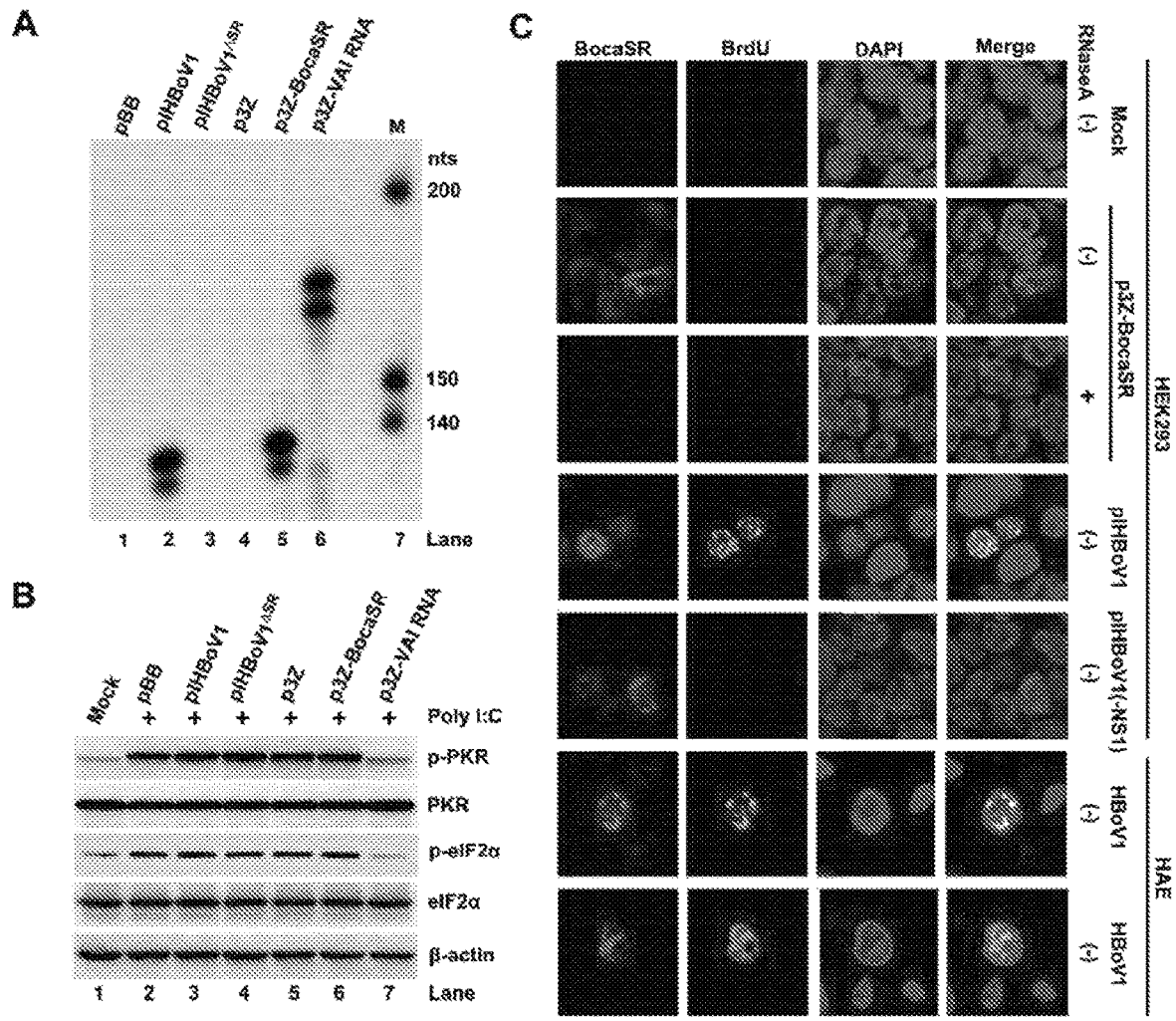
FIGS. 9A-C. BocaSR-facilitated HBoV1 DNA replication in the nucleus does not involve the cytoplasmic PKR pathway. (A&B) Effects of BocaSR on PKR and eIF2α activation. (A) HEK293 cells in wells of a 12-well plate were transfected with 1 μg of pIHBoV1 or other indicated plasmids at the same molar amount to a final 1 μg DNA supplemented with empty p3Z. At 24 hours post-transfection, the cells were transfected with poly I:C at 400 ng/ml for 4 hours using Lipofectamine 2000 (Invitrogen). (A) Total RNA was extracted from the treated cells and was subjected to RNase protection assay with a single probe pBocaSR-VAI RNA. (B) The treated cells were analyzed by Western blotting for levels of PKR and eIF2α proteins and their phosphorylation. Blots were probed with anti-p-eIF2a and anti-p-PRK antibodies and reprobed with anti-PKR, anti-eIF2α, and anti β-actin in order. (C) FISH-IF analysis of BocaSR expression. HEK293 cells were transfected with p3Z-BocaSR, pIHBoV1(-NS1), or pIHBoV1. HAE-ALI cultures were infected with HBoV1. Cells were BrdU-labeled at 48 hours post-transfection or 10 days post-transfection and subjected to FISH-IF analysis. DAPI was used to identify nuclei. Magnification=×100. RNase A-treated transfected HEK293 cells were used as a control. pIHBoV1(-NS1) (20) was transfected as a non-replication control.

VAI RNA binds to PKR and prevents its activation from phosphorylation effect (Mathew et al., 1991; Pe'ery et al., 1963; Rahman et al., 1995). In spite of the similarities between VAI and BocaSR with respect to sequence and structure, it is difficult to imagine that BocaSR acts by the same mechanism because those in which VAI is involved take place in the cytoplasm (Mathews et al., 1995) and BocaSR is present mainly in the nucleus. This is supported by the fact that BocaSR does not inhibit PKR activation (FIG. 9). More importantly, unlike VAI RNA, which non-specifically upregulates translation by inhibiting the phosphorylation of eIF2α through the PKR-eIF2α pathway (Mathews et al., 1991; Schneider et al., 1985, BocaSR specifically upregulates the expression of viral NS1-3 and NP1 protein, but not that of NS4. BocaSR may regulate the processing and export of the NS1-3 and NP1 mRNAs, but not those of the NS4 transcript.

Despite the finding that BocaSR does not inhibit PKR activation, the fact that VAI RNA rescued the defects in expression of HBoV1 nonstructural proteins and partially rescued the replication of viral DNA (about 10%) from BocaSR-deleted pIHBoV1$^{\Delta SR}$ was interesting. It is unlikely that VAI RNA solely functions as an anti-PKR molecule, and that it thereby leads to increased translation of nonstructural proteins and viral DNA replication.

Like EBERs, BocaSR functions in the nucleus. EBV synthesizes two abundant small RNAs, EBER1 and EBER2 (Rosa et al., 1981), that are about 170 nts in size, are highly structured RNA Pol III-transcribed noncoding RNAs, and are abundant in infected cells (about $10^6$/cell) (Tycowski et al., 2015). The EBERs and the VA RNAs share some similarities in function, including the ability to bind the La protein (Rosa et al., 1981) to substitute for the VAI RNA in lytic infection by Ad5 (Bhat et al., 1983), and to bind and inhibit PKR in vitro (Clarke et al., 1990). However, EBERs reside in the nucleoplasm and do not undergo nucleo-cytoplasmic shuttling (Howe et al., 1986; Fok et al., 2006). These observations argue against the physiological relevance of the binding of the nuclear EBERs to PKR, which is present in the cytoplasm. In addition, their structures are quite different from that of the VA RNAs (Tycowski et al., 2015; Glickman et al., 1988). Of note, EBER2 binds to the terminal repeats of the EBV genome and interacts with transcription factor PAX5, acting in concert with it to regulate the expression of a subset of EBV latency genes, thereby playing an important role in replication of the EBV DNA during lytic infection (Lee et al., 2015).

Since the BocaSR resides exclusively in the nucleus and colocalizes with the replicating viral genomes, we speculate that it plays a direct role in replication of the viral DNA, in addition to contributing to the upregulation of viral nonstructural proteins. In this regard, BocaSR may function like EBV-derived EBER2 in interacting with the viral genome.

In summary, BocaSR shares much similarity with VAI RNA at the levels of sequence, secondary structure, and host, yet its nuclear localization and role in the replication of viral DNA are more like those of EBER2. The ability of the VAI RNA to partially complement a BocaSR deficiency highlights a novel role for the former in regulating the expression of viral proteins. Considering that AAV, Ad, and HBoV1 infect the same natural host tissue—the human airway epithelium—it would not be surprising that VAI RNA is capable of exerting some BocaSR functions that have not been discovered. It is likely that both BocaSR and the VA RNAs evolved from cellular tRNA (Schramm et al., 2002) during coinfection of human airways by Ad, AAV and HBoV1. Since HBoV1 replicates autonomously in human airway epithelia, we believe that BocaSR confers the ability to replicate autonomously in non-dividing airway epithelial cells (Deng et al., 2016).

Further, the data show that HBoV1 can serve as a helper virus for AAV productive infection (i.e., replication of the WT virus and packaging of rAAV), and BocaSR is a key functional component in this process. In the absence of helper function from adenovirus, the HBoV1 gene products (minimal requirement: BosaSR, NS4 and NP1) fully support AAV viral DNA replication, and also vector production of rAAV and rAAV/HBoV when the AAV Rep and AAV or HBoV Cap genes are also provided in trans. Thus, the applications of BocaSR include: 1) a target for anti-viral therapies; 2) production of a safer recombinant HBoV1 (rHBoV1) vector, eliminating replication competent virus (RCV) contamination; 3) directed evolution of AAV and/or HBoV1 capsids, using HBoV1 as a helper virus to select and rescue rAAV and/or rHBoV1 genomes from the library-infected cells/tissues of animals; 4) Adenovirus helper independent vector production system for rAAV and rAAV2/HBoV vectors.

Example II

Materials and Methods

Ethics

The use of primary human airway epithelial cells has been approved by Institutional Review Board (IRB) of the University of Iowa (IRB ID No. 9507432).

Cell Lines and Primary Cultures

HEK293 cells (ATCC® CRL-1573™) and HeLa cells (ATCC® CRM-CCL-2™) were cultured in DMEM (Hy-Clone SH30022.01; GE Healthcare Life Sciences, Logan, Utah) supplemented with 10% fetal bovine serum (#F0926, Sigma, St. Louis, Mo.) at 37° C. under 5% $CO_2$ atmosphere. Well-differentiated primary human airway epithelium cultured in air-liquid interface (HAE-ALI) (Transwell inserts; #3470, Corning, Corning, N.Y.) were obtained from the Cell Culture Core of the Center for Gene Therapy, University of Iowa, as described in Huang et al. (2012). HAE-ALI cultures with a transepithelial electrical resistance (TEER) of >1000 $\Omega \cdot cm^2$ were selected for use in this study.

Plasmids Construction (i) pIHBoV1-Based Constructs

The HBoV1 infectious clone plasmid (pIHBoV1) and its mutant pIHBoV1$^{\Delta N1/2}$ which does not express NS1 and NS2 proteins (Huang et al., 2012). pIHBoV1$^{\Delta SR}$ doesn't express BocaSR RNA and pIHBoV1$^{SR(85TG/AC86)}$ that expresses a BocaSR point mutant (Wang et al., 2017).

(ii) pCMV-HBoV1 NSCap-Based Constructs

The pCMV-HBoV1 plasmid that expresses all HBoV1 proteins under the control of CMV promoter (Zou et al., 2016). pCMV-HBoV1$^{\Delta NS1/2}$ that doesn't express NS1 and NS2 proteins and pCMV-HBoV1$^{\Delta NP1}$ that doesn't express NP1 protein were constructed by introducing an early stop codon in the ORF of NS1 and NP1, respectively. pCMV-HBoV1$^{\Delta NS}$ which abolishes expression of all the NS1-4 proteins by replacing the D1-A1 intron with the IV intron of Epo gene (Yan et al., 2000). pCMV-HBoV1$^{\Delta VP}$ and HBoV1$^{\Delta NS1/2\Delta VP}$ were constructed by introducing a large deletion in the VP ORF using Mfe I digestion followed by self-ligation of the pCMV-HBoV1 and pCMV-HBoV1$^{\Delta NS1/2}$, respectively.

(iii) pcDNA3.1-Based Constructs pcDNA3.1-FLAG-NP1 (pNP1), which expresses N-terminally FLAG-tagged HBoV1 NP1, was constructed by inserting a codon-optimized HBoV1 NP1 ORF into pcDNA3.1-FLAG vector (Wang et al., 2015) using EcoR I and Xho I sites. pcDNA3.1-Myc-NS3 (pNS3) and pcDNA3.1-Myc-NS4 (pNS4) were constructed by inserting N-terminally Myc-tagged codon-optimized HBoV1 NS3 and NS4, respectively, into pcDNA3.1-Myc vector (Wang et al., 2015) using EcoRI and XhoI sites. pcDNA3.1-Myc-NS4-P2A-NP1 (pNS4-NP1) was constructed by inserting a coding sequence of NS4-P2A (a porcine teschovirus-1 peptide)-NP1 into pcDNA3.1-Myc vector using EcoR I and Xho I sites.

(iv) pGEM-3Z Based Constructs pGEM-3Z-BocaSR (pBocaSR) which expresses the HBoV1 noncoding RNA BocaSR (Wang et al., 2017).

(v) pLenti-CMV Based Constructs pLenti-CMV-HBoV1 NS1, NS2, NS3, NS4, which express codon-optimized HBoV1 NS1, NS2, NS3, and NS4 proteins, respectively (Deng et al., 2016).

(vi) Adenovirus pHelper Plasmid pHelper, which contains Ad5 E2, E4, and VA genes, was purchased from Agilent Technologies (Santa Clara, Calif.).

(vii) AAV2 Duplex Genome-Containing Plasmid (Infectious Clone) SSV9

SSV9 (pSub201), which contains a full-length AAV2 genome, is an infectious clone of AAV2, was a gift from Dr. R. J. Samulski at University of North Carolina, Chapel Hill (Samulski et al., 1989; Qiu et al., 2002)

Plasmids DNA Transfection

HEK293 cells and HeLa cells seeded in 60-mm dishes were transfected using the LipoD293 or GenJet™ transfection reagent (SignaGen Laboratories, Gaithersburg, Md.) following the manufacturers' instructions. The total amounts of plasmid DNA were kept constant (4 µg per 60-mm dish) in each group by supplementing empty vector to balance transfection efficiency.

Virus and Infection

HBoV1 and AAV2 were produced as described in Huang et al. (2012). Briefly, HEK293 cells were transfected with pIHBoV1, or SSV9 plus pHelper or HBoV1 helper plasmids using PEI MAX (Polysciences, Warrington, Pa.). The cells were collected at 72 h post-transfection, lysed and treated with excessive DNase I. The clarified cell lysates were subjected to cesium chloride gradient ultra-centrifugation. Virus-enriched fractions were collected, dialyzed against PBS (pH7.4) buffer, and quantified by real-time PCR. The titers were determined as DRP/µL. The final virus stocks were kept at −80° C. freezer. Ad5 (dl309) was propagated in HEK293 cells (Qiu et al., 2002) and purified by cesium chloride density gradient centrifugation following a protocol in (Luo et al., 2007). Ad5 titer was determined as plague forming units (PFU).

HAE-ALI cultures were infected with HBoV1 at a multiplicity of infection (MOI) of 100 DRP/cell, with AAV2 at an MOI of 3,000 DRP/cell, with Ad5 at an MOI of 0.5 PFU/cell. All viruses were diluted in 50 µL culture medium and inoculated at the apical side for 4 h. HEK293 and HeLa cells were infected with AAV2 at an MOI of 100 DRP/cell or otherwise specified in figure legends. Virus (AAV2) was diluted in DMEM medium and incubated with the cells at 37° C. for 4 h, then the cells were washed once with PBS and fed with fresh medium, followed by transfection at 12 h post-infection.

Quantification of Virus Production

HEK293 cells seeded in a 6-well plate were transfected with SSV9 or infected with AAV2 in the presence of Ad pHelper or HBoV1 helper genes. The cells were lysed with fresh sodium deoxycholate lysis buffer (25 mM Tris pH8.0, 150 mM NaCl, 2 mM $MgCl_2$, 0.5% sodium deoxycholate). The cell lysate was treated with Benzonase® Nuclease (250 U/mL) for 2 h at 37° C. to digest free nucleic acids. The reaction was stopped by adding EDTA to 10 mM and further digested with protease K for viral DNA extraction using DNeasy Blood & Tissue kit (Qiagen, Germantown, Md.), following the manufacturers instructions. Viral genome numbers were determined by real-time PCR as DNase (nuclease) digestion-resistant particles (DRP) and normalized to each cell.

Real-Time PCR

For AAV2, forward primer, 5'-TCT GCA GCT CCC ACT CGA T-3' (SEQ ID NO: 27), reverse primer, 5'-TTT GCT TCC TTC ATC ACA CAG TAC T-3' (SEQ ID NO:28), and probe, 5'/56-FAM/TCC ACG CTG/ZEN/ACC GTG TCC CG/3IABkFQ/-3' (SEQ ID NO:29), purchased from IDT (Coralville, Iowa), were used. The primers and probe for HBoV1 genome quantification (Huang et al., 2012).

Western Blotting

Cells were directly lysed in 2×Laemmli sample buffer and boiled at 95° C. for 5 min. The cell lysates were then loaded and separated in 10% SDS-PAGE gel. Proteins were transferred onto a PVDF membrane (#IPVH00010, Millipore Bedford, Mass.), which was blocked and probed with primary and secondary antibodies sequentially. Signals were visualized by enhanced chemiluminescence, and images were acquired using ImageQuant™ LAS 4000 biomolecular imager (GE Health Life Sciences, Pittsburgh, Pa.).

Antibodies Used

Antibodies against HBoV1 NS1C, NP1, and VP proteins have been described (Chen et al., 2010). The following antibodies were purchased: anti-AAV2 Rep (clone 303.9, #03-65169) and anti-AAV2 VP (clone A69, #03-61057) from American Research Products Inc. (Waltham, Mass.); anti-FLAG tag (#F1804) and anti-β-actin (#A5441) from Sigma (St Louis, Mo.), anti-Myc tag (clone 9E10, #sc-40)

from Santa Cruz biotechnology; and anti-RPA32(pT21) (clone EPR2846(2), #ab109394) from Abcam (Cambridge, Mass.).

Hirt DNA Extraction and Southern Blotting

Low molecular h Hirt) DNA extraction: Cells were washed once with PBS and lysed with Hirt lysis buffer (10 mM Tris pH 8.0, 10 mM EDTA, 0.6% SDS) for 15 min. Cell lysates were transferred into Eppendorf tubes, adjusted to a final NaCl concentration of 1.5 M, and incubated on ice overnight before cleared by centrifugation at 17,000 g for 20 min. The supernatants were collected and treated with protease K at a final centration of 1 mg/mL for 1 h. Hirt DNA was purified with DNA extraction kit (Qiagen) following the manufacturer's instructions. For Hirt DNA extracted from transfected cells, Dpn I was used to digest input DNA before Southern blotting.

Southern blotting: Southern blotting was performed according to Guan et al. (2009). Briefly, the Hirt DNA samples were digested with Dpn I, resolved into 1% agarose gel, blotted onto nitrocellulose membrane, and probed with a $^{32}$P-dCTP-labeled probe. The template of the AAV2 probe was the Xba I/Nde I-digested 4.3 kb of AAV2, which contains AAV2 Rep- and VP-encoding sequence. The HBoV1 probe was made as previously described (8) Hybridization signals were captured by a storage phosphor screen and visualized on a Typhoon™ FLA 9000 biomolecular imager (GE Healthcare).

HBoV1 and AAV2 Co-Infection Rescues Productive Infection of AAV2 in Well-Differentiated Human Airway Epithelium (HAE)

Figure 17:
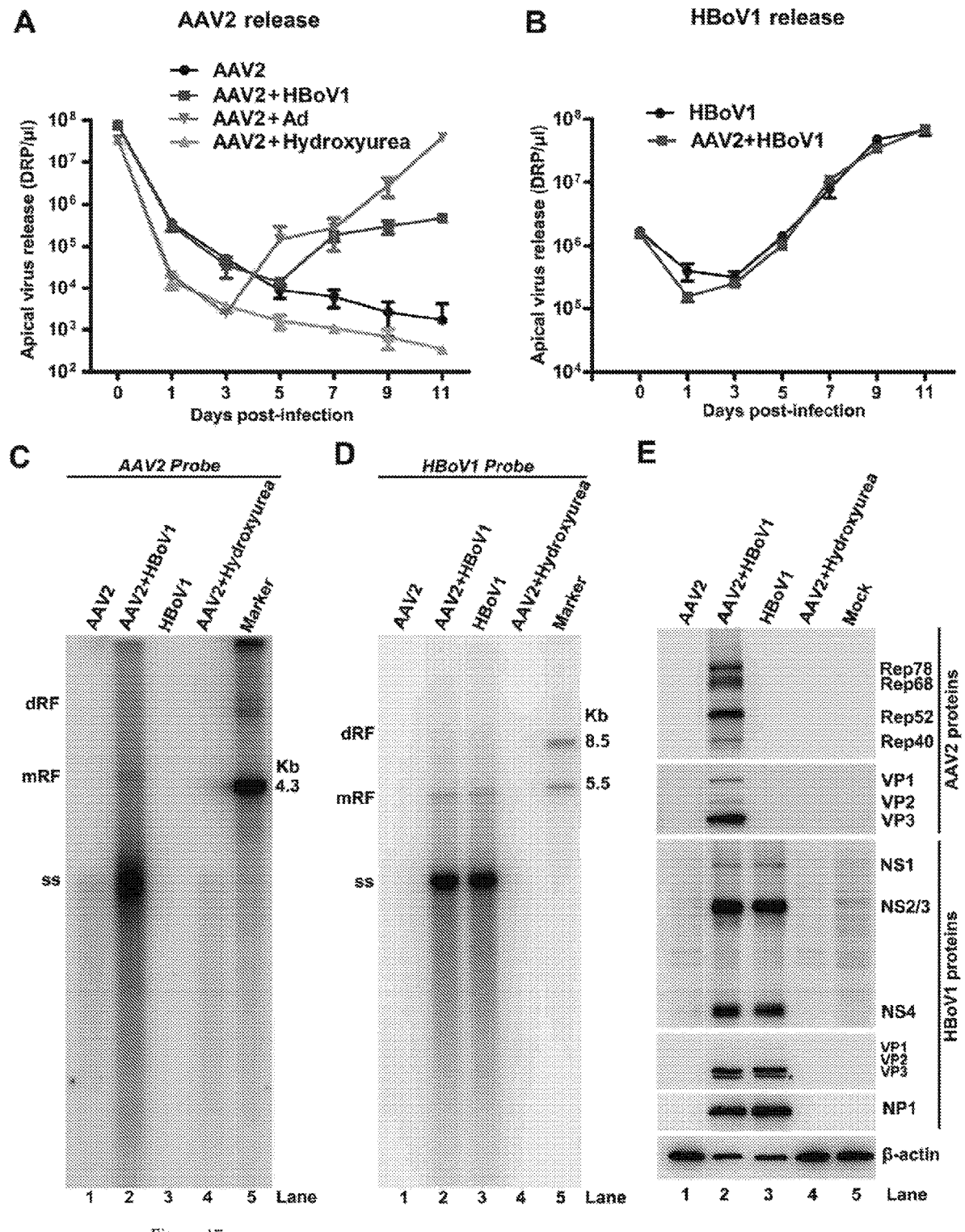
FIGS. 17A-E. HBoV1 rescues AAV2 replication in HAE-ALI cultures. (A) AAV2 virus release kinetics. HAE-ALI cultures were infected with AAV2 in the presence of HBoV1 or Ad5 co-infection, or treated with hydroxyurea at a final concentration of 2 mM. The apical released virions were collected every other day and measured by real-time PCR. Virus titers are shown as DRP/μL. (B) HBoV1 virus release kinetics. HAE-ALI cultures were infected with HBoV1 alone or co-infected with AAV2. HBoV1 virions released were measured by real-time PCR and are shown as DRP/μl. (C&D) Southern blot analysis of AAV2 and HBoV1 DNA replication. At 11 days post-infection or post-treatment of hydroxyurea, as indicated. 90% of the collected cells were lysed for Hirt DNA extraction. Hirt DNA samples were analyzed by Southern blotting with a $^{32}$P-labelled AAV2 probe (C) or a $^{32}$P-labelled HBoV1 probe (D). Dimer replicative form (dRF), monomer replicative form (mRF), and single-stranded DNA (ssDNA) are indicated. An AAV2 DNA at 4.3 kb (C) and HBoV1 DNA fragments at 5.5 kb and 8.5 kb (D) were used as size markers. (E) Western blot analysis of AAV2 and HBoV1 proteins. At 11 days post-infection or post-treatment of hydroxyurea, as indicated. 10% of the collected cells were lysed and immunoblotted with anti-AAV2 Rep, anti-AAV2 VP, anti-HBoV1 NS1C, anti-HBoV1 VP3, anti-HBoV1 NP1, and anti-β-actin antibodies. Proteins detected are indicated next to the images. Asterisk indicates a possible cleaved VP3 protein.

Since AAV2 has been reported to replicate in well-differentiated mitotically quiescent cells (Meyers et al., 2000), similar to HBoV1 (Deng et al., 2016), and Ad and HBoV1 both infect HAE-ALI (Huang et al., 2012; Kotha et al., 2015), it was hypothesized that HBoV1 would facilitate AAV2 replication in non-dividing HAE cells. To test this hypothesis, HAE cells of HAE-ALI were infected with AAV2, in the presence or absence of HBoV1 or Ad helper. Apically released viruses were collected every other day and quantified. As expected, infection with AAV2 alone did not lead to replication of virus in HAE cells, as shown by the continually drop in detectible AAV2 (DNase-resistant particles (DRP)/μL) in the apical washes following infection (FIG. 17A, AAV2). Notably, HBoV1 co-infection rescued AAV2 replication. Apically released AAV2 virions rose after day 5 post-infection (FIG. 17A, AAV2+HBoV1), consistent with HBoV1 lytic spread and replication of virus within the culture (FIG. 17B, HBoV1 alone). As a positive control, Ad rescued AAV2 infection much more efficiently (about 1-2 log higher) and two days earlier than HBoV1 (FIG. 17A, AAV2+Ad). This observation suggests that HBoV1 is a modest helper virus for AAV2 replication in comparison with Ad. However, treatment of HAE-ALI cultures with DNA damage-inducing reagent (hydroxyurea) failed to rescue AAV2 replication (FIG. 17A, AAV2+hydroxyurea). At 11 days post-infection, infected cells were collected for analysis of viral DNA and proteins. Typical AAV2 DNA replicative forms, dimer replicative form (dRF), mono replicative form (mRF), and ssDNA were observed only in the cells coinfected with HBoV1 (FIG. 17C, lane 2 vs lanes 1 and 4); however, these forms were about 2-log less than that observed following Ad co-infection, despite a similar ratio of viral ssDNA vs mRF DNA (data not shown). Consistent with virus replication, AAV2 non-structural (Rep) and structural (VP) proteins were expressed only in cells co-infected with HBoV1 and AAV2 (FIG. 17E, lane 2, Rep and VP).

Previously, it was reported that during AAV2/Ad co-infection, Ad replication was inhibited (Timpe et al., 2006). In this study HBoV1 DNA replication was observed in the cells co-infected with HBoV1 and AAV2. As shown in FIG. 17B for apical virus release, in FIG. 17D for HBoV1 replicative DNA forms, and in FIG. 17E for HBoV1 proteins, there were no large differences between with or without AAV2 co-infection.

Collectively, these results demonstrated that HBoV1 is a helper virus for productive AAV2 infection in well-differentiated HAE cells; however, AAV2 infection does not affect HBoV1 infection.

HBoV1 NP1, BocaSR and NS4 Genes Function as Essential Helper Components for Replication of AAV2 Duplex Genome in HEK293 Cells Next it was investigated whether this helper function depends on HBoV1 replication or only on viral gene expression. Due to the inefficiency of DNA transfection of HAE cells in polarized HAE-ALI, AAV2 DNA replication in HEK293 cells was tested by co-transfecting a duplex AAV2 genome (SSV9, an infectious clone of AAV2) (Samulski et al., 1989) and various HBoV1 gene-expressing plasmids. Co-transfection of SSV9 with plasmid Ad pHelper, which expresses necessary adenovirus helper genes, i.e., E2a, E4, and VA RNA, served as a positive control. The results showed that co-transfection of pIHBoV1, an HBoV1 duplex DNA genome (an infectious clone) (Huang et al., 2012) rescued AAV2 DNA replication as efficiently as co-transfection of Ad pHelper in HEK293 cells (FIG. 18A, lanes 3 vs 2), although pIHBoV1 gave rise less expression of AAV2 Rep and VP genes than Ad pHelper (FIG. 18C, lanes 3 vs 2). Mutagenesis analysis revealed that BocaSR was essential for AAV2 DNA replication. The helper function of HBoV1 for AAV2 was significantly reduced when BocaSR was deleted (pIHBoV1$^{\Delta SR}$) or mutated (pIHBoV1$^{SR(85TG/AC86)}$) (FIG. 18A, lanes 4 and 5).

Next, the HBoV1 genes that facilitate AAV2 DNA replication were dissected. First, pIHBoV1$^{\Delta NS1/2}$, a replication deficient mutant (Huang et al., 2012), was chosen to examine the role of HBoV1 NS1/NS2 in this function. Prevention of NS1 and NS2 expression didn't abrogate the helper function of HBoV1 for AAV2 DNA replication (FIG. 18A, lanes 3 vs 6), and AAV2 protein expression (FIG. 18C, lanes 3 vs 6). Thus, these results demonstrated that the helper function of HBoV1 for AAV2 does not rely on HBoV1 DNA replication, but rather on HBoV1 gene expression. However, HBoV1 NS1 and NS2 were not essential for helping AAV2 DNA replication in HEK293 cells following transfection of the AAV2 duplex genome.

Next the contribution of NS3 and NS4 proteins in helping AAV2 DNA replication was examined by transfecting a NS1-4-null plasmid (pCMV-HBoV1$^{\Delta NS}$) (FIG. 18D, lane 3). AAV2 DNA replication was significantly reduced when NS3 and NS4 protein expression were further prevented (FIG. 18B, lanes 2 vs 3), suggesting that either NS3 or NS4 protein was involved in helping AAV2 DNA replication. To clearly define which NS protein was involved, pCMV-HBoV1$^{\Delta NS}$ was replenished with NS3 and NS4 genes, respectively. Southern blot analysis revealed that NS4, but not NS3, restored the function of pCMV-HBoV1$^{\Delta NS}$ for supporting AAV2 DNA replication (FIG. 18B, lanes 3 vs 5). Therefore, NS4 was a HBoV1 helper gene for supporting AAV2 DNA replication.

Further mutagenesis studies revealed that NP1 supported AAV2 DNA replication. There was little AAV2 RF DNA detected when NP1 was not expressed (FIG. 18B, lane 6). Furthermore, HBoV1 VP proteins had negligible functions in AAV2 DNA replication. AAV2 DNA replicated at the similar efficiency in the presence or absence of HBoV1 capsid protein expression (FIG. 18B, lanes 2 vs 7).

Taken together, HBoV1 genes, NP1, BocaSR, and NS4 were identified as helper genes for AAV2 DNA replication in HEK293 cells. The study was extended to address whether these three genes were sufficient to facilitate AAV2 replication individually or together in an orchestrated manner.

HBoV1 NP1, NS4, and BocaSR Compose the Minimal Set of the HBoV1 Helper Genes for DNA Replication of the AAV2 Duplex Genome in Transfected HEK293 Cells The effects of the three HBoV1 helper genes were tested alone and in various combinations on AAV2 DNA replication and protein expression. The results showed that expression of individual genes (NP1, NS4, or BocaSR) did not facilitate AAV2 DNA replication (FIG. 19A, lanes 3-5). Simultaneous expression of any two genes only slightly stimulated AAV2 DNA replication (FIG. 19A, lanes 6-8), but less efficiently than the maximum DNA replication that was achieved when all three genes were expressed (FIG. 19A, lanes 9 vs 2). As for the protein expression, BocaSR, but not NP1 and NS4, stimulated AAV2 Rep78 and Rep52 expression (FIG. 19B, lanes 5 vs 3&4). Notably, the BocaSR induced Rep expression was not sufficient to initiate AAV2 DNA replication (FIGS. 19A&B, lane 5).

The helper function of Ad pHelper vs HBoV1 Helper (a set of three plasmids: pNP1+pNS4+pBocaSR) was also compared in virus production, which was measured by real-time PCR and normalized to DRP per cell. Ad pHelper supported AAV2 production most efficiently with an average virus titer of $4.6 \times 10^4$ DRP/cell, whereas HBoV1 Helper supported AAV2 production was five- to eight-fold less than the Ad pHelper (FIG. 18C). We reasoned that the lower progeny production might be the result of the low expression of AAV2 capsid proteins facilitated by the HBoV1 Helper (FIG. 17C, lanes 2 vs 3 and 6). The progeny virus infectivity was also examined, as shown in FIG. 18D. The AAV2 produced with HBoV1 Helper (pNP1+pNS4+pBocaSR) infected HEK293 cells as efficiently as that produced with Ad pHelper.

Thus, HBoV1 NP1, NS4, and BocaSR are a set of minimal helper genes, whose expression supports AAV2 DNA replication and progeny virus production from transfection of the AAV2 duplex genome in HEK293 cells.

HBoV1 Minimal Helper Genes Support AAV2 DNA Replication in HeLa Cells, Independent of Expression of Any Ad Genes Considering HEK293 cells express Ad E1 gene, the helper function of HBoV1 to support AAV2 DNA replication in HeLa cells was tested. In the AAV2 duplex genome-transfected HEK293 and HeLa cells, co-transfections with HBoV1 helper genes or Ad pHelper were compared, and Ad infection served as a positive control. HBoV1 helper genes, provided from pCMV-HBoV1$^{\Delta NS1/2\Delta VP}$ which expressed HBoV1 NP1, NS4, and BocaSR, as well as NS3 (FIG. 19B, lane 2), stimulated AAV2 DNA replication as efficiently as Ad pHelper or Ad infection (at 1 MOI) in HEK293 cells (FIG. 20, lanes 2 vs 3 and 4). As expected, transfection of Ad pHelper did not result in any RF AAV2 DNA in HeLa cells (FIG. 20, lane 7), because the Ad E1 gene is not expressed in HeLa cells. Importantly, HBoV1 helper genes (NP1, NS3, NS4, and BocaSR) supported AAV2 DNA replication as efficiently as Ad infection in HeLa cells (FIG. 20, lanes 6 vs 8), although the overall level of AAV2 RF DNA was lower in HeLa cells than in HEK293 cells (FIG. 20, HeLa vs HEK293). The virus produced from HeLa cells was infectious, and had a yield of about 800 DRP/cell. Later, it was proved that expression of NP1, NS4, and BocaSR genes was sufficient to rescue AAV2 DNA replication in HeLa cells (FIG. 23C, lane 2).

Together, the above results suggested that HBoV1 helper genes NP1, NS4, and BocaSR facilitate AAV2 DNA replication in both HeLa and HEK293 cells without requirement of Ad E1 gene expression.

HBoV1 NS2 Protein is Required for AAV2 Genome Replication in HEK293 and HeLa Cells Following Infection with AAV2 Virions Next the minimal HBoV1 helper genes in supporting productive AAV2 infection in HEK293 and HeLa cells were examined. Instead of transfection with infectious plasmid SSV9, HEK293 or HeLa cells were infected with AAV2, and analysis of DNA replication and protein expression of both AAV2 and HBoV1 were conducted following the transfection of HBoV1 helper genes. The results showed that HBoV1 helper genes (NP1+NS4+BocaSR) could not efficiently complement AAV2 DNA replication in HEK293 cells, compared with that from Ad pHelper (FIG. 21A, lanes 3 vs 2). The addition of NS3 gene by transfection of pLenti-NS3 plasmid (FIG. 6B, lane 4, NS2/3) had no amendment of effects (FIG. 21A, lane 4). Importantly, additional expression of NS2 protein (FIG. 21B, lane 5, NS2/NS3) from the transfection of pLenti-NS2 or pCMV-HBoV1$^{\Delta VP}$ that expresses all HBoV1 nonstructural proteins, significantly enhanced AAV2 DNA replication (FIG. 21A, lanes 5 and 7 vs 3) and protein expression (FIG. 21B, lanes 5 and 7 vs 3, Rep and VP). It was remarkable that the level of AAV2 DNA replication facilitated by the additional NS2 was similar to that supported by Ad pHelper (FIG. 21A, lanes 5 and 7 vs 2).

Additional expression of NS1 only slightly increased AAV2 DNA replication and protein expression in HEK293 cells (FIG. 21A, lane 6 and FIG. 6B, lane 6). As NS1 induces a DDR in HEK293 cells (FIG. 21B, lane 6) (Deng et al., 2016), hydroxyurea was used to induce a DDR, as shown by the increased expression of phosphorylated RPA32 (p-RPA32) (FIG. 21B, lanes 8 and 9). However, hydroxyurea treatment did not obviously increase AAV2 DNA replication (FIG. 21A, lanes 8 and 9), which echoes to the no helper function in hydroxyurea-treated HAE cells. Thus, these results suggested that HBoV1 helper supported AAV2 replication independently of DDR signaling.

The same experiments were performed in HeLa cells, and similar results were obtained. As shown in FIG. 21C (lanes 4 and 6 vs 2, 3, and 5) and FIG. 21D (lanes 4 and 6 vs 2, 3, and 5), co-expression of NS2 stimulated AAV2 DNA replication and protein expression following AAV2 infection in the presence of NP1, NS4, and BocaSR genes. It was noted that the overall level of AAV2 DNA replication in HeLa cells was lower than that in HEK293 cells during infection (FIG.

21A vs FIG. 21C). As noted, extended exposure time was required in the Southern blot shown in FIG. 21C to visualize the AAV2 DNA replication.

Taken together, the results demonstrated that HBoV1 NS2 protein plays a role in AAV2 DNA replication during AAV2 infection, in addition to NP1, N54, and BocaSR.

Figure 16:
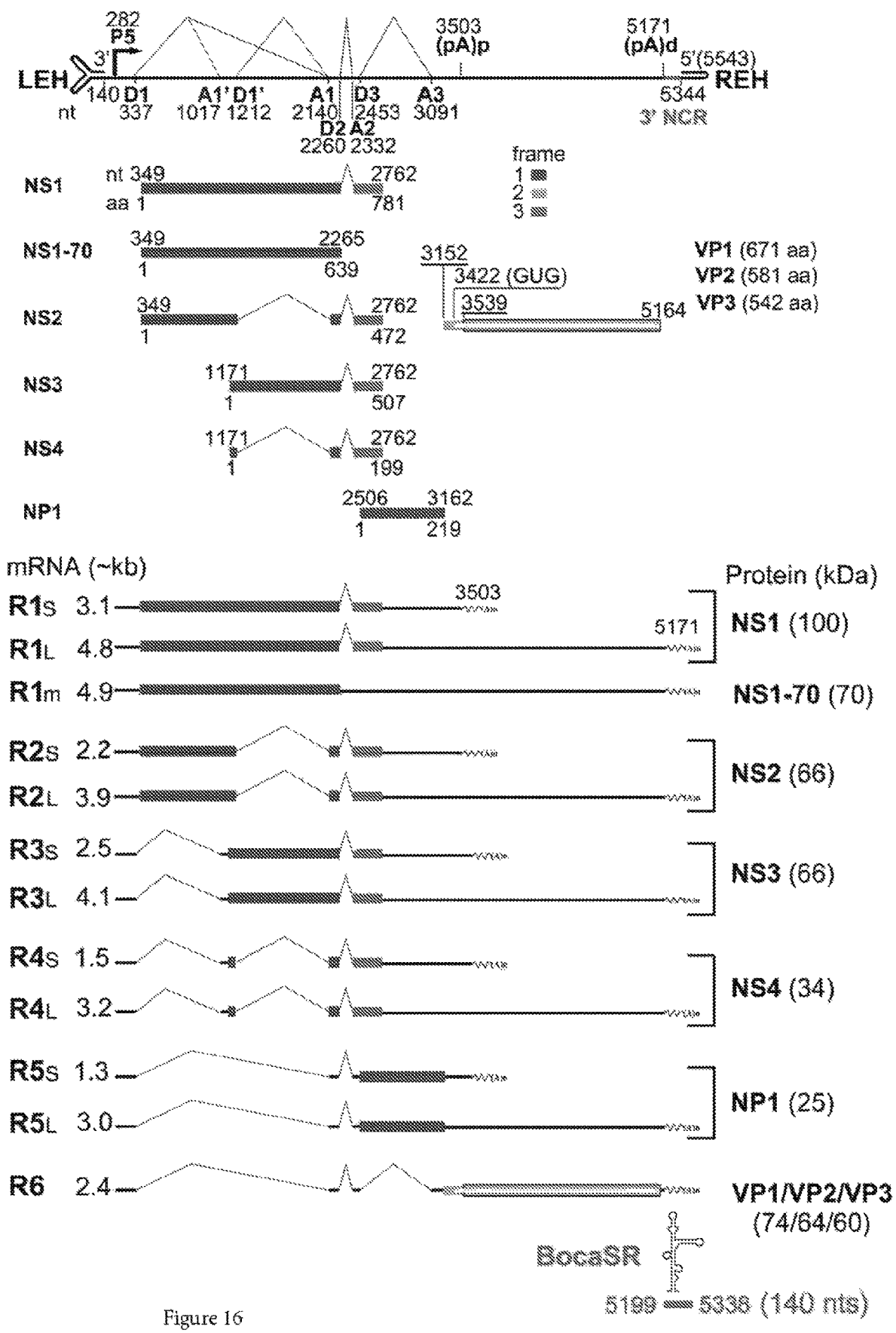
FIG. 16. Genetic map of HBoV1. The HBoV1 single-stranded (ss) DNA genome is shown in negative sense, along with its transcriptional and post-transcriptional units: the P5 promoter, 5' splice-donor sites (D1, D1', D2, and D3) and 3' splice-acceptor sites (A1, A1', A2, and A3), the proximal polyadenylation site [(pA)p] and distal polyadenylation site [(pA)d], and the 3' non-coding region (NCR). The left-end hairpin (LEH) and right-end hairpin (REH) structures of the genome are shown. Six groups of major HBoV1 mRNA transcripts are shown with either long-form mRNA (RX$_L$) that reads through the (pA)p site or short-form mRNA (RXs) that is polyadenylated at the (pA)p site. R1 mRNA has a minor species (R1m) that is unspliced at the central small intron (D3-A3) and encodes a minor protein NS1-70. Major open reading frames (ORFs) are depicted as colored boxes, with the nucleotide numbers (nt) and amino acids (aa) at the start and stop codons indicated. Proteins expressed from each mRNA are indicated beside their respective mRNA transcript (molecular weight in kDa). A bocaviral noncoding small RNA (BocaSR) is transcribed from the 3' NCR of nt 5199-5338 as indicated.

NS2 Substitutes for NS4 in Supporting AAV2 DNA Replication Both Following Transfection of AAV2 Duplex Genome and AAV2 Infection The majority of NS4 coding sequence is the TAD domain of NS1, and the four non-structural protein at the left side of HBoV1 genome, NS1, NS2, NS3, and NS4, share this TAD domain in the C-terminus (FIG. 16) (Shen et al., 2015). It was hypothesized that the addition of helper function from NS4 expression was redundant in the presence of NS2 during AAV2 infection. To this end, HEK293 cells were transfected with an AAV2 duplex genome and various combinations of HBoV1 helper genes, and, in parallel, HEK293 cells were infected with AAV2 and transfected with HBoV1 helper genes. Analysis of AAV2 DNA replication showed that, NS2, NP1, and BocaSR combination supported AAV2 DNA replication as efficiently as the combination of NS4, NP1, and BocaSR genes (FIG. 22A, lanes 4 vs 3), suggesting that the function of NS4 can be fully replaced by NS2 for AAV2 DNA replication following transfection, although the function of the OBD domain of NS2 is not required. As expected, the combination of NP1 and BocaSR with NS2, but not with NS4 gene, efficiently supported viral DNA replication in AAV2-infected HEK293 cells (FIG. 22A, lanes 8 vs 7), which was at a level similar to that supported by Ad pHelper (FIG. 22A, lanes 8 vs 6). However, the expression level of AAV2 proteins in the groups of HBoV1 helper genes were less than that in the Ad pHelper group, in particular, the VP proteins (FIG. 22B, lanes 4 vs 2 and lanes 8 vs 6).

In parallel, the same experiments were conducted in HeLa cells, and similar results were observed. As shown in FIG. 22C (lanes 3 vs 2) and FIG. 22D (lanes 3 vs 2), NS2 fully replaced NS4 in supporting AAV2 DNA replication following transfection. However, following AAV2 infection, NS2, but not NS4, in combination with NP1 and BocaSR, rescued AAV2 DNA replication and protein expression efficiently (FIGS. 22C&D, lanes 5 vs 6). These results demonstrated that a combination of helper genes (NP1, NS2, and BocaSR) supported efficient AAV2 DNA replication not only following transfection but also during AAV2 infection. However, the gene combination of NP1, NS2, and BocaSR helped the production of progeny virions was less (about 1 log) than that produced by Ad pHelper in HEK293 cells (FIG. 23A), which is likely due to the insufficient expression of AAV2 capsid proteins (FIG. 22B, lane 8, VP). In HeLa cells, virus production was at the similar level as that in HEK293 cells in the presence of NP1, NS2, and BocaSR, as well as in the presence of NP1, NS4, and BocaSR (FIG. 23B).

Taken together, the results confirmed that the combination of HBoV1 NP1, NS2, and BocaSR genes is the minimal and full helper for AAV2 DNA replication, and also is the minimal helper for AAV2 infection.

Discussion

In this study, HBoV1 was shown to serve as a helper virus for AAV2. This is the first example of an autonomous parvovirus facilitating replication of a dependoparvovirus. HBoV1 triggered AAV2 replication during co-infection in HAE-ALI. The minimal HBoV1 products required to support replication of the AAV2 genome are NP1, NS4, and BocaSR (HBoV1 Helper I). By contrast, HBoV1 products required to support production of AAV2 virions include are NP1, NS2, and BocaSR (HBoV1 Helper II). Importantly, this provided an alternative and simple system to replicate the AAV2 genome in non-Ad E1-expressing cells. The HBoV1/AAV2 helper system can be used to pinpoint the functions of HBoV1 genes by comparison with the Ad/AAV2 system, as many of the functions of Ad genes have already known.

Helper functions. Productive AAV2 infection requires a helper virus or treatment with genotoxic reagent in proliferating cells (Ward, 2006). Different helper viruses or genotoxic reagents help to facilitate productive AAV2 infection through various mechanisms. The HSV1 (human herpesvirus 1) minimal genes required for AAV2 replication are helicase/primase complex (UL5, UL8, UL52) and DNA binding protein ICP8 (Weindler et al., 1991). It was suggested that, in the HSV1 helper system, AAV2 DNA replication utilizes HSV1-coded viral DNA polymerase (Alazrd-Dany et al., 2009) rather than cellular DNA polymerases, which are used when Ad helper is present ((Ni et al., 1998). It has been recently shown by the Xiao lab (Moore et al., 2015) that although vaccinia virus can also serve as a helper for AAV replication (Schlehofer et al., 1986), however, in this case it is not a full helper because it does not activate AAV promoters. Thus vaccinia can only drive AAV replication and packaging when all AAV promoters are already activated ((Moore et al., 2015) In this study, it was observed that HBoV1 is a less efficient helper for AAV2 than Ad following infection in HAE-ALI; there were 2-log less AAV2 virions released from AAV2/HBoV1 co-infected HAE-ALI than that from AAV2/Ad co-infected HAE-ALI (FIG. 17A). As HBoV1 infected nearly 80% of the HAE cells of the HAE-ALI as detected by NS1 expression (data not shown), it is speculated that HBoV1 is a modest helper for AAV2 replication. However, unlike HBoV1, AAV2 poorly transduces the apical surface HAE-ALI due to an intracellular block nuclear translocation (Moore et al., 2015). Thus, the inefficient AAV2 helper function of HBoV1 could be influenced by the inability of HBoV1 to enhance nuclear translocation of AAV2, unlike Ad that enhances AAV2 transduction by promoting nuclear translocation (Xiao et al., 2002). Thus, it is possible that HBoV1 could more efficiently support replication of alternative AAV serotypes (e.g., AAV1) that transduce HAE-ALI at greater efficiency (Yan et al., 2006).

As a helper virus for AAV2 replication, there are similarities in the helper functions between Ad and HBoV1. Firstly, these two helper viruses both infect differentiated HAE cells (Huang et al., 2012; Kotha et al., 2015). Secondly, AAV2 replication in the presence of Ad or HBoV1 utilizes cellular DNA polymerases (Nash et al., 2017). HBoV1 does not express DNA replication polymerase, and its replication largely relies on cellular repair polymerases of Y-family (Deng et al., 2016; Deng et al. 2016). Thirdly, both Ad and HBoV1 helpers use viral encoded noncoding RNAs, VA RNA and BocaSR, respectively, which share an identity of 50% in sequence and a high similarity in structure (Wang et al., 2016).

While DNA damage-inducing agents were previously claimed to help AAV2 replication (Yalkinoglu et al., 1988), a significant increase in AAV2 DNA replication was not observed when the cells were treated with hydroxyurea, which is likely because the hydroxyurea-stimulated AAV2 replication was weak, compared with Ad or HBoV1 helper (Yalkinoglu et al., 1988). Apparently, HBoV1-facilitated AAV2 replication is independent of DNA damage response signaling, as the HBoV1 DDR inducer NS1 protein was not required for AAV2 replication (Deng et al., 2016).

Figure 18:
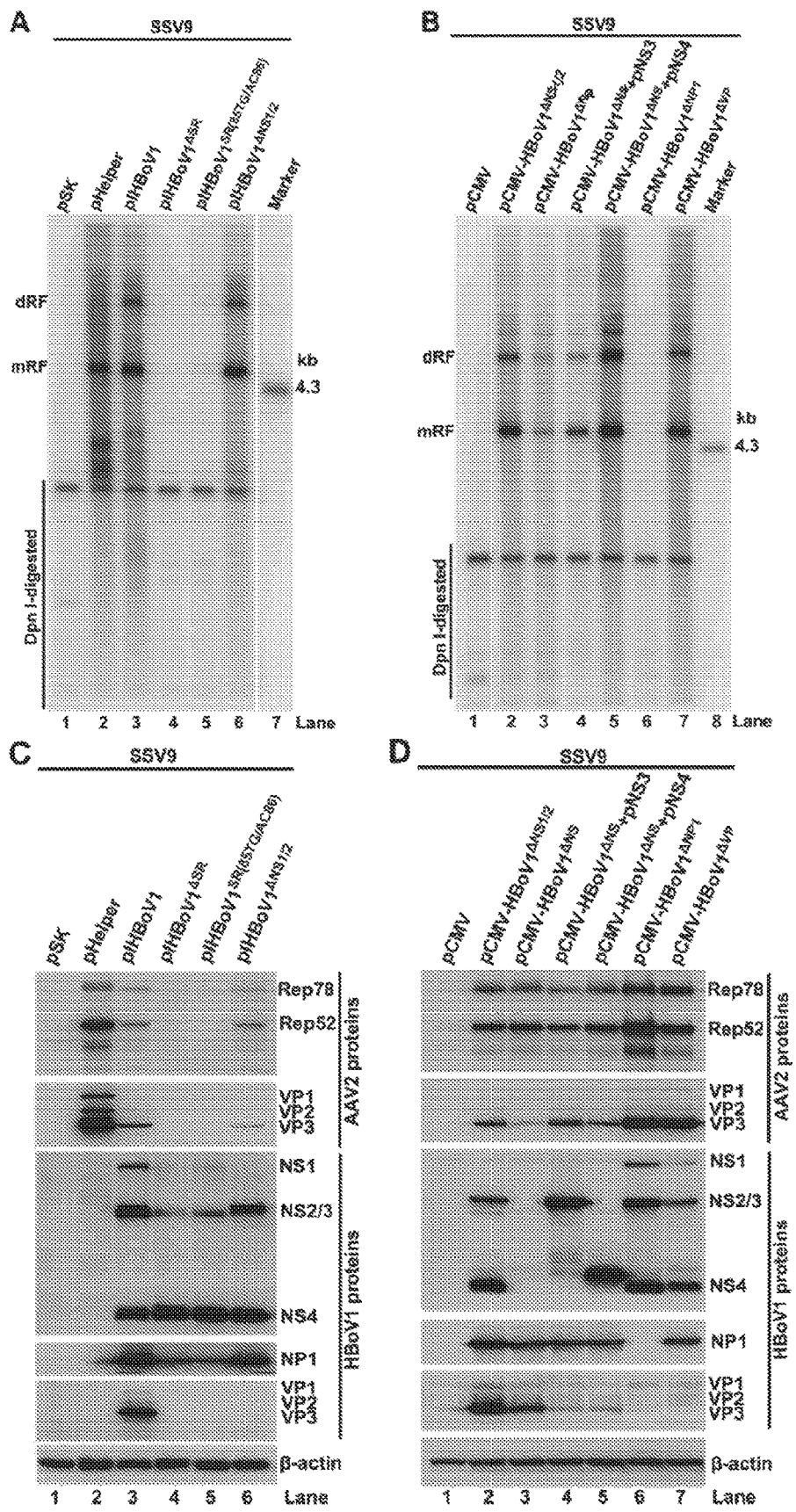
Figure 19:
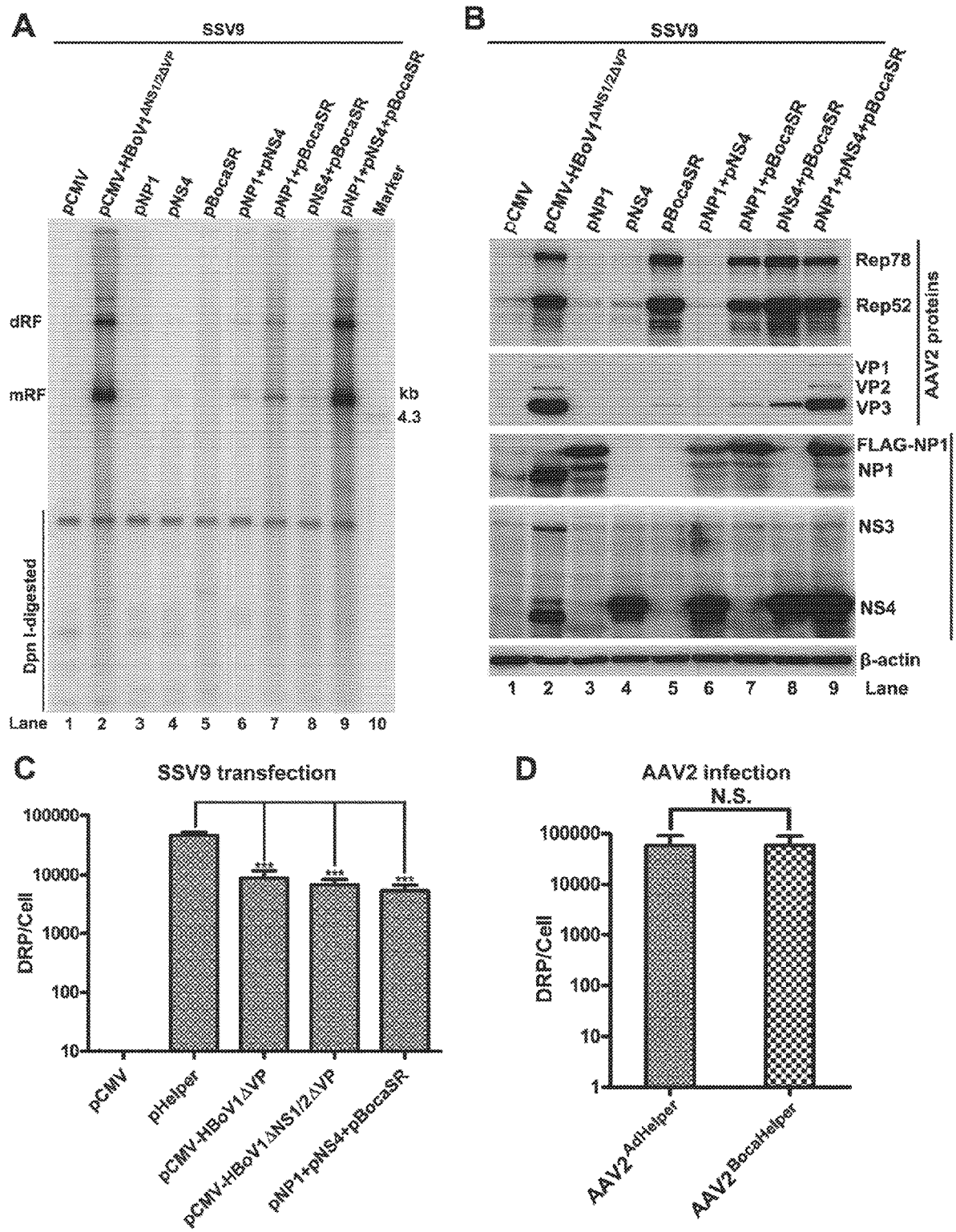

Helper function in viral DNA replication vs virus production. HBoV1 helper produced tenfold less virus than Ad pHelper (FIG. 19C and FIG. 23A), although both HBoV1 and Ad helpers supported an equal level of AAV2 replicative form DNA (FIG. 18 and FIG. 22). This is likely due to the low expression of AAV2 capsid proteins in the presence of HBoV1 helper (FIG. 18 and FIG. 22). It has been reported that AAV2 VP-encoding mRNAs activate PKR and shutdown the host cell translation machinery (Nayak et al., 2007), while VAI RNA acts to overcome the AAV VP mRNA induced activation of PKR (Vachon et al., 2016). Unfortunately, in HBoV1-mediated helper functions, BocaSR does not inhibit PKR (Wang et al., 2017). However, it is also possible that HBoV1 helper gene products transactivate the AAV2 P40 promoter that transcribes VP-encoding mRNAs, or facilitate splicing of these mRNAs, less efficiently than Ad helper gene products (Qiu et al., 2002). Besides AAV2 VP expression, the small Rep proteins (Rep52 and Rep40) (King et al., 2001) are critical for packaging of AAV2 genome and the assembly of activating protein (AAP)(Sonntag et al., 2010), which is critical for capsid assembly. The expression level of Rep52 was lower with HBoV1 Helper as compared to Ad Helper (FIG. 18C). Thus, the low expression of small Rep proteins and/or AAP may also account for the low production of AAV2 from the HBoV1 helper system. Further analysis of the limiting steps and mechanisms underlying AAV2 package in the HBoV1 helper system is warranted.

Function NS2 vs NS4. Although NS4 supported AAV2 DNA replication well in transfection of an AAV2 duplex genome, NS2, but not NS4, is required for productive AAV2 replication following infection. Consistent with this observation, during HBoV1 infection of HAE-ALI, NS2 is also essential, and it is not required for DNA replication of the duplex HBoV1 genome and production of infectious virions in HEK293 cells(Shen et al., 2015). In fact, bocaparvovirus NS2 is unique among all parvoviruses in that it contains a DNA binding (endonuclease) domain and a C-terminal putative TAD domain (Shen et al., 2015; Fasina et al., 2017). It may function as a transcription transactivator, since Ad E1A protein activates the AAV2 P5 promoter to express Rep proteins (Shi et al., 1991; Chang et al., 1989), and that is a critical step in AAV2 replication. This assumption is supported by the fact that, in HeLa cells, which lack expression of Ad E1A, the expression of HBoV1 minimal helper genes fully supports AAV2 DNA replication as efficiently as Ad infection. As NS4 can fully replace NS2 for replication of the duplex AAV2 genome, it is speculate that NS4, which largely is the TAD, also functions as a transactivator, like the HSV transcription transactivator VP16 ((Triezenberg et al., 1988) but without a DNA binding domain. Following AAV2 infection, AAV2 ssDNA genome must be converted to dsDNA replicative form DNA that is transcription-capable template for Rep expression, which is already available when the duplex AAV2 genome is provided. This step should not be a major limiting factor when only NS4, NP1, and BocaSR were provided, since the conventional single-stranded rAAV2 vectors still transduce HEK293 cells and HeLa cells efficiently, although the so-called self-complementary rAAV vector, which bypasses the single to double stranded DNA conversion, delivers transgene expression in higher level and earlier onset (McCarty, 2008). Of note, both NS1 and NS2 contain the OBD of the NS1 (FIG. 16); however, we currently do not know whether NS2 binds to the HBoV1 replication origin. The interaction between NS1 and HBoV1 origin DNA was weak, as assayed by an in vitro binding assay ((Shen et al., 2016) suggesting that the DNA binding activity of NS1 or NS2 (if there is any) requires additional viral or cellular factors. Why NS2 is needed and how it functions in helping AAV2 infection, beyond NS4, are major remaining questions.

Virus co-evolution? Ad, HBoV1, and AAV2 can infect the same tissue, human airway epithelia, and that both Ad and HBoV1 can facilitate AAV2 replication during co-infection. Thus, one can imagine that these viruses may share some similarities by co-evolution in human airway epithelia. To support the AAV2 lytic cycle, Ad E1a, E1b55k, E2a, E4orf6, and VAI RNA are minimal Ad helper genes, while NP1, NS2, and BocaSR are HBoV1 minimal ones. VAI RNA can partially substitute the function of BocaSR in HBoV1 replication (Wang et al., 2017), implying that BocaSR may be evolved from VA RNA. From an evolutionary point of view, NP1 and NS2 are unique genes in bocaparvoviruses, and BocaSR is unique in HBoVs, and, coincidently, these three genes are also the minimal helper genes for AAV2 infection. Therefore, it is reasonable to speculate that the NP1, NS2 and BocaSR genes not only make HBoV1 an autonomously replicating parvovirus, but may also facilitate AAV2 replication in human airway epithelia.

In summary, HBoV1 was identified as a helper virus for AAV2 replication, and only three HBoV1 genes NP1, NS2, and BocaSR are essential to AAV2 productive infection. Thus, an autonomous parvovirus facilitates replication of a dependoparvovirus. This allows for understanding the mechanism underlying the helper functions of individual HBoV1 genes in AAV2 replication, which will provide deep understanding of how AAV2 DNA replicates in cells, and will help develop a better system to produce rAAV vector using these helper genes.

Example III

Figure 24:
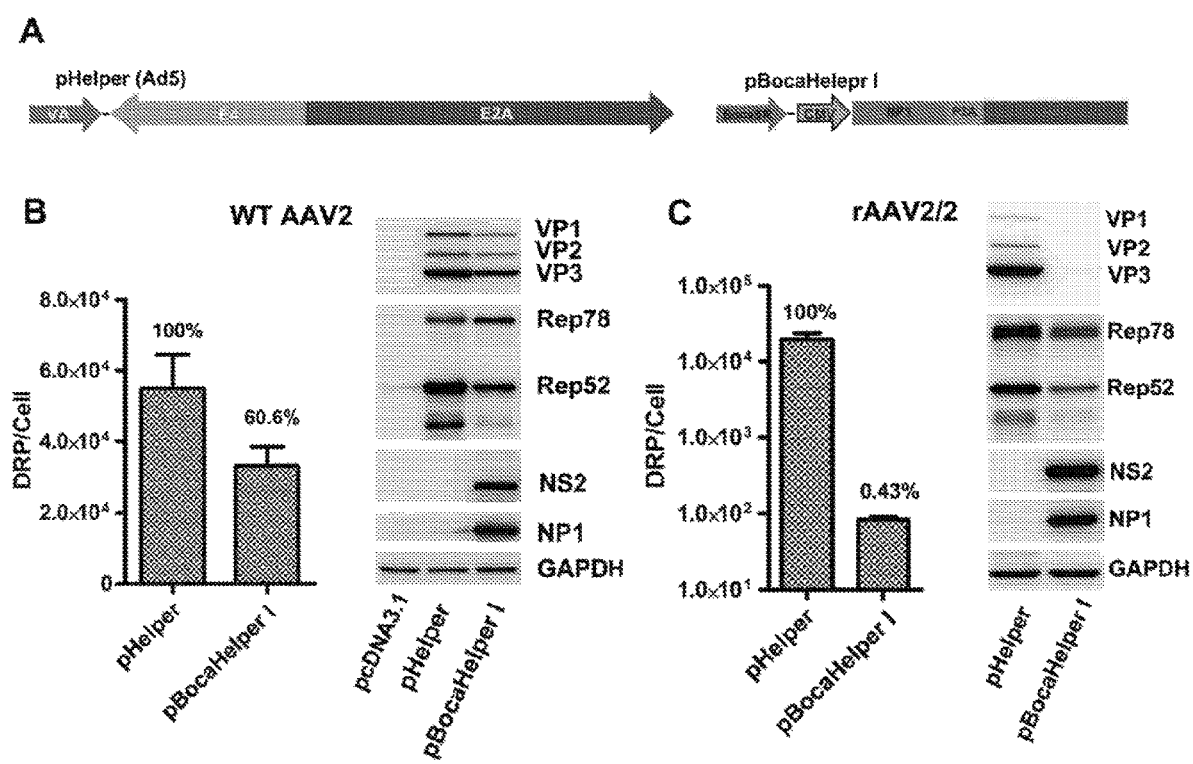

As discussed above (see FIGS. 17-23), HBoV1 is a helper virus supporting wild-type adeno-associated virus (WT AAV) replication in well-differentiated/polarized primary human airway epithelium and HBoV1 genes NP1, NS2, and BocaSR (the bocavirus small noncoding RNA) are the minimal components for WT AAV replication in 293 cells and HeLa Cells. The helper functions from HBoV1 were compared with that from adenovirus for the production of recombinant AAV vector (rAAV) in 293 cells (FIG. 24). Triple plasmid transfection of 1) a cloned HBoV1 minigenome (pBocaHelper) that expresses HBoV1 genes NP1, NS2, and BocaSR, 2) pAAV transfer plasmid, and 3) pAAVRepCap supported rAAV production in 293 cells. Despite a production yield of 1-2 log lower than that using pAdHelper (expressing adenovirus genes E2A, E4 and VAI), rAAV vector produced by pBocaHelper transduced cells as efficiently as that produced by pAdHelper (FIG. 24C).

Figure 25:
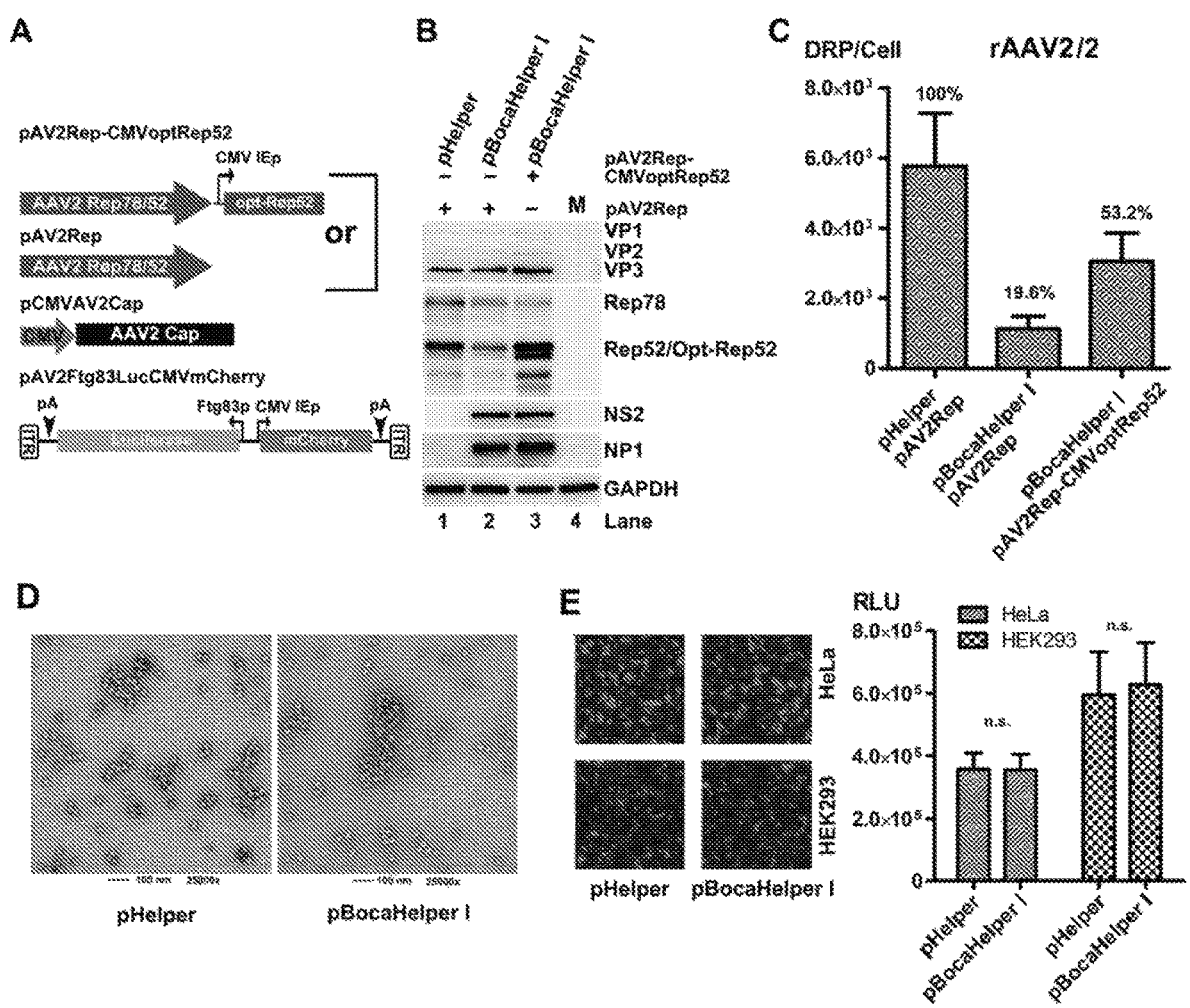
Figure 26:
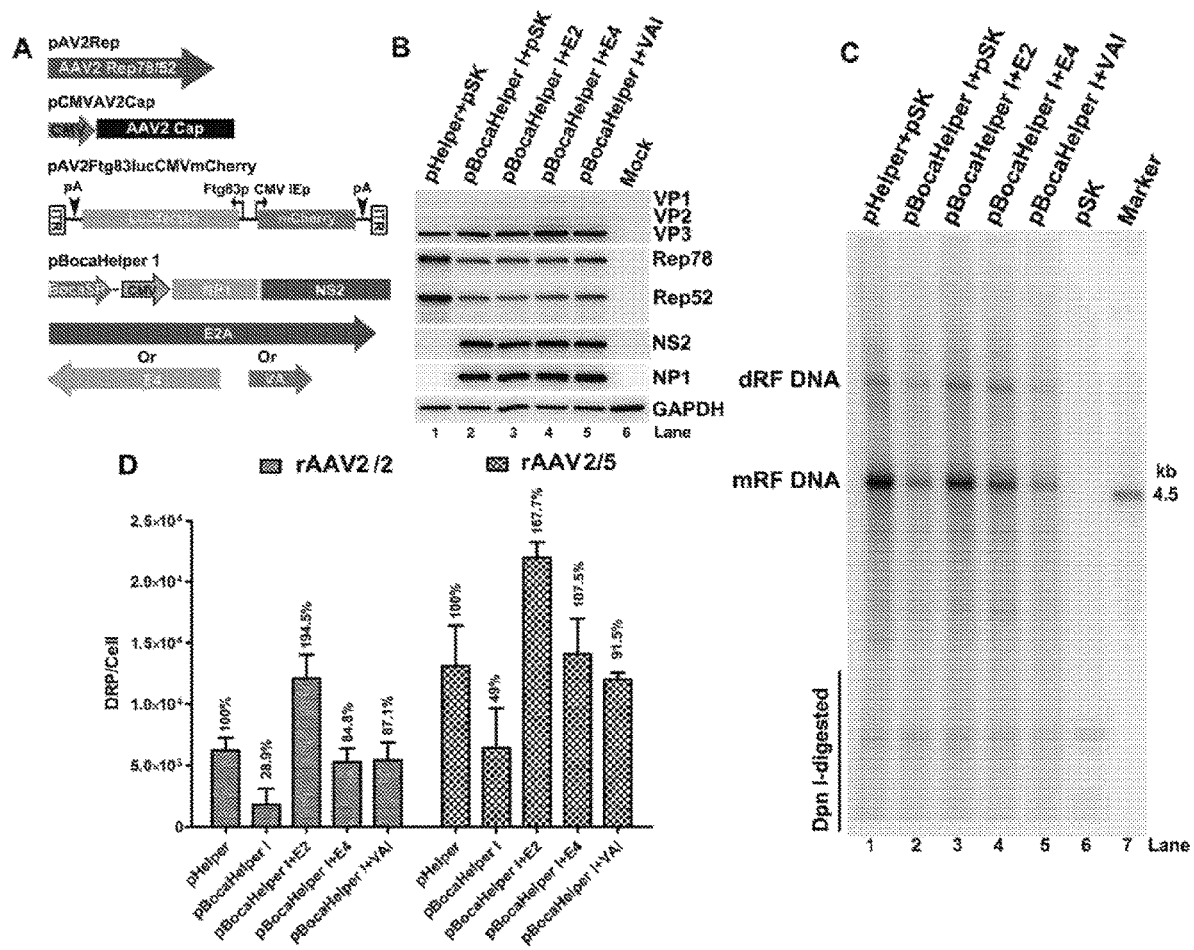

The expression of AAV proteins and the replication of rAAV genome supporting by the transfection of pBocaHelper was examined. Low vector production is largely due to inefficient expression of the AAV Rep52 and capsid proteins, as well as reduced rAAV genome replication (FIGS. 24-25). When the AAV2 P5 promoter in pAV2RepCap was replaced by the stronger CMV promoter, the enhanced expression of Rep52 and capsid proteins significantly improved the rAAV production by pBocaHelper, approaching a level of 50-70% of that produced by Ad pHelper (FIG. 25C). Other promoters that may be useful in this regard include but are not limited to a promoter/enhancer from SV40 virus, EF-1alpha (elongation factor-1 alpha) promoter, CBA promoter (CMV early enhance, chicken beta-actin promoter) or CAG promoter (CMV early enhancer, chicken beta-actin promoter and first intron and the chicken beta-actin gene fused with the splice acceptor of the rabbit beta-globin gene). rAAV2/2 vector produced by pBocaHelper transduced cells as efficiently as that produced by Ad pHelper (FIGS. 25D&E). Through further dissection of the helper functions from Ad pHelper, it was found that an addition of the Ad E2A gene with pBocaHelper significantly increased rAAV DNA replication (FIG. 26). As a result, the rAAV vector production reached a level of two times higher than that using Ad pHelper in 293 cells in the context of overexpression of capsid proteins from the CMV promoter (see FIG. 26).

Finally, based on the above findings, HBoV1 NP1 and NS2 genes were combined with Ad pHelper to create a helper plasmid named as pSuperHelper, for which overexpression AAV genes rep and cap by the CMV promoter is not necessary. Since co expression of two viral RNAs (the BocaSR and VAI RNAs) negatively effect the AAV capsid expression, the Superhelper (which utilizes only minimal components from the two helper viruses, but is superior to pAdhelper) could be either from bocavirus NP1, NS2, BocaSR plus adenovirus E2A or Bocavirus NP1, NS2 and Adenovirus E2A and VA1. Moreover, in the context of the ITR deleted AAV2 helper (pAV2repcap, the bocavirus helper functions (NP1, NS2 and BocaSR) are not sufficient to activate the AAV P5 promoter, so the CMVp is needed. This is different from the wt AAV replication, where the AAVITR might act together with P5 for better function). When the Adenovirus E2A gene expression is incorporated, the P5 promoter in the pAV2repcap functions well.

rAAV production from the system using the pSuperHelper is about 2-fold greater than that from the conventional production system using Ad pHelper. This system may also enable production of rAAV in non-293 cell lines, further expanding the capabilities of large-scale rAAV production. Furthermore, this pBocaHelper packaging system works with multiple AAV serotypes (FIG. 26D).

Example IV

In one embodiment, a vector is provided comprising a nucleotide sequence having SEQ ID NO:1 or a nucleotide sequence having at least 85% identity to SEQ ID NO:1, or a portion thereof, that is capable of regulating bocaparvovirus replication, wherein the vector does not encode bocavirus (BoV) NS1 and optionally does not encode one or more bocavirus VP. In one embodiment, the vector is a bocavirus vector.

In one embodiment, the vector encodes bocavirus NP1 and optionally NS2 or NS4. In one embodiment, the vector comprises a promoter operably linked to the nucleotide sequence. In one embodiment, the promoter comprises a CMV promoter, a CBA promoter (CMV enhancer and beta-actin promoter), a RSV promoter or an ubiquitin C promoter. In one embodiment, the vector further encodes one or more of BoV NS3/4, e.g., NS4, or NS2, NP1, VP1, VP2, and VP3. In one embodiment, the vector further encodes one or more of NP1, NS2 or NS4. In one embodiment, a vector is provided comprising a nucleic acid segment that has a sequence that is a complement to a nucleotide sequence having SEQ ID NO:1 or a nucleotide sequence having at least 85% identity to SEQ ID NO:1, or a portion thereof, that inhibits expression of SEQ ID NO:1. In one embodiment, the vector comprises a promoter which is optionally a PolIII promoter such as a U6 or H1 promoter, or an intron operably linked to the nucleic acid segment. In one embodiment, the nucleotide sequence has at least 90% or at least 95% identity to SEQ ID NO:1. In one embodiment, a method to prevent, inhibit or treat bocavirus infection in a mammal is provided comprising administering to a mammal a composition comprising an effective amount of the vector. In one embodiment, the mammal is a human. In one embodiment, the composition is parenterally administered. In one embodiment, the composition is intravenously injected. In one embodiment, the composition is intranasally or orally administered.

In one embodiment, a helper virus-free method to produce recombinant adeno-associated virus (rAAV) is provided. The method comprises contacting mammalian cells with one or more rAAV vectors and one or more BoV vectors that express one or more of BoV NP1, BoV NS4 or NS2 and a nucleotide sequence having SEQ ID NO:1 or a nucleotide sequence having at least 85% identity to SEQ ID NO:1, or a portion thereof that is capable of regulating bocavirus replication, which cells, rAAV vector or BoV vector or other vector in the cells express AAV Rep and/or AAV Cap, in an amount effective to yield rAAV, wherein the cells and vectors do not express BoV VP1-3; and isolating adenovirus helper-free rAAV from the cells. In one embodiment, the virus is adenovirus-free or bocavirus-free. In one embodiment, the methods includes contacting mammalian cells with i) one or more rAAV vectors, and one or more BoV vectors that express one or more of BoV NP1, BoV NS4 or NS2 and a nucleotide sequence having SEQ ID NO:1 or a nucleotide sequence having at least 85% identity to SEQ ID NO:1, or a portion thereof that is capable of regulating bocavirus replication, which cells, rAAV vector or BoV vector or other vector in the cells express AAV Rep and/or AAV Cap, in an amount effective to yield rAAV, wherein the cells and vectors do not express BoV VP1-3, or ii) one or more rAAV vectors, one or more BoV vectors that express one or more of BoV NP1, and BoV NS4 or NS2, and a vector that expresses at least adenovirus E2A, which cells, rAAV vector or BoV vector or other vector in the cells express AAV Rep and/or AAV Cap, in an amount effective to yield rAAV, wherein the cells and vectors do not express another viral capsid protein such as BoV VP1-3; and isolating adenovirus helper-free rAAV from the cells In one embodiment, the BoV vector expresses AAV Rep and the rAAV vector expresses AAV Cap. In one embodiment, the cells are human cells, ferret cells or mouse cells. In one embodiment, one of the rAAV vectors comprises a transgene. In one embodiment, the transgene encodes cystic fibrosis transmembrane conductance regulator, β-globin, γ-globin, alpha-antitrypsin, tyrosine hydroxylase, glucocerebrosidase, aryl sulfatase A, factor VIII, dystrophin, erythropoietin or other therapeutic gene product, a catalytic RNA, a microRNA, PTM-RNA, a neutralizing antibody or an antigen binding fragment thereof, a prophylactic gene product, a polypeptide or a peptide. In one embodiment, the vector that expresses AAV Rep and/or AAV Cap expresses AAV Rep and/or AAV Cap from a promoter other than AAV endogenous promoters, e.g., P5, P15 or P40. In one embodiment, the titer of the helper free rAAV produced by the method disclosed herein is at least 20%, 30%, 40% 50%, 60%, 70% or more to the rAAV titer obtained in the presence of pAdHelper with rAAV and AAV Rep and Cap. In one embodiment, the titer of the helper free rAAV produced by the method disclosed herein that includes an Ad E2A gene is at least 1.5, 2 or 3, or more, times higher than the titer produced in the presence of pAdHelper with rAAV and AAV Rep and Cap (and in the absence of the BoV genes).

In one embodiment, a method to produce helper virus-free chimeric rAAV/BoV is provided. The method comprises contacting mammalian cells with one or more rAAV vectors and one or more BoV vectors that express one or more of BoV NP1, BoV NS4 or NS2, and a nucleotide sequence having SEQ ID NO:1 or a nucleotide sequence having at least 85% identity to SEQ ID NO:1, or a portion thereof that is capable of regulating bocavirus replication, in an amount effective to yield chimeric rAAV/BoV comprising the genome of at least one of the rAAV, wherein the vectors and cells do not express BoV NS1 or AAV Cap, and wherein at least one of the rAAV vectors or the BoV vectors expresses AAV Rep and/or Bov VP1-3; and isolating chimeric AAV/BoV. In one embodiment, the rAAV expresses BoV VP1-3 and the BoV vector expresses MV Rep. In one embodiment, the cells are human cells, ferret cells or mouse cells. In one embodiment, one of the rAAV vectors comprises a transgene. In one embodiment, one of the rAAVs comprises an expression cassette encoding a heterologous gene product including a therapeutic gene product or a viral, bacterial, tumor, parasite, or fungal antigen, or a heterologous nucleic acid sequence for homologous recombination with selected sequences in the genome of a mammal. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, DNA endonuclease, zinc finger nuclease, a fusion protein including a DNA binding domain linked to a nuclease, or a cytokine, e.g., IFN-alpha, IFN-gamma, TNF, IL-1, IL-17, or IL-6. In one embodiment, the AAV Cap is from AAV-1, AAV-2, AAV-5, AAV-6, AAV-8, or AAV-9. In one embodiment, the BoV VP1, VP2 or VP3 is from HBoV1, HBoV2, HBoV3 or HBoV4.

In one embodiment, a vector is provided having a recombinant BoV genome comprising a LEH, a 3' UTR and a REH, wherein the 3' UTR includes a nucleotide sequence having at least 85% identity to SEQ ID NO:1, or a portion thereof that is capable of regulating BoV replication, wherein the REH includes a 46 nucleotide sequence comprising OriR having a TRS and a NS1 nicking or binding site, wherein the genome encodes bocavirus NP1, NS4 or NP2, VP1, VP2 and/or VP3, or any combination thereof, but not NS1. In one embodiment, the BoV OriR includes nucleotides 5357 to 5402 or nucleotides 5357 to 5430 of SEQ ID NO:25 or a sequence with at least 90% nucleic acid sequence identity thereto. In one embodiment, the OriR includes $(TGT)_a$-$(TGT)_b$-$(TGT)_c$-$(TGT)_d$, where each of a, b, c or d independently is 0 or 1, wherein at least two of a, b, c, and d=1, and wherein if a, b, c and d=1, the T or G in the TGT for no more than two of a, b, c or d may be replaced with C, G, or any combination thereof. In one embodiment, the nicking site includes CTA/TATCT. In one embodiment, the vector comprises a heterologous promoter.

In one embodiment, a method to provide a population of replication incompetent viruses with different BoV or AAV capsid proteins is provided. In one embodiment, the method comprises providing a first composition comprising a population of rAAV having a library of BoV or AAV capsid genes; providing a second composition comprising a rAAV that expresses BoV NP1, BoV NS4 or NS2, and a nucleotide sequence having SEQ ID NO:1 or a nucleotide sequence having at least 85% identity to SEQ ID NO:1, or a portion thereof that is capable of regulating bocavirus or AAV replication; and infecting a first population of cells with the first composition and the second composition in an amount effective to yield a composition comprising a population of progeny viruses that cannot independently replicate, wherein the progeny viruses encode a plurality of the BoV or AAV capsids in the library, and wherein the cells or at least one of the rAAV expresses AAV Rep. In one embodiment, a population of viruses is isolated. In one embodiment, the method further comprises infecting a second population of cells with the isolated population of viruses. In one embodiment, the first population of cells is a different cell type than the second population of cells. In one embodiment, the first population of cells is from a different species than the second population of cells. In one embodiment, the composition comprising the population of progeny viruses does not include any helper virus. In one embodiment, the rAAV having a library of BoV or AAV capsid genes express AAV Rep. In one embodiment, the cells express AAV Rep.

In one embodiment, the rAAV vector production system includes a combination of HBoV1 NP1, NS2, BocaSR and adenovirus E2A, or HBoV1 NP1 and NS2 and adenovirus E2A and VAI. For example, isolated mammalian cells for helper virus-free production of rAAV are provided. In one embodiment, the mammalian cells express a rAAV genome comprising a transgene, express BoV NP1, BoV NS4 or NS2 and a nucleotide sequence having SEQ ID NO:1 or a nucleotide sequence having at least 85% identity to SEQ ID NO:1, or a portion thereof that is capable of regulating bocavirus replication, and express AAV Rep and/or AAV Cap, in an amount effective to yield rAAV, wherein the cells and vectors do not express BoV VP1-3, wherein the cells do not express another viral capsid protein such as BoV VP1-3. In one embodiment, the mammalian cells express a rAAV genome comprising a transgene, express one or more of BoV NP1, and BoV NS4 or NS2, and express adenovirus E2A, and express AAV Rep and/or AAV Cap, wherein the cells do not express another viral capsid protein such as BoV VP1-3.

In one embodiment, an isolated mammalian cell for helper virus-free production of recombinant adeno-associated virus (rAAV) is provided wherein the mammalian cell expresses a rAAV genome comprising a transgene, expresses BoV NP1, BoV NS4 or NS2 and a nucleotide sequence having SEQ ID NO:1 or a nucleotide sequence having at least 85% identity to SEQ ID NO:1, or a portion thereof that is capable of regulating bocavirus replication, and express AAV Rep and/or AAV Cap, in an amount effective to yield rAAV, or wherein the mammalian cell expresses a rAAV genome comprising a transgene, expresses one or more of BoV NP1, and BoV NS4 or NS2, and expresses adenovirus E2A, and expresses AAV Rep and/or AAV Cap; and wherein the mammalian cell does not express viral capsid protein other than AAV Cap.

REFERENCES

Alazard-Dany, N., A. Nicolas, A. Ploquin, R. Strasser, A. Greco, A. L. Epstein, C. Fraefel, and A. Salvetti. 2009. Definition of herpes simplex virus type 1 helper activities for adeno-associated virus early replication events. PLoS. Pathog. 5:e1000340.

Allander, T., M. T. Tammi, M. Eriksson, A. Bjerkner, A. Tiveljung-Lindell, and B. Andersson. 2005. Cloning of a human parvovirus by molecular screening of respiratory tract samples. Proc. Natl. Acad. Sci. U.S.A 102:12891-12896.

Becroft, D. M. 1967. Histopathology of fatal adenovirus infection of the respiratory tract in young children. J. Clin. Pathol. 20:561-569.

Berns, K. I. 1990. Parvovirus replication. Microbiol. Rev. 54:316-329.

Berns, K. I. and C. R. Parrish. 2015. Parvoviridae, p. 1768-1791. In: D. M. Knipe and P. M. Howley (eds.), Fields Virology. 6th ed. Lippincott Williams & Wilkins, Philadelphia.

Chang, L. S., Y. Shi, and T. Shenk. 1989. Adeno-associated virus P5 promoter contains an adenovirus E1A-inducible element and a binding site for the major late transcription factor. J. Virol. 63:3479-3488.

Chen, A. Y., F. Cheng, S. Lou, Y. Luo, Z. Liu, E. Delwart, D. Pintel, and J. Qiu. 2010. Characterization of the gene expression profile of human bocavirus. Virology. 403:145-154.

Cotmore, S. F. and P. Tattersall. 2005. A rolling-haipin strategy: basic mechanisms of DNA replication in the parvoviruses, p. 171-181. In: J. Kerr, S. F. Cotmore, M. E. Bloom, R. M. Linden, and C. R. Parrish (eds.), Parvoviruses. Hoddler Arond, London.

Cotmore, S. F., M. Agbandje-McKenna, J. A. Chiorini, D. V. Mukha, D. J. Pintel, J. Qiu, M. Söderlund-Venermo, P. Tattersall, P. Tijssen, D. Gatherer, and A. J. Davison. 2014. The family Parvoviridae. Arch. Virol. 159:1239-1247.

Deng, X., P. Xu, W. Zou, W. Shen, J. Peng, K. Liu, J. F. Engelhardt, Z. Yan, and J. Qiu. 2016. DNA Damage Signaling Is Required for Replication of Human Bocavirus 1 DNA in Dividing HEK293 Cells. J Virol. 91:e01831-16.

Deng, X., Z. Yan, F. Cheng, J. F. Engelhardt, and J. Qiu. 2016. Replication of an Autonomous Human Parvovirus in Non-dividing Human Airway Epithelium Is Facilitated through the DNA Damage and Repair Pathways. PLoS. Pathog. 12:e1005399.

Deng, X., Z. Yan, Y. Luo, J. Xu, Y. Cheng, Y. Li, J. Engelhardt, and J. Qiu. 2013. In vitro modeling of human bocavirus 1 infection of polarized primary human airway epithelia. J. Virol. 87:4097-4102.

Dijkman, R., S. M. Koekkoek, R. Molenkamp, O. Schildgen, and L. van der Hoek. 2009. Human bocavirus can be cultured in differentiated human airway epithelial cells. J. Virol. 83:7739-7748.

Duan, D., Y. Yue, Z. Yan, J. Yang, and J. F. Engelhardt. 2000. Endosomal processing limits gene transfer to polarized airway epithelia by adeno-associated virus. J. Clin. Invest. 105:1573-1587.

Fasina, O. O., S. Stupps, W. Figueroa-Cuilan, and D. J. Pintel. 2017. Minute Virus of Canines NP1 Protein Governs the Expression of a Subset of Essential Nonstructural Proteins via Its Role in RNA Processing. J. Virol. 91:e00260-17.

Fasina, O. O., Y. Dong, and D. J. Pintel. 2015. NP1 Protein of the Bocaparvovirus Minute Virus of Canines Controls Access to the Viral Capsid Genes via Its Role in RNA Processing. J. Virol. 90:1718-1728.

Ferrari, F. K., T. Samulski, T. Shenk, and R. J. Samulski. 1996. Second-strand synthesis is a rate-limiting step for efficient transduction by recombinant adeno-associated virus vectors. J Virol. 70:3227-3234.

Fisher, K. J., G. P. Gao, M. D. Weitzman, R. DeMatteo, J. F. Burda, and J. M. Wilson. 1996. Transduction with recombinant adeno-associated virus for gene therapy is limited by leading-strand synthesis. J. Virol. 70:520-532.

Flotte, T. R., S. A. Afione, and P. L. Zeitlin. 1994. Adeno-associated virus vector gene expression occurs in nondividing cells in the absence of vector DNA integration. Am. J. Respir. Cell Mol. Biol. 11:517-521.

Guan, W., S. Wong, N. Zhi, and J. Qiu. 2009. The genome of human parvovirus B19 virus can replicate in non-permissive cells with the help of adenovirus genes and produces infectious virus. J. Virol. 83:9541-9553.

Huang, Q., X. Deng, Z. Yan, F. Cheng, Y. Luo, W. Shen, D. C. Lei-Butters, A. Y. Chen, Y. Li, L. Tang, M. Söderlund-Venermo, J. F. Engelhardt, and J. Qiu. 2012. Establishment of a reverse genetics system for studying human bocavirus in human airway epithelia. PLoS. Pathog. 8:e1002899.

King, J. A., R. Dubielzig, D. Grimm, and J. A. Kleinschmidt, 2001. DNA helicase-mediated packaging of adeno-associated virus type 2 genomes into preformed capsids. EMBO J. 20:3282-3291.

Kotha, P. L., P. Sharma, A. O. Kolawole, R. Yan, M. S. Alghamri, T. L. Brockman, J. Gomez-Cambronero, and K. J. Excoffon. 2015. Adenovirus entry from the apical surface of polarized epithelia is facilitated by the host innate immune response. PLoS. Pathog. 11:e1004696.

Kotin, R. M., R. M. Linden, and K. I. Berns. 1992. Characterization of a preferred site on human chromosome 19q for integration of adeno-associated virus DNA by non-homologous recombination. EMBO J. 11:5071-5078.

Lederman, M., J. T. Patton, E. R. Stout, and R. C. Bates. 1984. Virally coded noncapsid protein associated with bovine parvovirus infection. J. Virol. 49:315-318.

Luo, J., Z. L. Deng, X. Luo, N. Tang, W. X. Song, J. Chen, K. A. Sharff, H. H. Luu, R. C. Haydon, K. W. Kinzler, B. Vogelstein, and T. C. He. 2007. A protocol for rapid generation of recombinant adenoviruses using the AdEasy system. Nat. Protoc. 2:1236-1247.

McCarty, D. M. 2008. Self-complementary AAV vectors; advances and applications. Mol. Ther. 16:1648-1656.

Meyer, C., M. Mane, N. Kokorina, S. Alam, and P. L. Hermonat. 2000. Ubiquitous human adeno-associated virus type 2 autonomously replicates in differentiating keratinocytes of a normal skin model. Virology. 272:338-346.

Moore, A. R., B. Dong, L. Chen, and VV. Xiao. 2015. Vaccinia virus as a subhelper for AAV replication and packaging. Mol. Ther. Methods Clin. Dev. 2:15044.

Nash, K., W. Chen, W. F. McDonald, X. Zhou, and N. Muzyczka. 2007. Purification of host cell enzymes involved in adeno-associated virus DNA replication. J. Virol. 81:5777-5787.

Nayak, R. and D. J. Pintel. 2007. Adeno-associated viruses can induce phosphorylation of elF2alpha via PKR activation, which can be overcome by helper adenovirus type 5 virus-associated RNA. J. Virol. 81:11908-11916.

Ni, T. H., W. F. McDonald, I. Zolotukhin, T. Melendy, S. Waga, B. Stillman, and N. Muzyczka. 1998. Cellular proteins required for adeno-associated virus DNA replication in the absence of adenovirus coinfection. J. Virol. 72:2777-2787.

Prince, G. A., D. D. Porter, A. B. Jenson, R. L. Horswood, R. M. Chanock, and H. S. Ginsberg. 1993. Pathogenesis of adenovirus type 5 pneumonia in cotton rats (Sigmodon hispidus). J. Virol. 67:101-111.

Qiu, J. and D. J. Pintel. 2002. The adeno-associated virus type 2 Rep protein regulates RNA processing via interaction with the transcription template. Mol. Cell Biol. 22:3639-3652.

Qiu, J., M. Söderlund-Venermo, and N. S. Young. 2017. Human parvoviruses. Clin. Microbiol. Rev. 30:43-113.

Samulski, R. J. and T. Shenk. 1988. Adenovirus E1B 55-Mr polypeptide facilitates timely cytoplasmic accumulation of adeno-associated virus mRNAs. J. Virol. 62:206-210.

Samulski, R. J., L. S. Chang, and T. Shenk. 1989. Helper-free stocks of recombinant adeno-associated viruses: normal integration does not require viral gene expression. J. Virol. 63:3822-3828.

Schlehofer, J. R., M. Ehrbar, and H. H. zur. 1986. Vaccinia virus, herpes simplex virus, and carcinogens induce DNA amplification in a human cell line and support replication of a helpervirus dependent parvovirus. Virology. 152:110-117.

Schwartz, R. A., J. A. Palacios, G. D. Cassell, S. Adam, M. Giacca, and M. D. Weitzman. 2007. The Mre11/Rad50/Nbs1 complex limits adeno-associated virus transduction and replication. J. Virol. 81:12936-12945.

Shen, W., X. Deng, W. Zou, F. Cheng, J. F. Engelhardt, Z. Yan, and J. Qiu. 2015. Identification and Functional Analysis of Novel Non-structural Proteins of Human Bocavirus 1. J. Virol. 89:10097-10109.

Shen, W., X. Deng, W. Zou, J. F. Engelhardt, Z. Yan, and J. Qiu. 2016. Analysis of the Cis and Trans Requirements for DNA Replication at the Right End Hairpin of the Human Bocavirus 1 Genome. J Virol. 90:7761-7777.

Shi, Y., E. Seto, L. S. Chang, and T. Shenk. 1991. Transcriptional repression by YY1, a human GLI-Kruppel-related protein, and relief of repression by adenovirus E1A protein. Cell. 67:377-388.

Sonntag, F., K. Schmidt, and J. A. Kleinschmidt. 2010. A viral assembly factor promotes AAV2 capsid formation in the nucleolus. Proc. Natl. Acad. Sci. U.S.A. 107:10220-10225.

Srivastava, A. and B. J. Carter. 2017. AAV Infection: Protection from Cancer. Hum. Gene Ther. 28:323-327.

Sun, Y., A. Y. Chen, F. Cheng, W. Guan, F. B. Johnson, and J. Qiu. 2009. Molecular characterization of infectious clones of the minute virus of canines reveals unique features of bocaviruses. J. Virol. 83:3956-3967.

Timpe, J. M., K. C. Verrill, and J. P. Trempe. 2006. Effects of adeno-associated virus on adenovirus replication and gene expression during coinfection. J. Virol. 80:7807-7815.

Triezenberg, S. J., K. L. LaMarco, and S. L. McKnight. 1988. Evidence of DNA: protein interactions that mediate HSV-1 immediate early gene activation by VP16. Genes Dev. 2:730-742.

Vachon, V. K. and G. L. Conn. 2016. Adenovirus VA RNA: An essential pro-viral non-coding RNA. Virus Res. 212:39-52.

Wang, Z. and M. A. Mir. 2015. Andes virus nucleocapsid protein interrupts protein kinase R dimerization to counteract host interference in viral protein synthesis. J. Virol. 89:1628-1639.

Wang, Z., W. Shen, F. Cheng, X. Deng, J. F. Engelhardt, Z. Yan, and J. Qiu. 2017. Parvovirus Expresses a Small Noncoding RNA That Plays an Essential Role in Virus Replication. J. Virol. 91:e02375-16.

Ward, P. 2006. Replication of adeno-associated virus DNA, p. 189-211. In: J. Kerr, Cotmore S F, M. E. Bloom, M. E. Linden, and C. R. Parrish (eds.), The parvoviruses. Hodder Arnold, London.

Weindler, F. W. and R. Heilbronn. 1991. A subset of herpes simplex virus replication genes provides helper functions for productive adeno-associated virus replication. J. Virol. 65:2476-2483.

Weitzman, M. D. and R. M. Linden. 2011. Adeno-associated virus biology. Methods Mol. Biol. 807:1-23.

Weitzman, M. D., K. J. Fisher, and J. M. Wilson. 1996. Recruitment of wild-type and recombinant adeno-associated virus into adenovirus replication centers. J. Virol. 70:1845-1854.

Xiao, W., K. H. Warrington, Jr., P. Hearing, J. Hughes, and N. Muzyczka. 2002. Adenovirus-facilitated nuclear translocation of adeno-associated virus type 2. J. Virol. 76:11505-11517.

Xiao, X., J. Li, and R. J. Samulski. 1998. Production of high-titer recombinant adeno-associated virus vectors in the absence of helper adenovirus. J. Virol. 72:2224-2232.

Yalkinoglu, A. O., R. Heilbronn, A. Burkle, J. R. Schlehofer, and H. H. zur. 1988. DNA amplification of adeno-associated virus as a response to cellular genotoxic stress. Cancer Res. 48:3123-3129.

Yan, Z., D. C. Lei-Butters, X. Liu, Y. Zhang, L. Zhang, M. Luo, R. Zak, and J. F. Engelhardt. 2006. Unique biologic properties of recombinant AAV1 transduction in polarized human airway epithelia. J. Biol. Chem. 281:29684-29692.

Yan, Z., Y. Zhang, D. Duan, and J. F. Engelhardt. 2000. Trans-splicing vectors expand the utility of adeno-associated virus for gene therapy. Proc. Natl. Acad. Sci. U.S.A. 97:6716-6721.

Zou, W., F. Cheng, W. Shen, J. F. Engelhardt, Z. Yan, and J. Qiu. 2016. Nonstructural Protein NP1 of Human Bocavirus 1 Plays a Critical Role in the Expression of Viral Capsid Proteins. J. Virol. 90:4658-4669.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A helper virus-free method to produce recombinant adeno-associated virus (rAAV) or to prepare helper virus-free chimeric rAAV/BoV, comprising:

contacting mammalian cells with i) one or more rAAV vectors, and one or more BoV vectors that express one or more of BoV NP1, BoV NS4 or NS2 and a nucleotide sequence having SEQ ID NO:1 or a nucleotide sequence having at least 85% identity to SEQ ID NO:1, or a portion thereof that is capable of regulating bocavirus replication, which cells, rAAV vector or BoV vector or other vector in the cells express AAV Rep and/or AAV Cap, in an amount effective to yield rAAV, wherein the cells and vectors do not express BoV VP1-3, or ii) one or more rAAV vectors, one or more BoV vectors that express one or more of BoV NP1, and BoV NS4 or NS2, and a vector that expresses at least adenovirus E2A, which cells, rAAV vector or BoV vector or other vector in the cells express AAV Rep and/or AAV Cap, in an amount effective to yield rAAV, wherein the cells and vectors do not express another viral capsid protein such as BoV VP1-3; and isolating adenovirus helper-free rAAV from the cells; or contacting mammalian cells with one or more rAAV vectors, and one or more BoV vectors that express one or more of BoV NP1, Boy NS4 or NS2, and a nucleotide sequence having SEQ ID NO:1 or a nucleotide sequence having at least 85% identity to SEQ ID NO:1, or a portion thereof that is capable of regulating bocavirus replication, in an amount effective to yield chimeric rAAV/BoV comprising a genome corresponding to at least one of the rAAV vectors, wherein the vectors and cells do not express BoV NS1 or AAV Cap and wherein at least one of the rAAV vectors, the BoV vectors or cells expresses AAV Rep and/or Bov VP1-3; and isolating chimeric AAV/BoV.

2. The method of claim 1 for rAAV which is adenovirus-free or bocavirus-free, or both.

3. The method of claim 1 for rAAV wherein the BoV vector expresses AAV Rep and the rAAV vector expresses AAV Cap or wherein one of the rAAV vectors, cells or other vector expresses AAV Rep or AAV Cap.

4. The method of claim 1 wherein the mammalian cells in i) are further contacted with one or more of adenovirus E2A, E4 or VAI, or ii) further contacted with one or more of adenovirus E4 or VAI.

5. The method of claim 1 for rAAV wherein the vector that expresses AAV Rep and/or AAV Cap from a promoter other than AAV2P5, P19 or P40, expresses AAV Cap from a promoter other than AAV P5 or P19, or expresses AAV Cap from a promoter other than AAV P40.

6. The method of claim 5 wherein the vector comprises a CMV promoter a promoter/enhancer from SV40 virus, EF-1alpha promoter, CBA promoter or CAG promoter.

7. The method of claim 1 for helper-free chimeric rAAV/BoV wherein the rAAV expresses BoV VP1-3 and the BoV vector expresses AAV Rep.

8. The method of claim 1 wherein the AAV Cap is from AAV-1, AAV-2, AAV-5, AAV-6, AAV-8, or AAV-9.

9. The method of claim 1 wherein the BoV VP1-3 is from HBoV1, HBoV2, HBoV3 or HBoV4.

* * * * *